United States Patent
Katsuda et al.

(10) Patent No.: US 7,570,984 B2
(45) Date of Patent: Aug. 4, 2009

(54) DIAGNOSTIC IMAGING APPARATUS

(75) Inventors: Naoki Katsuda, Kyoto (JP); Kenji Kino, Kyoto (JP); Kazunari Matoba, Kyoto (JP); Minoru Imazato, Kyoto (JP)

(73) Assignee: J. Morita Manufacturing Corporation, Kyoto (JP)

( * ) Notice: Subject to any disclaimer, the term of this patent is extended or adjusted under 35 U.S.C. 154(b) by 725 days.

(21) Appl. No.: 10/757,064

(22) Filed: Jan. 14, 2004

(65) Prior Publication Data

US 2005/0003323 A1 Jan. 6, 2005

(30) Foreign Application Priority Data

| Jan. 14, 2003 | (JP) | ............................. 2003-006441 |
| Nov. 10, 2003 | (JP) | ............................. 2003-380294 |
| Dec. 5, 2003 | (JP) | ............................. 2003-408054 |

(51) Int. Cl.
*A61B 5/05* (2006.01)

(52) U.S. Cl. ....................... 600/407; 600/476; 600/473

(58) Field of Classification Search .......... 600/407–480
See application file for complete search history.

(56) References Cited

U.S. PATENT DOCUMENTS

| 3,971,954 | A | 7/1976 | Kleinberg et al. | |
| 6,239,868 | B1 * | 5/2001 | Jung et al. | ..................... 356/73 |
| 6,406,293 | B1 * | 6/2002 | Burstein | ..................... 433/29 |
| 6,417,917 | B1 * | 7/2002 | Jung et al. | ..................... 356/73 |
| 6,519,037 | B2 * | 2/2003 | Jung et al. | .................. 356/419 |
| 6,755,647 | B2 * | 6/2004 | Melikechi et al. | ............. 433/29 |
| 2002/0187454 | A1 * | 12/2002 | Melikechi et al. | ............. 433/29 |
| 2003/0011768 | A1 * | 1/2003 | Jung et al. | .................. 356/326 |
| 2003/0152885 | A1 * | 8/2003 | Dinh | ............................ 433/29 |
| 2003/0207228 | A1 * | 11/2003 | Lehmann et al. | ............. 433/26 |
| 2003/0215767 | A1 * | 11/2003 | Taub et al. | .................... 433/29 |
| 2004/0054278 | A1 * | 3/2004 | Kimchy et al. | .............. 600/407 |
| 2004/0166464 | A1 * | 8/2004 | Schneider | ..................... 433/29 |
| 2004/0218039 | A1 * | 11/2004 | Cooper | ......................... 348/66 |

FOREIGN PATENT DOCUMENTS

| EP | 0 941 691 | 9/1999 |
| JP | S63-302818 | 12/1988 |
| JP | S64-074522 | 3/1989 |
| JP | H5-337142 | 12/1993 |

(Continued)

*Primary Examiner*—Brian Casler
*Assistant Examiner*—Nasir Shahrestani
(74) *Attorney, Agent, or Firm*—William L. Androlia; H. Henry Koda

(57) ABSTRACT

A diagnostic imaging apparatus of hand piece type suitable for medical or dental use, comprising a main body held by operator's fingers, a luminous means for irradiating at least one of lights selected from excitation light, infrared light and ultraviolet light, and an imaging means provided in a forward portion of the main body. The imaging means comprises a solid-state image sensing device and an optical means for forming an optical image of a diagnosis object to be examined on the solid-state image sensing device and is so constructed as to output a predetermined diagnostic image information by receiving the light reflected from the diagnosis object and/or the fluorescence generated from the diagnosis object when irradiation of light from the luminous means to the diagnosis object is performed.

31 Claims, 60 Drawing Sheets

FOREIGN PATENT DOCUMENTS

| | | |
|---|---|---|
| JP | H7-144286 | 6/1995 |
| JP | H7-250812 | 10/1995 |
| JP | H9-189659 | 7/1997 |
| JP | 11-047092 | 2/1999 |
| JP | 1999-014904 | 2/1999 |
| JP | 2000-347111 | 12/2000 |
| JP | 2001-258820 | 9/2001 |
| JP | 2002-112961 | 4/2002 |
| JP | 2002-355262 | 10/2002 |
| JP | 2002-535025 | 10/2002 |

* cited by examiner t1: time from radiation start of each LED to image sampling start
t2: waiting time for switching radiating LED
t3: radiation time of each LED time chart to control each light source and a motor for switching filter in accordance with the sequence predetermined by a radiation switch

*Fig. 23a*
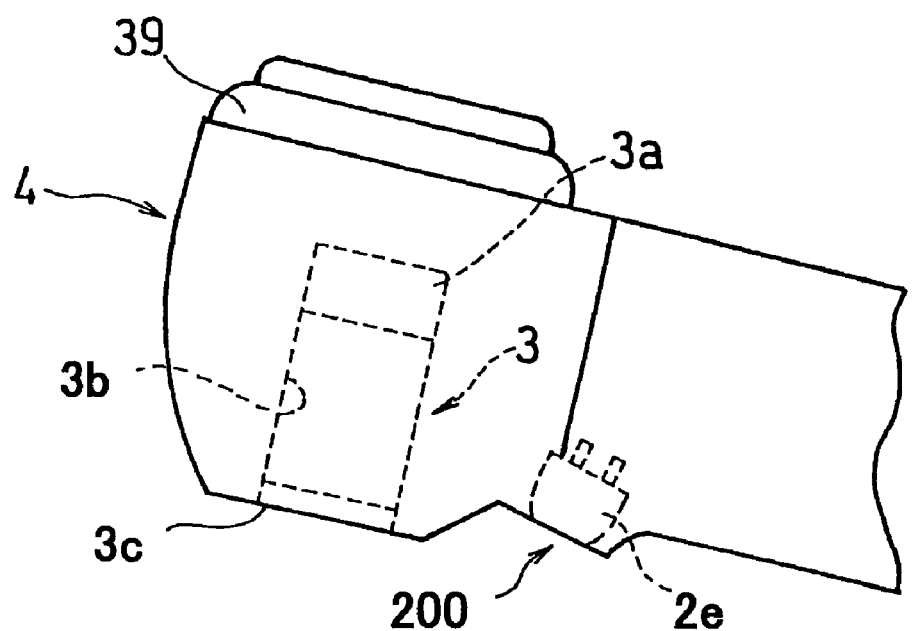
*Fig. 23b*
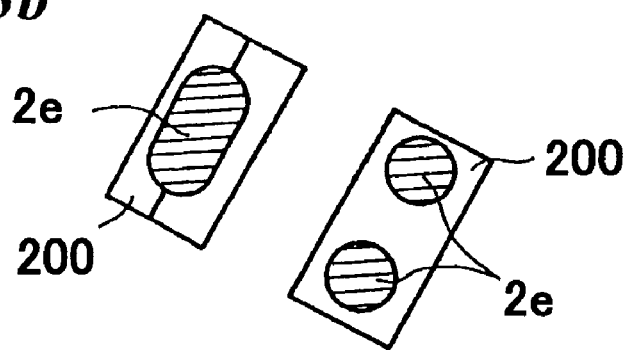
*Fig. 23c* time chart of radiation of each light source selected by each switch and a time chart of drive of a motor for switching filter

DIAGNOSTIC IMAGING APPARATUS

DETAILED DESCRIPTION OF THE INVENTION

1. Field of the Invention

The present invention relates to a diagnostic imaging apparatus for diagnosing dental caries, deficit tooth, crack of tooth, lesioned tooth, attachment of dental calculus or dental plaque, lesioned part of root canal, gum, bucca or tang in oral cavity, for diagnosing otolaryngology area, and for diagnosing rectum tumor. More specifically, the present invention relates to technology which can diagnose in an inner area of a diagnostic object, such as tooth, near the surface as well as on the surface. Further, the apparatus of the present invention isn't limited to an apparatus for doctors and it is preferably used as a diagnostic imaging apparatus for domestic use for confirming the appearance of tooth, dental caries, attached dental calculus or dental plaque.

2. Prior Art

For example, a diagnostic imaging apparatus for diagnosing oral cavity is required to have compactly designed imaging means because the apparatus is inserted and operated in a mouth. The prior diagnostic imaging apparatus is constructed such that a light source for irradiating light to the diagnostic object and CCD imaging means are arranged to be extremely compact to be provided at the forward portion of a main body supported with fingers. Such an apparatus is shown in JP-A-11-047092, JP-B-06-073531 and JP-A-09-189659.

The intraoral photography apparatus as shown in JP-A-11-047092 is formed long and its forward portion is narrow so that the apparatus is easily inserted in oral cavity and imaging can be executed while illuminating in the oral cavity using white LED as an illumination light. Such an apparatus has an advantage of easily photographing a desired part in a narrow oral cavity.

However, such an intraoral photography apparatus can only photograph under the condition where the surface of the tooth or the oral cavity is irradiated with visible light (wavelength of 380-760 nm) so that inside condition of the surface, dental caries or attached dental calculus haven't been accurately understood. Therefore, in has been required to execute radiography in the prior art in order to know dental caries, deficit part, crack or attached dental calculus of biopsy such as invisible tooth, thereby causing a fear of X-ray exposure.

The apparatus disclosed in JP-B-06-073531 is to detect fluorescence with 620 nm wavelength generated from dental caries while irradiating exciting light with 360-580 nm wavelength on tooth. However, the apparatus has the following problems.

(a) A light guide is required to irradiate light to tooth.
(b) Whether a specific part is dental caries or healthy can be determined. However, detection information when exciting light with specific wavelength is irradiated is only obtained so that dental caries condition can't be understood, therefore such information isn't useful for explaining to a patient. In other words, dental caries is locally detected but image information to show relative condition of the dental caries for the entire teeth can't be obtained.
(c) Image processing using plural images such as a visible light image and an exciting light image can't be executed.

The apparatus of JP-A-09-189659 is to detect bad tooth, dental plaque and bacterial infection by detecting fluorescence with 670-800 nm of wavelength by means of exciting light with 600-670 nm of wavelength. Such an apparatus has the following problems, in addition to (b) and (c) mentioned above.

(d) Several kinds of radiation lights such as visible light, infrared ray, ultraviolet ray can't be irradiated with one apparatus so that plural radiation lights aren't irradiated at the same time. Moreover, different radiation lights in time division can't be achieved.
(e) Technical idea such that main mechanisms like a radiation member, a filter, and an image input member are collectively provided in a head portion to form a compact body isn't suggested.

Prior diagnostic imaging apparatus is subject to disturbance light like interior illumination and sunbeam so that clear diagnostic image information has been hardly obtained. Moreover, according to the apparatus disclosed in the above-mentioned prior arts, a standard photography by which the same area is photographed from the same position and from the same angle has been impossible. Still further, a standard photography with radiation light with different wavelength has been also impossible in the prior arts.

SUMMARY OF THE INVENTION

As mentioned above, there is much room for improvement in any prior art. It has been desired an apparatus which has no fear of X-ray exposure, is easily handled, and timely understands the inside condition of the tooth. The present invention is proposed in consideration with the above-mentioned problems and its object is to provide a diagnostic imaging apparatus in which a diagnostic object in a narrow place such as oral cavity is preferably photographed, and clear image information of not only attached condition of dental calculus and dental plaque on the tooth surface but also dental caries in the area close to the surface of the diagnostic object is recognized. Further, its object is to provide a diagnostic imaging apparatus which is hardly subject to disturbance light.

The fist object of the present invention is to receive in an imaging means as an X-ray exposure free, compact and handy apparatus the reflected light generated from the diagnostic object base portion on radiation of light with specific wavelength by a luminous means and the fluorescence generated by the exciting light to obtain a predetermined diagnostic image information, thereby easily and advantageously knowing scratch on the tooth surface, dental caries on and in the tooth, and conditions of dental calculus, dental plaque and gingival. Further, the object is to give an accurate diagnosis making the diagnostic imaging apparatus compact. Solid-state image sensing device (CCD and MOS) and an optical means for forming an optical image of the diagnostic object for the solid-state image sensing device are employed for an imaging means so that preferable photography image information can be rapidly obtained at low cost. The apparatus of the present invention is proposed as a compact and handy apparatus. When it is further commercialized as a compact body at low cast and with safety, such an apparatus with limited function is suitable for domestic use. If the imaging means has wide spectroscopic characteristic such that the light with 300-800 nm wavelength can be photographed, photography of fluorescence range can be executed so that it goes without saying that from ultraviolet light to infrared light including visible light can be photographed. Of course, if detection of specific fluorescence is required, an imaging means with a dedicated wide spectroscopic characteristic with wavelength wider than the above-mentioned range is selected.

In the above-mentioned apparatus, when a luminous means irradiating white light is added, a visible light image (an image obtained by a general intraoral camera with a white light source) can be obtained in addition to the image such as a fluorescence image base portion on radiation of the light with specific wavelength. Namely, the light with specific wavelength and white light can be simultaneously irradiated. When only white light is irradiated and the reflected light is received without passing thought a light receiving filter or is received while passing through a light receiving filter made of glass which passes only visible light, the visible light image of the diagnostic object is obtained. On the other hand, the light with specific wavelength is selectively irradiated, the image (fluorescence image and so on) corresponding to the wavelength characteristic of the diagnostic object can be obtained. Hereby, the obtained visible light image and the obtained image like the fluorescence image are compared, or these images are overlapped and displayed to easily show where the lesion area is on the visible light image and to be easily understood by a patient. Consequently, the image information by which accurate diagnosis is executed while communicating with the patient can be obtained.

The second object of the present invention is, in addition to the above-mentioned object, the forward portion of the main body is made compact and the thickness thereof is made smaller by employing a optical path changing means as an optical means for forming an optical image on a solid-state image sensing device, thereby improving the qualifications as a dental photography apparatus for use in oral cavity.

The third object of the present invention is to improve the cleaning performance and maintenance performance of the forward portion by making the forward portion separate into a head portion including the optical path changing means and a base portion including the solid-state image sensing device. The head portion doesn't include a bulky member such as a solid-state image sensing device so that the thickness thereof can be reduced, thereby further improving the aptitude of the apparatus when being used as a dental photography apparatus for use in oral cavity. Expensive solid-state image sensing device is left at the base portion so that the device is commonly used and different kinds of diagnostic image information can be obtained at low cost by changing the head portion on the characteristic of the optical means such as optical path changing means included in the head portion. Further, the light with specific wavelength and the white light can be simultaneously irradiated. When only the white light is irradiated from the luminous means, the reflected light is received without passing through the light receiving filter or is received while passing through the light receiving filter made of glass which only passes through a visible light, thereby obtaining the visible light image of the diagnostic object. On the other hand, when the light with specific wavelength is selectively irradiated, the image (fluorescence image) corresponding to the wavelength characteristic of the diagnostic object can be obtained. Hereby, the obtained visible light image and the image like the obtained fluorescence image are compared, or these images are overlapped and displayed to easily show where the lesion area is on the visible light image and to be easily understood by a patient. Consequently, the image information by which accurate diagnosis is executed while communicating with the patient can be obtained.

Here the diagnostic image information is a visible light image by the reflected light base portion on the diagnostic object member by radiating white light, a fluorescence image by the fluorescence base portion on the diagnostic object member by radiating exciting light, or an infrared light image reflected by the reflection base portion on the diagnostic object member by radiating infrared light. These diagnostic image information obtained by suitably exchanging the head portion can be turned to practical use as extremely useful information for diagnosing the object.

The forth object of the present invention is to provide a light shielding hood for preventing outside light from entering at a light entrance for going out the radiation light and for entering the light from the diagnostic object at the forward portion, thereby avoiding the affect of the disturbance light such as interior illumination and sunbeam and making clear the diagnostic image information taken by the imaging means. More specifically, by providing the light shielding hood so as to be adjacent to the diagnostic object or so as to fix up the diagnostic object, the adverse effect of disturbance light is avoided and a faint fluorescence image from the diagnostic object by radiating exciting light can be distinguished, thereby being useful for diagnosing a primary dental caries. Still further, if the light shielding hood is used so as to be fixed up the diagnostic object, its positioning is achieved and more accurate diagnostic image information can be obtained. "Preventing outside light" described herein means to prevent all the external light from entering and further to prevent the external light to an extent so as not to affect the diagnostic image information base portion on the diagnostic object by radiating from the luminous means.

BRIEF DESCRIPTION OF THE DRAWINGS

FIG. 19 shows a detachable construction of a filter by means of slide operation.

FIG. 20 shows a detachable construction of a filter.

FIG. 21 shows a detachable construction of a forward portion.

FIG. 23 shows the forward portion of the apparatus of FIG. 22, FIG. 23a is a side view, and FIG. 23b and FIG. 23c are its partial bottom view.

FIG. 24 shows other construction of the forward portion of FIG. 22.

FIG. 51 shows a detachable construction of a filter by means of slide operation.

FIG. 52 shows a detachable construction of the forward portion.

DETAILED DESCRIPTION OF THE INVENTION

Figure 1:
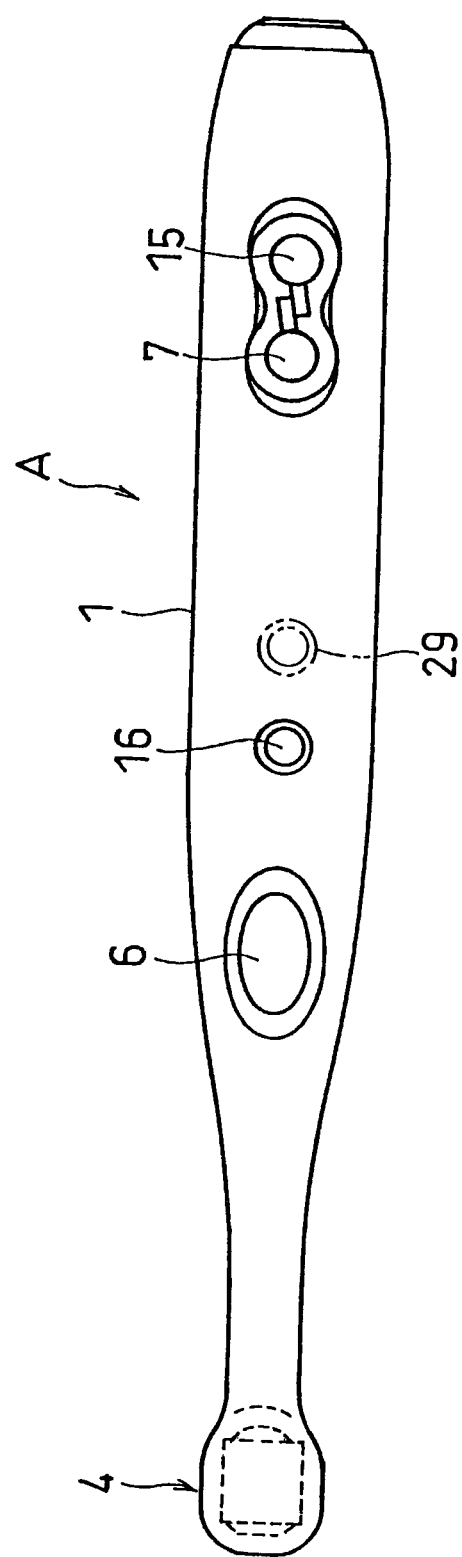
FIG. 1 is a plane view showing one embodiment of the diagnostic imaging apparatus according to the present invention.

Now the embodiments of the present invention will be detailed referring to the attached drawings.

Embodiment 1

The diagnostic imaging apparatus A as shown in FIG. 1-FIG. 5 is comprised of a main body 1 like a dental handpiece freely supported with hands and fingers and a forward portion 4 provided with a luminous means 2 for irradiating at least one of lights among exciting light, infrared light, ultraviolet light, and white light (light emitting member 2a, 2b, 2c) and with an imaging means 3 comprised of CCD (charge coupled device) 3a. The diagnostic imaging apparatus A is preferable for diagnosing mainly dental caries, deficit part, crack, lesioned part, and attachment of dental calculus, dental plaque and bio-film on tooth in oral cavity. The apparatus A can photograph not only the surface of tooth but also the inside of the tooth surface (about 1 mm inside of the surface) to recognize a lesioned part in the surface of the tooth. Moreover, if it is constructed as a cordless type, signals are transmitted to a control box H (see FIG. 2) via cordless manner and the obtained image can be printed out to be taken out. Still further, a zoom mechanism for executing zoom-in and zoom-out and an auto-focus mechanism may be provided. As a solid-state image sensing device constituting the imaging means 3 includes MOS and the equivalent other than the above-mentioned CCD 3a.

The main body 1 is comprised of a casing 5 made of synthetic resin formed by three members, an upper case 5a, a lower case 5b and a forward case 5c. The lower case 5b is fixed to the upper case 5a with four screws 10. The main body 1 of the casing 5 is relatively thick, is once gradually narrowed into its tip side, and is extended from side to side and up and down to form the forward portion 4. The forward case 5c (attachment constituting a part of the forward portion 4) is detachably provided for the upper case 5a and the lower case 5b and has a light receiving filter 12 for the imaging means 3. The reference numeral 5r is a reinforcing rib integrally formed inside of each case 5a-5c.

Figure 5:
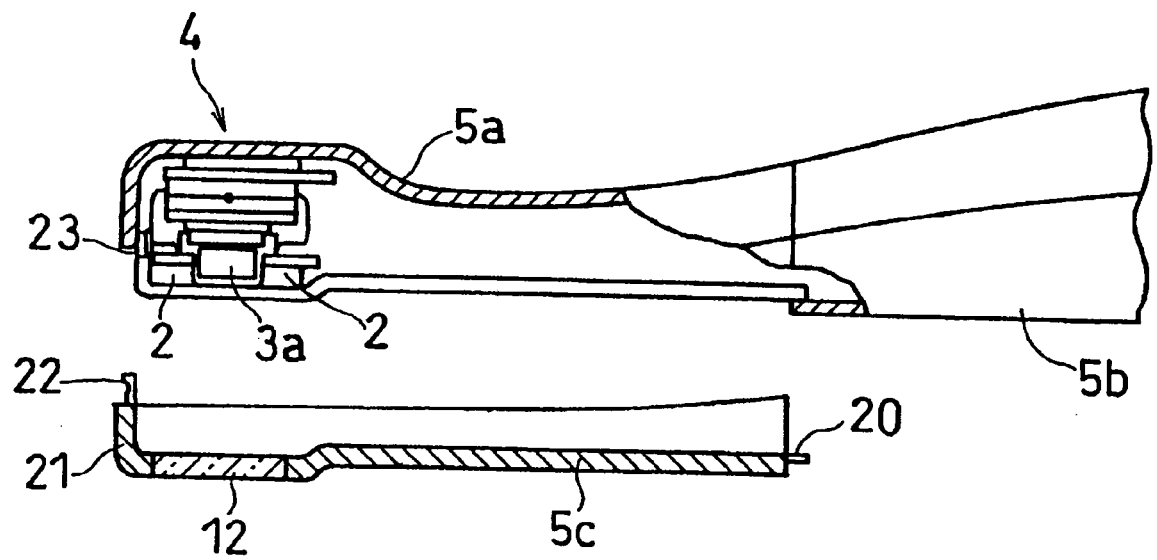
FIG. 5 is a front view of the forward portion of which longitudinal section is partially cutaway.

As shown in FIG. 5, the forward case 5c is constructed such that a tongue piece 20 formed at the end of the case 5c is inserted into the lower case 5b and a hook 22 formed on a vertical wall 21 of its tip end is inserted into an engaging member 23 correspondingly formed on the upper case 5a. For removing the forward case 5c, the tip of the forward case 5c is moved into a direction apart from the upper case 5a so as to release the hook 22 from the engaging member 23, then the forward case 5c is moved into a direction apart from the lower case 5b (left direction in FIG. 5).

As the light receiving filter 12 is provided for the forward case 5c which is detachable to the main body 1, if other forward case 5c with a different light receiving filter 12 is prepared, the light receiving filter 12 is easily exchanged to other one by detaching and attaching the forward case 5c. In FIG. 5, the luminous means 2 is provided for the upper case 5a together with the imaging means 3, however, it may be provided for the forward case 5c to be exchanged together with the light receiving filter 12 when the tip end case 5c is exchanged. In such a case, an electric connection for supplying power to the luminous means 2 may be constructed so as to be freely cut off.

The main body 1 is constructed such that a photography switch (relating to an image storage means for obtaining static image) 6, a light source selection switch 7, an image selection switch 15, an automatic sequence photography switch 16 are attached to the upper case 5a. The main body 1 houses a power supply 8 such as a secondary battery for driving the luminous means (light emitting member) 2 and the imaging means 3, a wireless transmitter 9 for sending the information taken by the imaging means 3 to the control box H, and a micro computer 17. The diagnostic imaging apparatus A is a cordless type which is easily operated because a lead wire isn't pulled. If it isn't a cordless type, the photography switch 6 may be provided for other than the main body 1 such as a control box H and a foot pedal (not shown) connected to the diagnostic imaging apparatus A via a lead wire.

Figure 3:
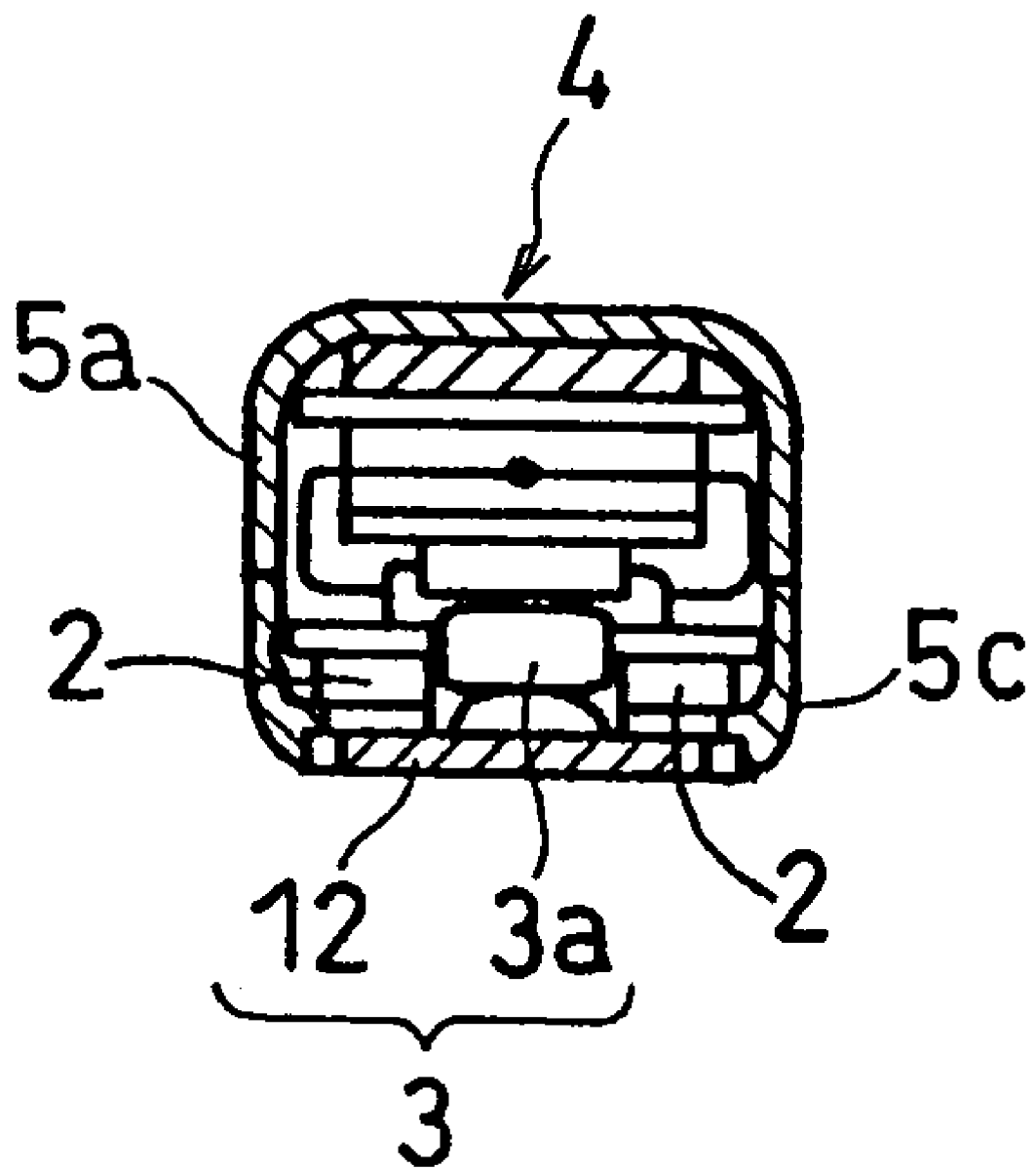
FIG. 3 is a vertical section along the line X-X in FIG. 4.
Figure 4:
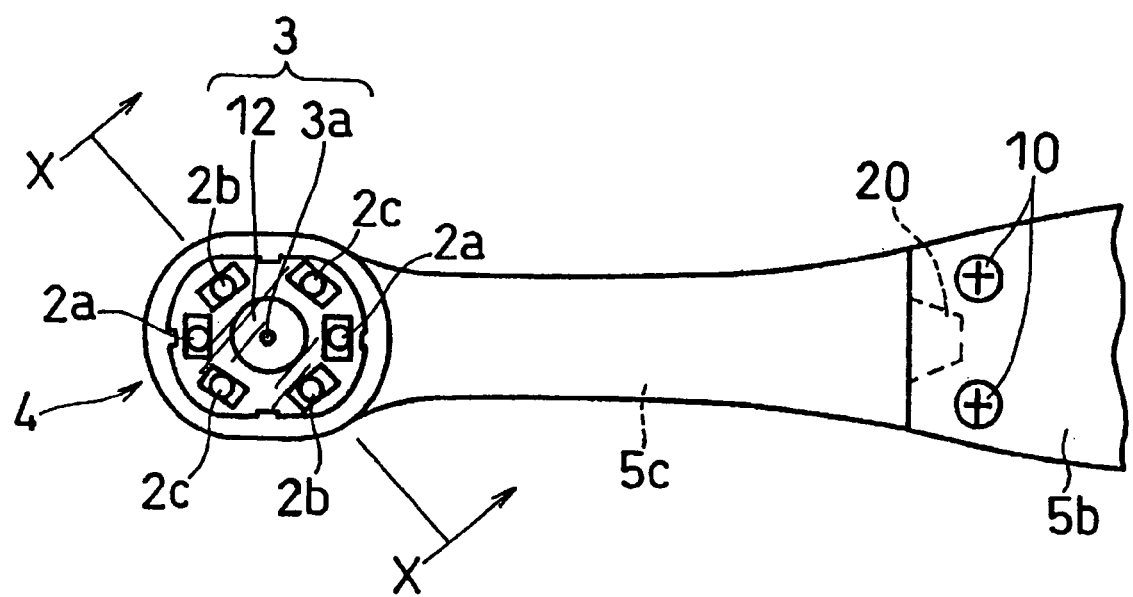
FIG. 4 is an enlarged bottom view of the forward portion of the main body.

As shown in FIG. 3 and FIG. 4, the imaging means 3, the luminous means (light emitting member) 2 and the light receiving filter 12 are provided for the forward portion 4. The imaging means 3 is comprised of the CCD (solid-state image sending device) 3a and the light receiving filter 12 as an optical means. When radiation light is irradiated on the diagnostic object such as a tooth from the luminous means 2, the imaging means 3 receives the light reflected from the diagnostic object and/or the fluorescence generated when the exciting light is irradiated on the diagnostic object and photographs a predetermined diagnostic image.

The luminous means 2 is comprised of six LEDs, namely two pieces of three kinds of LEDs (light emitting diode) as light emitting members, white LED (light emitting diode) 2a, infrared LED (light emitting diode emitting infrared light) 2b and ultraviolet LED (light emitting diode emitting ultraviolet light). LEDs are located around a optical axis of the CCD 3a with an equal angle so as to be rotationally symmetrical. Hereby, the light from the luminous means 2 is directly irradiated on the tooth. Each one of LEDs 2a, 2b, and 2c (light emitting member) is opposed at 180 degrees in a circumferential direction around the imaging means 3. However, the present invention isn't limited to such an arrangement and combination of the radiation source.

The luminous means 2 preferably radiates at least one of exciting light (preferably exciting light with a single wavelength), infrared light, ultraviolet light, and white light. It may be LED, a laser oscillator (semiconductor laser such as He-Ne laser, krypton laser and dye laser or solid laser) or a halogen lamp. Further the luminous means 2 may be white LED, wavelength switching type LED or a laser oscillator. Example of the wavelength switching type LED disclosed in JP-A-6-112589 and JP-A-2002-125982 is known.

By optionally selecting the light emitting member, the fluorescence image, the ultraviolet light image and the infrared light image of the diagnostic object such as a tooth can be obtained, thereby accomplishing an appropriate diagnostic image corresponding to the condition of the diagnostic object. Because the LED is compact, is light-weight and requires low power, it can be easily attached at the forward portion and further the LED with required wavelength characteristic can be selected and used at low cost. On the other hand, the laser oscillator has strong brightness so that clear fluorescence image can be obtained.

Further, if the LED (light emitting diode) or an oscillator which can switch the wavelength of the radiation light is used, it isn't required to use different kinds of luminous means. Therefore, only one kind or minimum kinds of luminous means are required and a radiation filter for transmitting only the light with specific wavelength isn't necessary, thereby improving the compact and light-weight performance and the operation performance of the diagnostic imaging apparatus.

The above-mentioned luminous means (light emitting member) 2 is provided at the forward portion 4 so that the LED and so on are directly and compactly arranged at the forward portion 4 of the main body 1 without using a light guide. Further, unnecessary light diffusion is reduced as far as possible and also illumination irregularity is reduced, thereby providing an efficiently operable diagnostic imaging apparatus.

LED and the laser oscillator may preferably have the visible light range of red, Mars yellow, violet, blue and green in addition to infrared, near infrared, ultraviolet, and near ultraviolet. Specifically, ultraviolet light or near ultraviolet light effective as exciting light can be obtained at low cost by a commonly available LED of which wavelength is around 405 nm or around 400±30 nm. In this case the light receiving filter 12 is preferably designed to transmit only the light with wavelength of longer than 430 nm (the exciting light around 405 nm or 400±30 nm is cut off). Alternately, a notch filter which cuts only exciting light may be used. The wavelength of laser beam emitting exciting light may be around 635 or around 780 nm. In this case it goes without saying that a light receiving filter 12 which cuts off the light with wavelength around 635 nm or around 780 nm is used.

Figure 2:
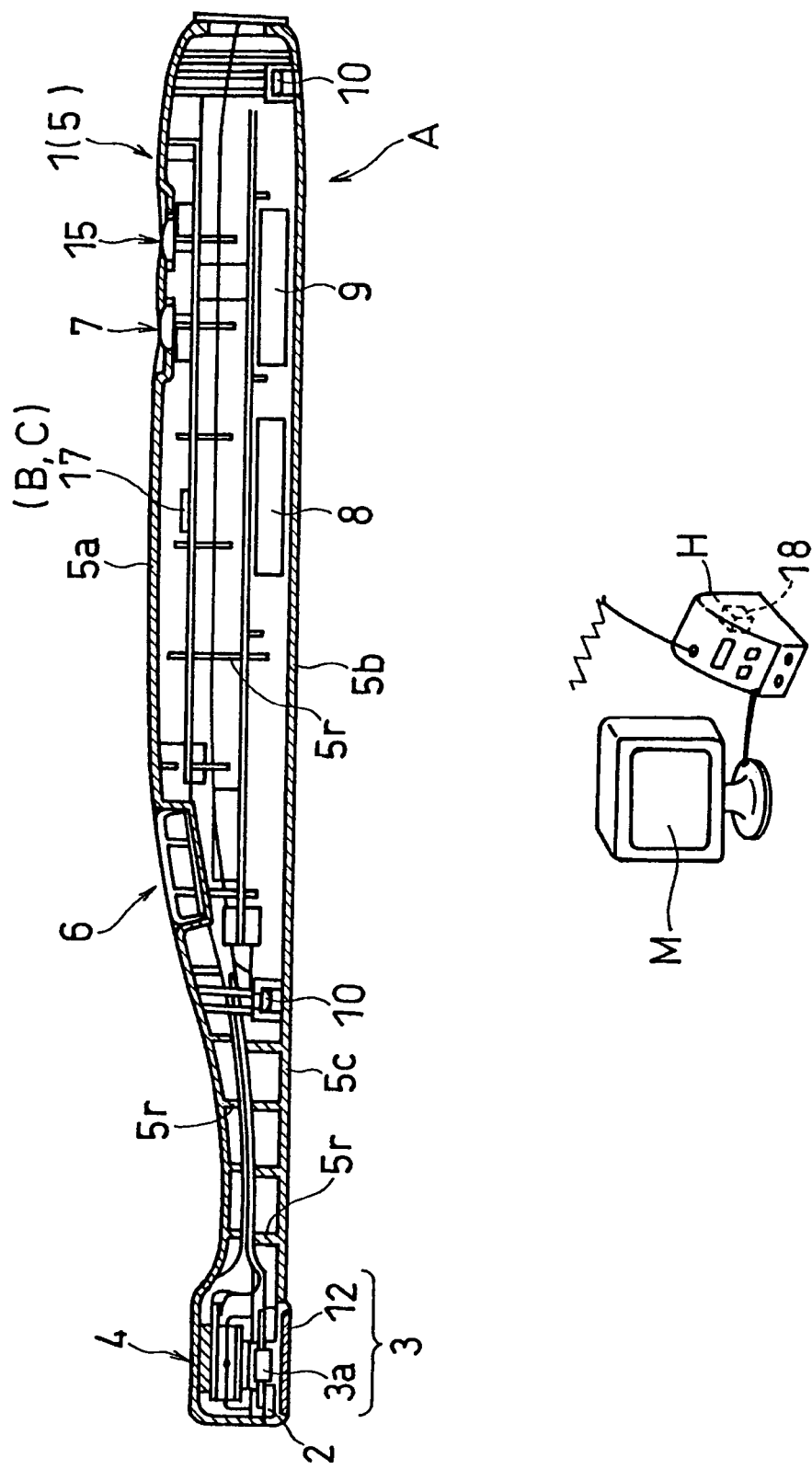
FIG. 2 is a vertical section along the longitudinal direction of the diagnostic imaging apparatus of FIG. 1.

The light receiving filter 12 is fitted in the forward case 5c as shown in FIG. 2-FIG. 4 and is constructed like a circular plate so as to cover under the CCD 3a and six LEDs 2a-2c. When the light receiving filter 12 is thus provided at the forward portion 4, it is advantageous for maintenance such as cleaning. Further if plural kinds of forward portions with a light receiving filter with different wavelength are prepared, accurate diagnostic information appropriate to the diagnostic object can be obtained by selectively attaching the filter, thereby achieving convenience and facilitation.

The light receiving filter 12 transmits only the light with specific wavelength to the light receiving member of the imaging means 3. The circumference corresponding to the luminous means 2 may be constructed so as to pass the light from the luminous means 2 as it is, or the circumference may be constructed as a radiation filter for irradiating the diagnostic object by transmitting the light with specific wavelength among the light emitted from the luminous means 2. Otherwise, the circumference may be a complex filter having both functions of the light receiving filter and the radiation filter. If a radiation filter is provided, the radiation filter is arranged for the luminous means 2, namely which is near the light emitting member and the radiation light hasn't been spread enough so that the radiation filter may be made compact and the radiation light with wavelength appropriate for the diagnostic object can be accurately irradiated through the radiation filter. Further, because only the light with desired wavelength can be irradiated, only required information is obtained and process circuit for cut off unnecessary part from the obtained detection information isn't required. For its purpose, a light source such as a halogen lamp having wide wavelength from ultraviolet light to infrared light including visible light can be used as a luminous means.

The light receiving member of the imaging means 3 in this embodiment indicates the vertical space between the light receiving filter 12 and the CCD 3a at the forward portion 4. In the following embodiments, the light receiving member is used as a concept showing the area in which the light from the diagnostic object directs to the imaging means 3. The light receiving filter 12 in the figure is constructed such that only the light with specific wavelength range is transmitted to the light receiving member of the imaging means 3 and the circumference allows the light from the luminous means 2 to pass through. Glass or any material (space is possible) which passes through the radiation light from the luminous means as it is can be used for the circumference. If only white light is irradiated, a visible light filter which passes through only visible light is preferably used as a light receiving filter 12, however, simply a glass can be used as the filter. Commercially available CCD in which an optical means (not shown) such as a lens forming an optical image on CCD element is integrally incorporated may be used as CCD 3a, however, such a CCD in which a CCD element and a lens are separated isn't excluded in the present invention. That is applicable for the following embodiments.

Figure 7:
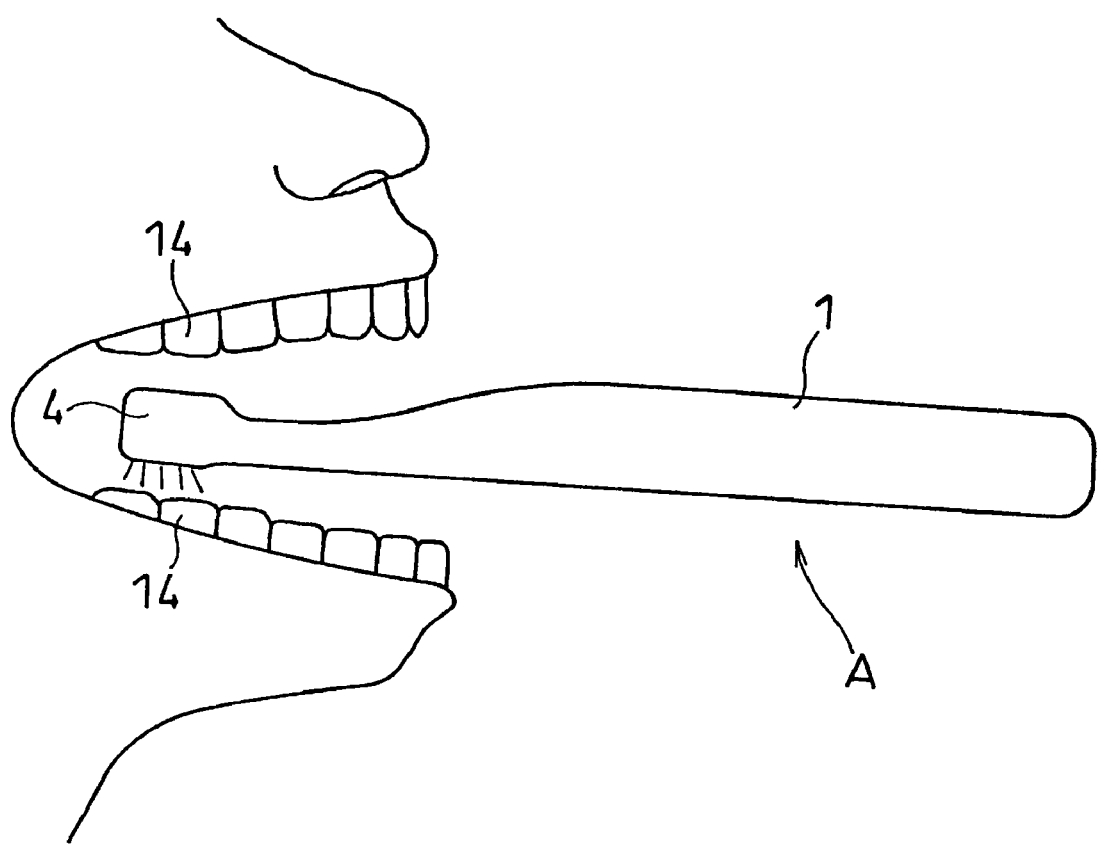
FIG. 7 shows how the oral cavity is diagnosed by means of the diagnostic imaging apparatus.

FIG. 7 shows how the above-mentioned diagnostic imaging apparatus A is used. As shown in the figure, the forward portion 4 of the diagnostic imaging apparatus A is inserted in oral cavity to diagnose the tooth 14 as a diagnostic object. While the image taken by the imaging means 3 is shown on the monitor display M connected to the control box H (see FIG. 2), diagnosis is executed. If there is any interested area, a photograph switch 6 is operated while imaging the area, thereby its still image is stored in the main body 1 or a memory 18 of the control box H to print out the image by means of a printer (not shown) connected to the control box H if necessary. According to this diagnostic imaging apparatus A, the radiation light from the luminous means 2 is directly irradiated on the tooth 14.

Figure 6:
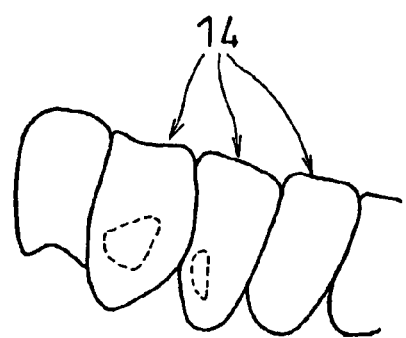
FIG. 6 shows one example of photograph image of teeth in oral cavity.

When the exciting light with wavelength of 400 nm is radiated on the tooth with dental calculus, dental plaque or dental caries (lesioned part) and a light receiving filter passing only the light with the wavelength more than 430 nm is attached to the light receiving member of the imaging means 3, the obtained diagnostic image shows these lesioned part in orange or Mars yellow. FIG. 6 shows the print out image of the teeth 14 obtained by the diagnostic imaging apparatus A. In case of radiation with exciting light, the teeth can be entirely observed, however, not clearer than radiation with white light, and the lesioned part (part illuminating fluorescence) in the image is shown with orange color or Mars yellow. The imaginary line in FIG. 6 shows a lesioned part.

When only the fluorescence image (the area drawn with imaginary line) obtained by fluorescence generated by irradiating exciting light is overlapped on the visible light image (shown with solid line) obtained by the radiation light in a visible light area, and both images are formed and shown as an overlapped complex image, the image in FIG. 6 becomes useful for diagnosis and is suitable to show a patient for explanation use.

Accordingly, dental calculus, dental plaque or dental caries (bad tooth) of the inner area near the surface of the tooth, which isn't seen on the visible light image but is cleared by fluorescence, is clearly recognized on the visible light image of the tooth surface area imaged by visible light. Therefore, where dental calculus, dental plaque or dental caries (bad tooth) exists can be understood at a glance. In FIG. 6 the visible light image and the fluorescence image are overlapped, however, they may be individually shown per each image to be used for diagnosis. Dental caries (bad tooth) is clearly recognized with eyes on the fluorescence image, but teeth image itself isn't clear. On the other hand on the visible light image, teeth outline is clear, so that defects of both images can be compensated by overlapping them. Consequently a high quality diagnostic image information can be obtained in which the teeth outline is clear and dental calculus, dental plaque, or dental caries (bad tooth) is also clear. The system and principle for obtaining such an image will be explained hereinafter.

Figure 8:
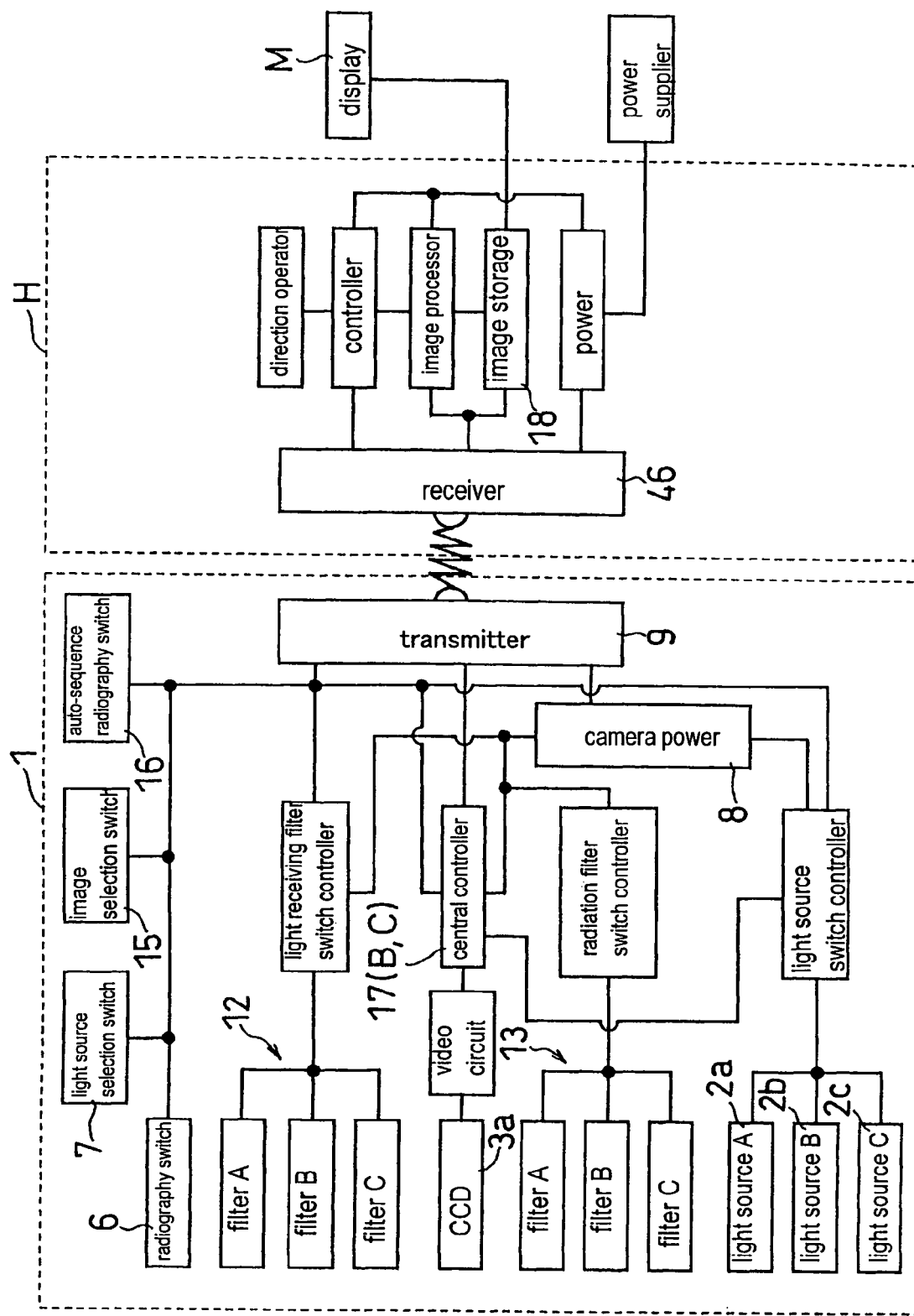
FIG. 8 is a block diagram showing the entire system using a cordless type diagnostic imaging apparatus.

Here one embodiment of the enter construction of the system including the diagnostic imaging apparatus A is explained. As shown in FIG. 8, the system is generally divided into the main body 1, the control box H, and the monitor display M. Signals between the main body 1 and the control box H are sent via wireless (cordless) manner by means of a transmitter 9 and a receive 46. Each construction member is shown in FIG. 8, thereby eliminating each explanation.

The main body 1 is provided with several kinds of switches 6, 7, 15, and 16, a central processing unit corresponding to a microcomputer 17, a control unit for switching light receiving filter and a control unit for switching radiation filter corresponding to a filter changing means F (explained later), a control unit for switching light source corresponding to a radiation light source selection means D (explained later), and a video circuit for converting the signals from the CCD into video signals. The control box H is provided with a receiver 46, a direction operation unit (corresponding to each switch 6, 7, 15, 16), a control unit, an image processing unit, an image storage unit (an image storage means) corresponding to a memory 18, and a power source. Display M such as liquid crystal display and a power supply unit (outlet connected to commercial power) are connected to the control box H.

Figure 9:
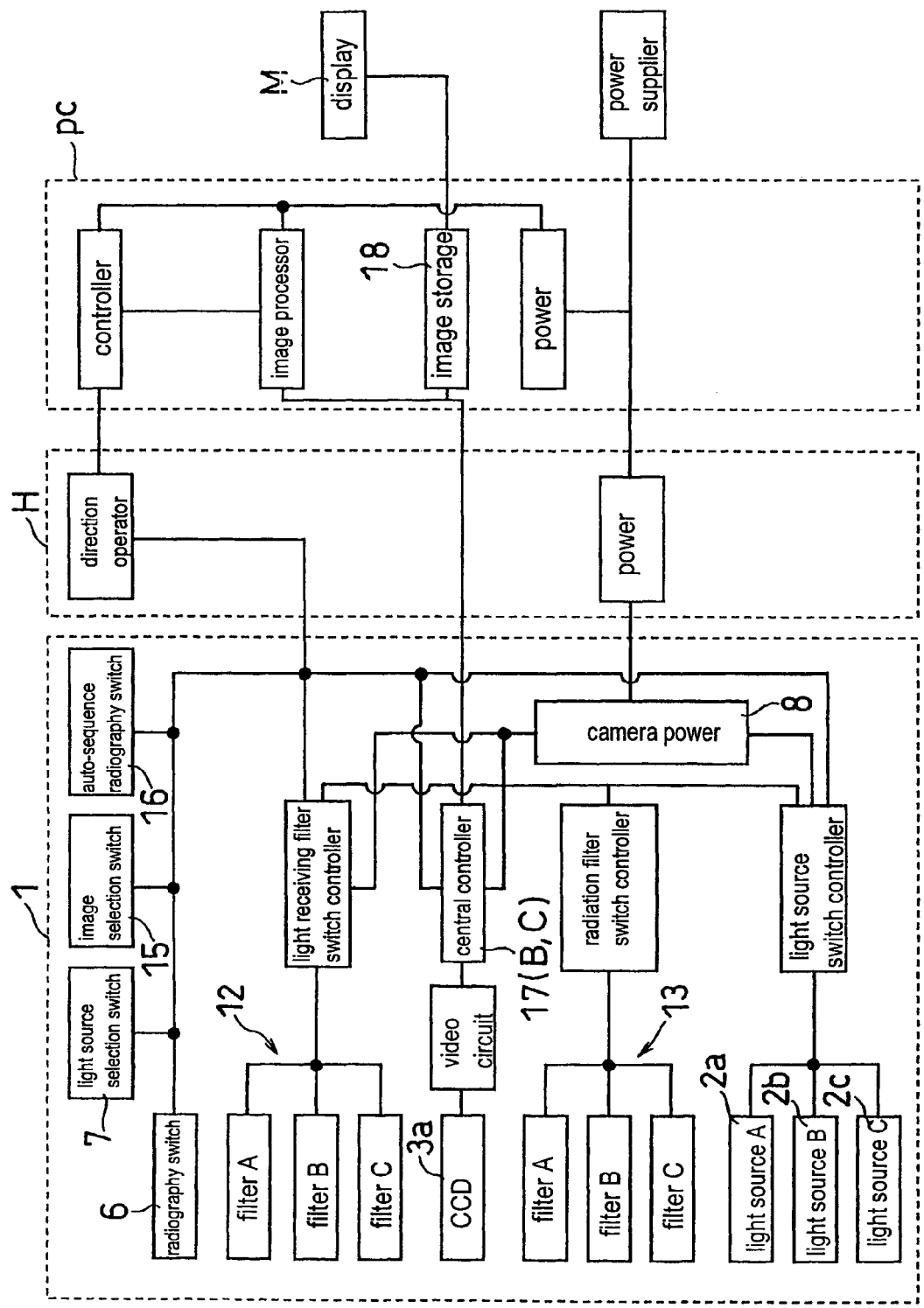
FIG. 9 is a block diagram showing the entire system using a wired diagnostic imaging apparatus and a personal computer.

FIG. 9 shows one embodiment of the entire construction of the wired system including the diagnostic imaging apparatus A by means of a personal computer pc. The main body 1 in the figure is the same as the main body 1 shown in FIG. 8 other than that the transmitter 9 is replaced with a lead wire such as a cable. The control box H is provided with the direction operation unit (same one as shown in FIG. 8) and the power source. The personal computer pc is provided with a control unit, an image processing unit, an image storage unit corresponding to the memory 18, and a power source. It is connected with the display M and the power supply unit.

Thus constructed imaging apparatus A can execute several kinds of photography as mentioned later. Further, the difference of several images are obtained and overlapped images are produced to be stored in the image storage unit in the image processing unit (provided for the control box H in FIG. 8, provided for the personal computer pc in FIG. 9).

The light source selection switch 7 turns on and off three kinds of LEDs 2a, 2b, and 2c (two for 2a, 2b, 2c respectively as shown in FIG. 4). Namely, the light source selection switch 7 is designed as a rotary type switch such that four kinds of turn-on conditions are sequentially switched by pushing the switch 7. The four kinds are; the first condition in which only two white LEDs 2a are turned on, the second condition in which only two infrared LEDs 2b are turned on, the third condition in which only two ultraviolet LEDs 2c are turned on, and the fourth condition in which all six LEDs 2a-2c are turned on.

The image selection switch 15 is designed to select a desired diagnostic image among the diagnostic images which are photographed by operating the photography switch 6 and stored in the memory 18. Each time the image selection switch 15 is pushed down, the selected diagnostic image is sequentially switched over one by one. Therefore, while observing the monitor screen M, a desired diagnostic image is easily picked up among the plural obtained diagnostic images by continuously operating the image selection switch 15. Plural images can be displayed at the same time by means of a personal computer.

An automatic sequence photography switch 16 is to select and operate an automatic photography control means C (explained later). When the automatic sequence photography switch 16 isn't operated, the above-mentioned light source selection switch 7 is operated. By turning on the automatic sequence photography switch 16 (on operation), the operation of the light source selection switch 7 is cancelled and the automatic photography control means C is to be operated. That is, the image storage means B (explained later) is provided with the automatic photography control means C in which a predetermined time sequence is executed by operating the automatic sequence photography switch 16 and the diagnostic image formed by the imaging means 3 is sequentially stored in the memory 18 each time the radiation light with different wavelength is selectively driven. Further, the image storage means B including the memory 18 and the automatic photography control means c is provided for a microcomputer 17.

Figure 10:
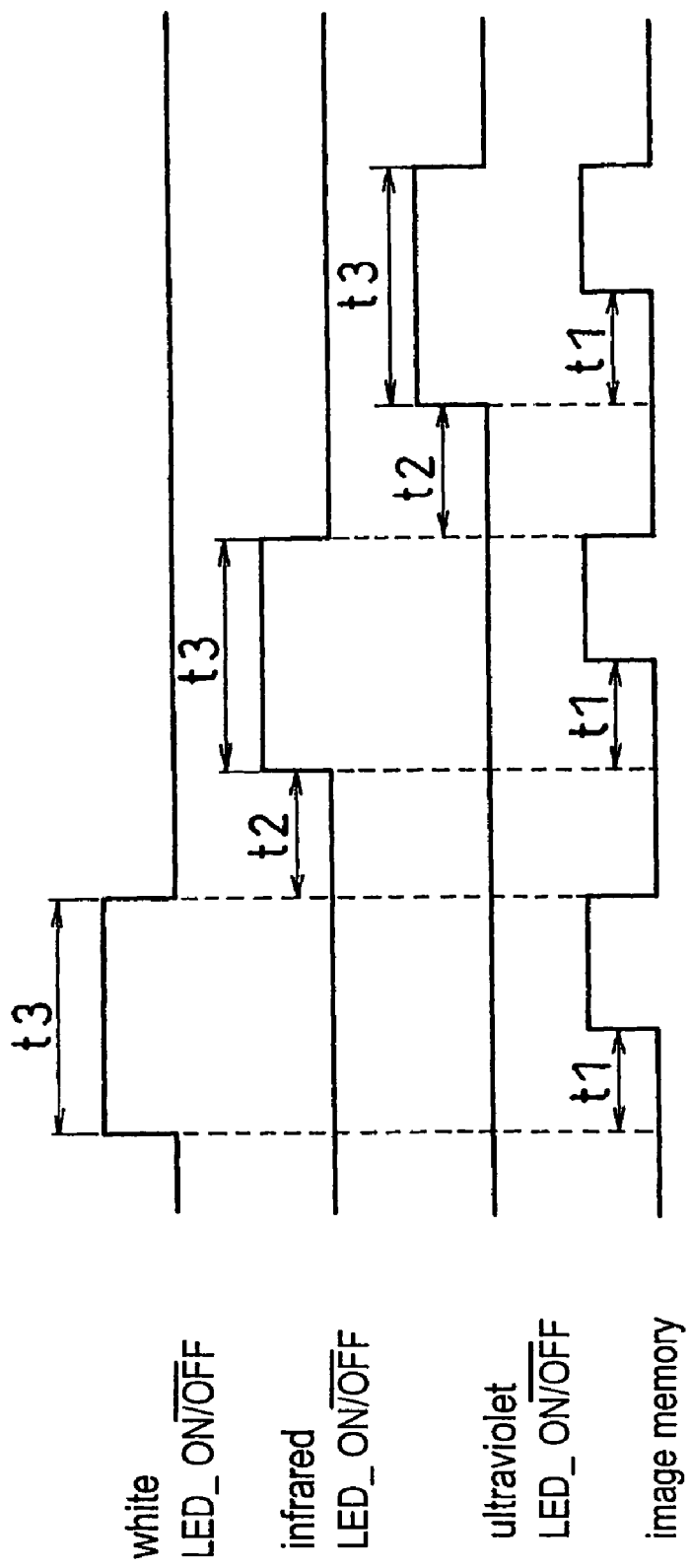
FIG. 10 is a radiation time chart of each light emitting source.

Turning on the automatic sequence photography switch 16, as shown in the time chart in FIG. 10, the cycle in which each one of white LED, infrared LED and ultraviolet LED 2a-2c is irradiated for the time t3 at an interval t2 is repeated. Moreover, after the time t1 from the start of radiating each LED 2a-2c, storage operation of the image taken by the imaging means 3 in the memory 18 is started and is finished at the same time of end of LED radiation. Hereby, the image obtained by radiating only white LED 2a, the image obtained by radiating only infrared LED 2b, and the image obtained by radiating only ultraviolet LED 2c (normal reflection image and fluorescence image) are continuously stored in a short time.

The above-mentioned automatic photography control means C may be designed to automatically start controlling without being operated by the photography switch 6. For example, an operation sequence may be executed such that when the diagnostic imaging apparatus A is moved to a desired place in oral cavity and is stopped for a predetermined time (for instance 1-2 second), automatic photography may be started by detecting the predetermined stop operation (by means of a position detection sensor or a rolling detection sensor). It goes without saying that other sequence may be applied.

Figure 15:
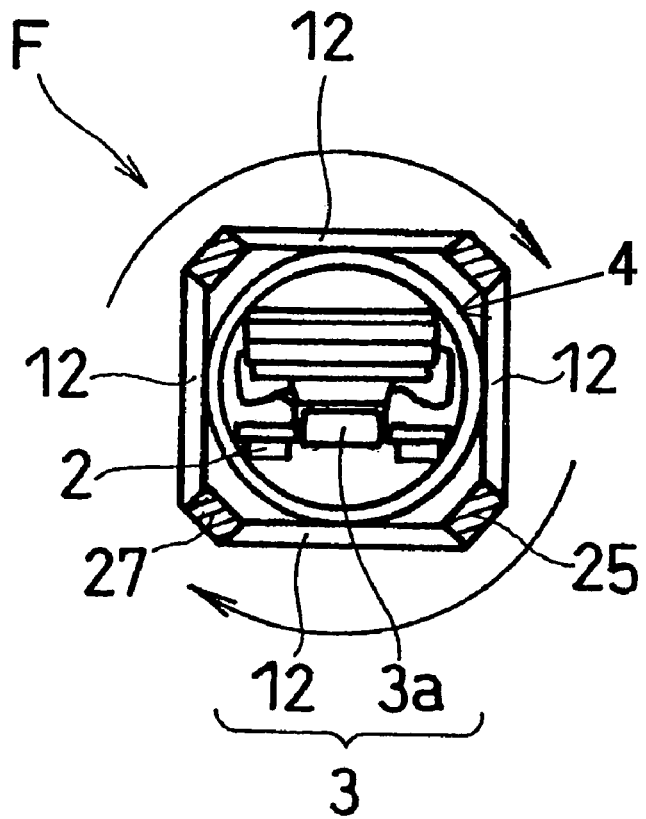
FIG. 15 is a sectional view of a substantial part showing another construction of a filter changing means.
Figure 16:
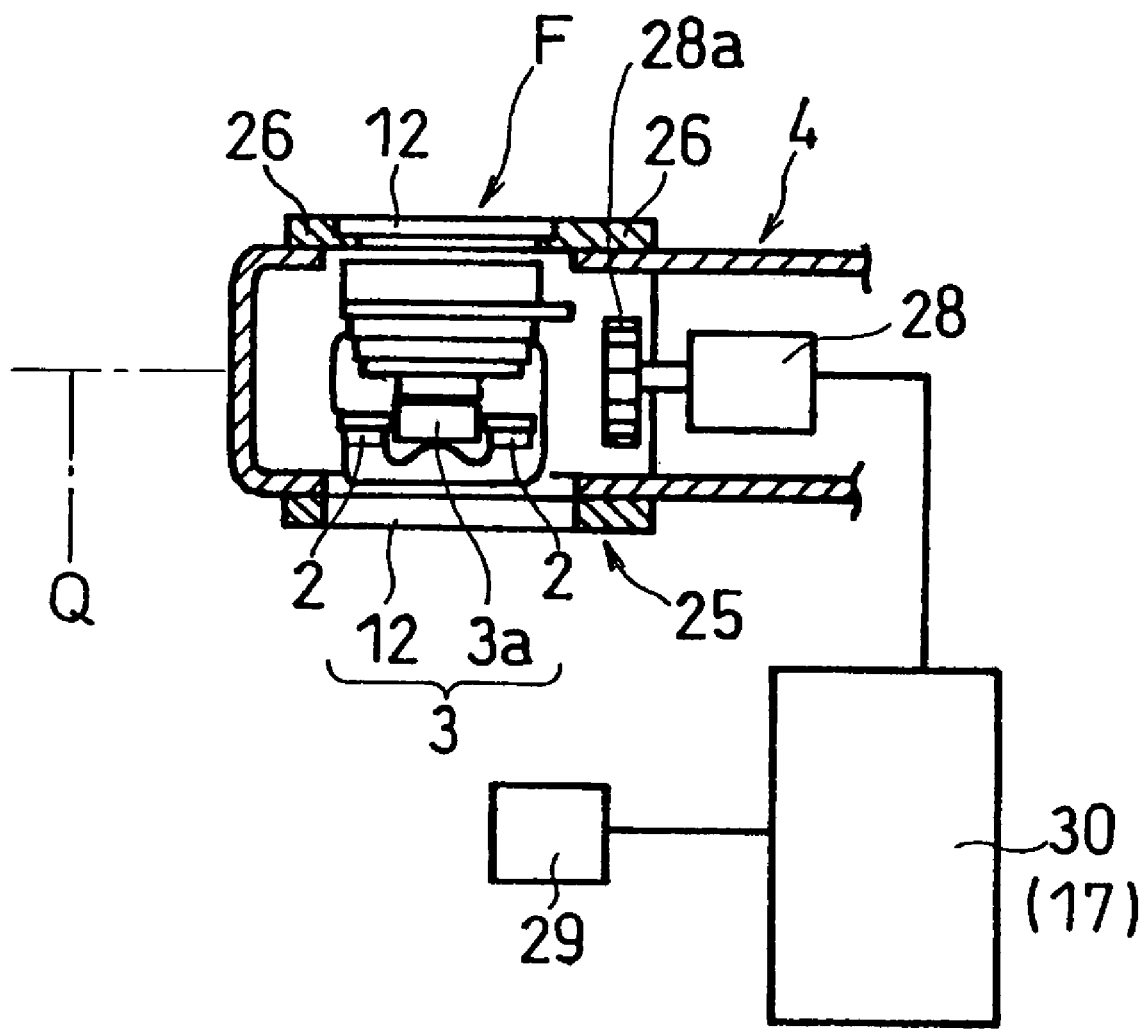
FIG. 16 is a block diagram showing the side view of FIG. 15 and an automatic filter changing means.

Otherwise, as shown in FIG. 15 and FIG. 16, it may be designed such that when the filter switch is operated, one of the plural light receiving filters 12 is rotated by means of a motor 28 incorporated in the main body 1 to automatically switch the light receiving filter 12. Switching the light receiving filter 12, the affect by the radiation light isn't subjected, so that the fluorescence image generated from the diagnostic object becomes clear. The embodiment shown in FIG. 15 and FIG. 16 is detailed later.

Figure 11:
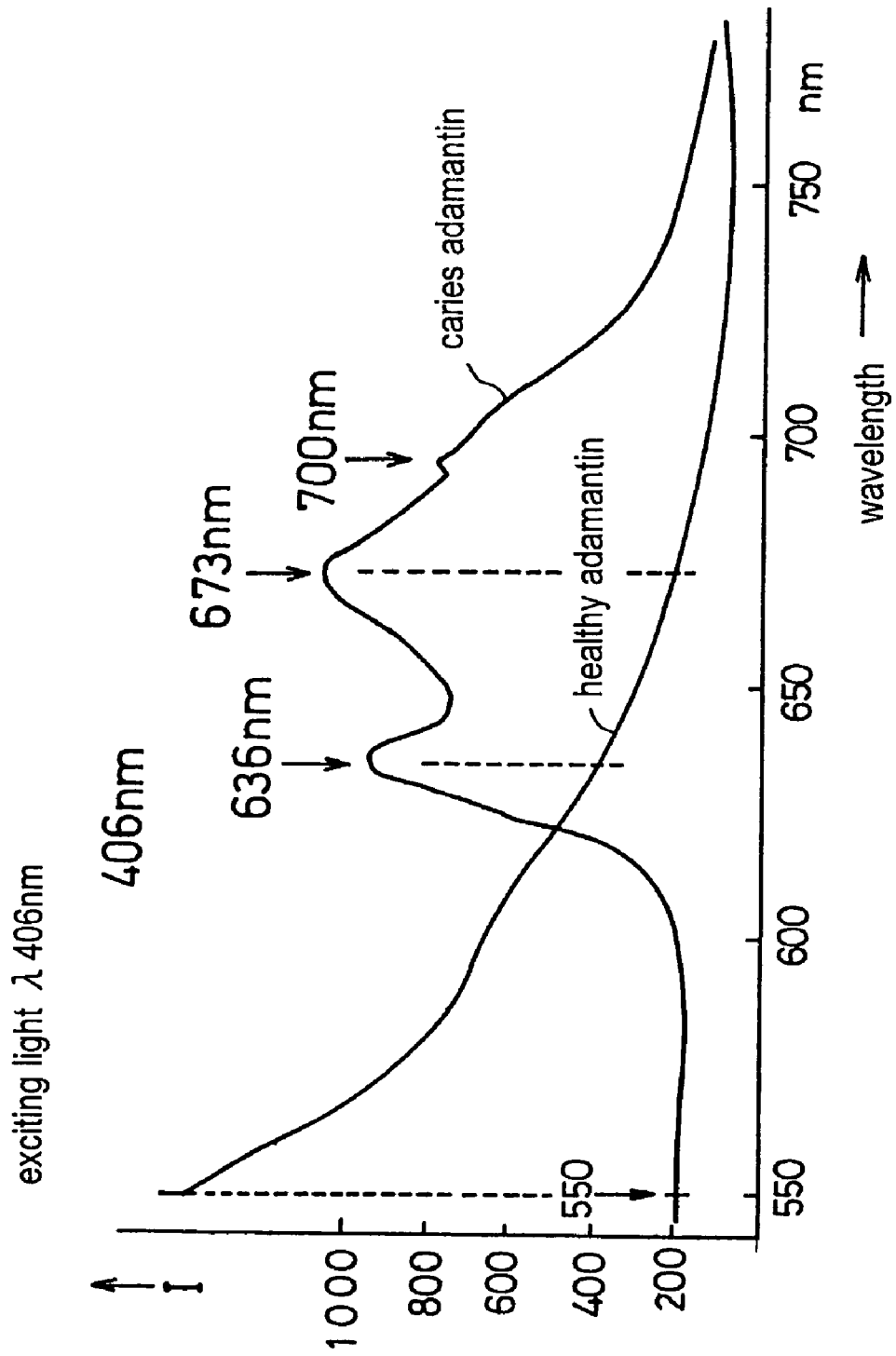
FIG. 11 is a comparison graph of the radiation intensity of dental caries and a healthy tooth by radiating exciting light.

FIG. 6 shows one example of printed out complex image in which the image obtained by fluorescence generated by radiating exciting light (part drawn with imaginary line) is overlapped on the image obtained by the radiation light in visible light range (part drawn with solid line). The principle to obtain such an image is explained. When the radiation light (including exciting light) of LED 2 is irradiated on the tooth 14 as a diagnostic object, fluorescence generated from the tooth 14 is received to obtain a predetermined diagnostic image. However, the wavelength of the fluorescence is different in case of a good tooth and a caries tooth. That is, as shown in FIG. 11, when the light with wavelength of 406 nm is radiated on a good tooth, the radiation intensity I is reduced while the wavelength of fluorescence is increased. However, when it is radiated on a caries tooth, the radiation intensity I for the wavelength of fluorescence shows fluorescence spectrum indicating three peaks (636 nm, 673 nm, and 700 nm). According to experiments, in addition to it, it has been confirmed that fluorescence with orange or Mars yellow is generated. It goes without saying that each image can be shown respectively without being overlapped.

When only the fluorescence images by these peak wavelengths are shown, the caries enamel image can be specified. Further if only the fluorescence image is shown according to its fluorescence intensity, only the caries area can be displayed while showing the entire teeth image. Exciting light and white light are radiated in a pulsating manner (see in FIG. 10), both the fluorescence image and the visible light image by white light can be obtained. Because the entire teeth is recognized in the fluorescence image but it isn't clear, the outline part generating fluorescence is extracted to be cut off and the extracted one and the visible light image by white light are overlapped by the central processing unit 17 to be shown on a display, thereby obtaining the clinically useful image as shown in FIG. 6. Light receiving filter 12 passing only fluorescence is selectively used in order to obtain the fluorescence image. Otherwise, not only the outline but also the entire area of the fluorescence image may be used for image combine.

Actually, the luminous means 2 irradiates the light (exciting light) with 406 nm wavelength on the tooth (diagnostic object), the light receiving filter 12 which doesn't pass the light with wavelength of 406 nm (which passes only the light with wavelength over than 430 nm) is provided for the light receiving member of the imaging means 3, and the imaging means 3 obtains the image by the fluorescence generated from the caries enamel, thereby the exciting light, which has large affect, from the luminous means 2 doesn't enter in the imaging means 3, and extremely clear fluorescence image base portion on the caries tooth can be obtained. Further, the area on which dental calculus and dental plaque are attached can be detected in the same manner. If the exciting light with 400±30 nm wavelength is radiated, a filter which basically passes only the light with more than 430 nm wavelength as its filter characteristic may be used. It has been approved by experiments the light with around 635 nm wavelength and the light with around 680 nm wavelength are useful as exciting light.

Figure 12:
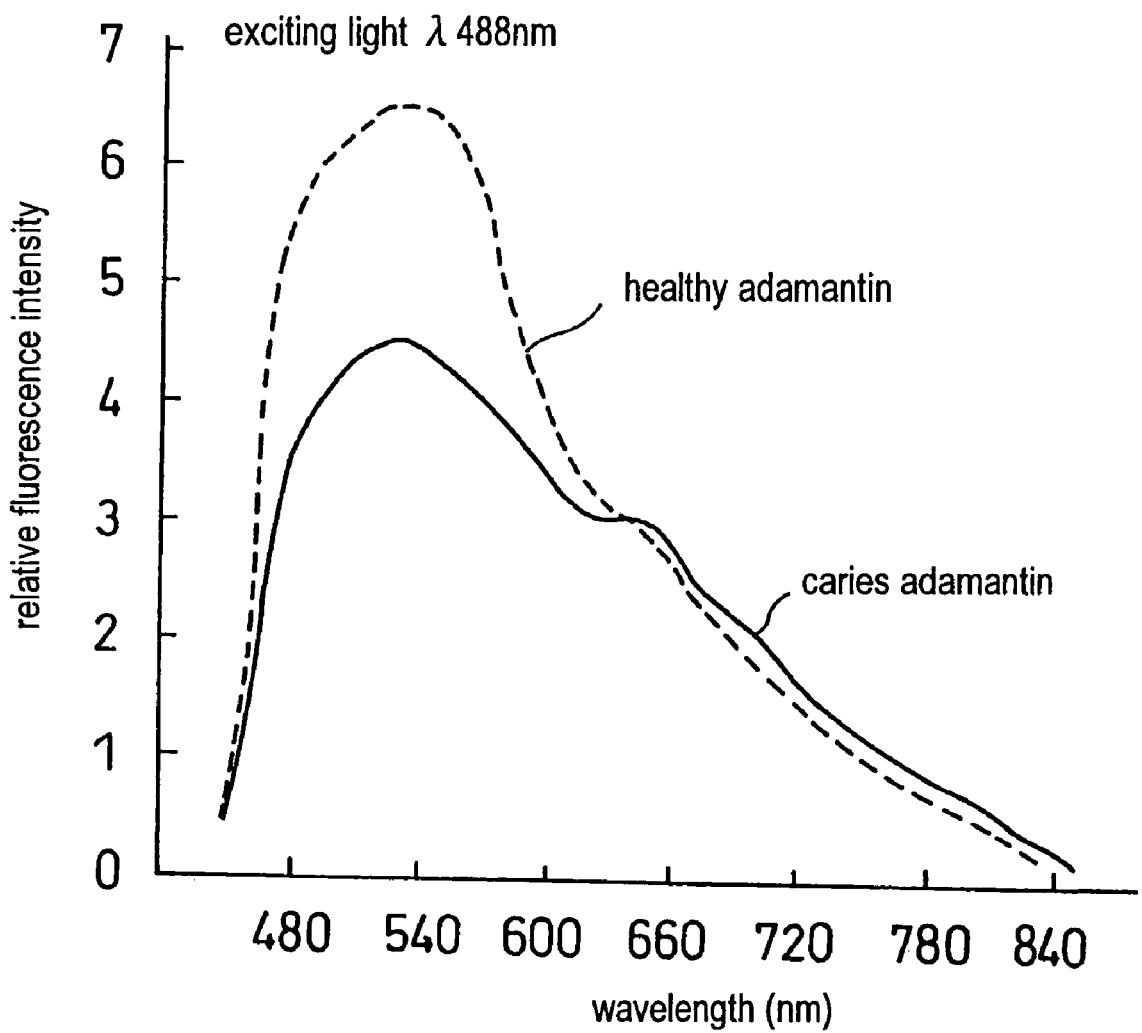
FIG. 12 shows a graph of relative fluorescence intensity of dental caries and a healthy tooth by radiating exciting light.

As shown from the comparison of the graph (comparison graph of fluorescence intensity) in FIG. 11 using 406 nm wavelength radiation light and the graph in FIG. 12 using 488 nm wavelength radiation light, the intensity of the generated fluorescence per wavelength is changed between a good tooth (good enamel) and a caries tooth (caries enamel) when the wavelength of the radiating exciting light is different.

The luminous means 2 includes a halogen lamp or krypton lamp emitting light with wide range wavelength, infrared light LED 2b or ultraviolet LED 2c emitting exciting light with single wavelength, and a laser oscillator (semiconductor laser) outputting ultraviolet ray. For example, if the infrared ray image is detected by the imaging means 3 by selecting a light receiving filter, inside of the teeth can be observed in more detail because the near infrared ray has good permeability comparing with a visible light. Even when the inside of tooth isn't observed, crack of tooth, attached condition of dental calculus, the gap between restoration and tooth substance are clearly observed. Further, the fluorescence image caused by caries is easily diagnosed on the fluorescence image by ultraviolet light. Therefore, the luminous means with different wavelength and the light receiving filter (also the radiation filter depending on the kind of luminous means) are selectively used according to diagnostic purpose and an overlapped image is produced, thereby executing suitable diagnosis. According to the above-mentioned embodiment, the infrared LED is irradiated and only the infrared image is detected in the imaging means by selecting a light receiving filter, however, this invention isn't limited to this embodiment.

Embodiment 2

Figure 13:
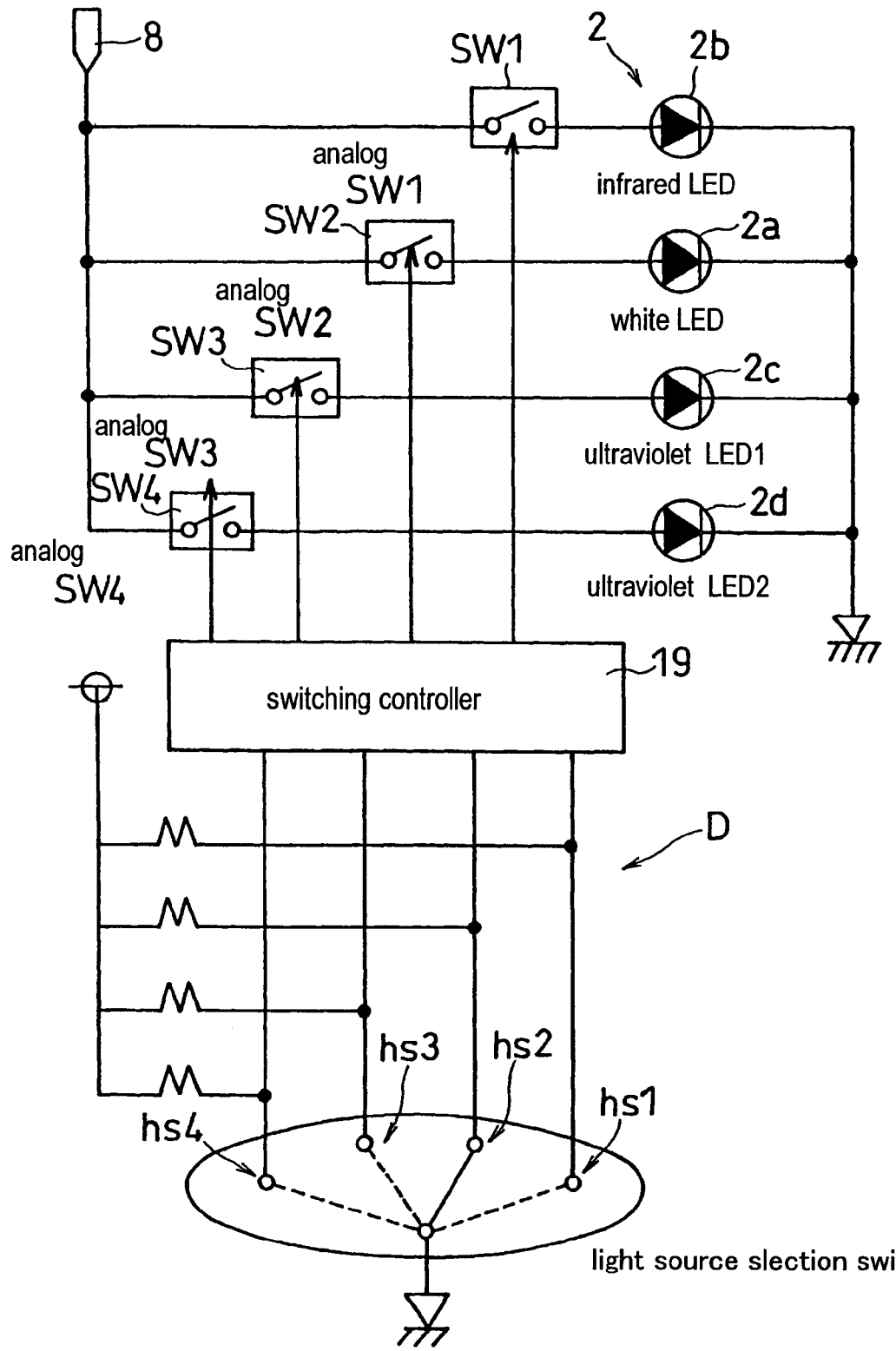
FIG. 13 is a control block diagram showing one embodiment of the switching construction of a radiation light source.

FIG. 13 shows one embodiment of a radiation source selection means D (corresponding to the light source selection switch 7 in FIG. 1). The radiation source selection means D constitutes a luminous means 2 comprised of four kinds of light emitting members 2a-2d (plural light emitting members radiating the light with different wavelength), that is, infrared ray, white light, ultraviolet ray 1 and ultraviolet ray 2, all of them are LEDs. Any one (or plural ones) of the plural light emitting means 2a-2d is (are) selectively driven. The radiation source selection means D is provided with four analog switches sw1-sw4 connected between a power source 8 and each light emitting member 2a-2d, four light source selection switches hs1-hs4, and a switch controller 19.

On operation of the first light source selection switch hs1 enables the first analog switch sw1 to be operated and to drive the infrared LED 2b. In the same manner, on operation of the second light source selection switch hs2 makes white LED 2a driven, on operation of the third light source selection switch hs3 makes ultraviolet (1) LED 2c driven, and on operation of the fourth light source selection switch hs4 makes ultraviolet (2) LED 2d driven. Accordingly an optional kind of radiation light can be selected. Of course the obtained diagnostic images have different characteristics depending on the radiation light and the filter.

Embodiment 3

Figure 14:
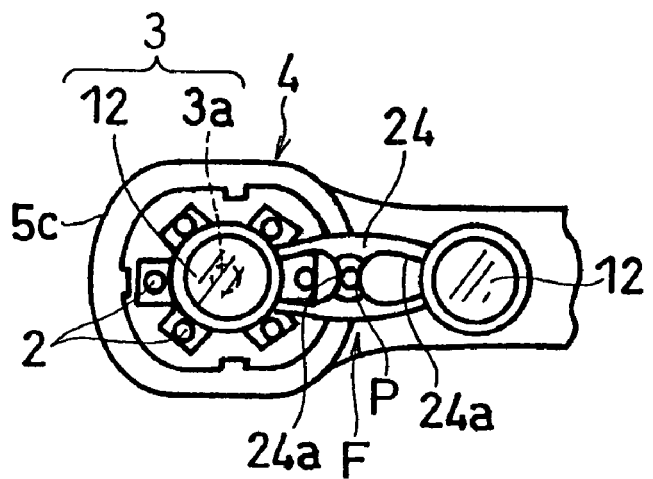
FIG. 14 is a bottom view showing one embodiment of a filter changing means.

FIG. 14 is one embodiment of the light receiving filter changing means. The filter changing means F in the figure is designed such that a support frame (filter unit) 24 provided with two light receiving filters 12, 12 with different cut-off wavelength range at both ends respectively is arranged so as to be freely rotated by hands around the center P of the axis parallel to the optical axis of the imaging means 3 (or luminous means 2). When the support frame 24 is rotated 180 angles around the axis center P, the light receiving filter 12 as shown in FIG. 14 is switched to another light receiving filter 12 (having different permeability).

The support frame 24 is constructed in a manner that a penetrating window 24a is formed between the axis center P and the light receiving filters 12, 12 respectively so as not to prevent the light from the luminous means 2 from transmitting. The support frame 24 may be rotated in the reverse direction as mentioned above or more than three light receiving filters 12 may be provided. The light receiving filters 12, 12 are arranged on the same circle around the axis center P. Such a switching operation is combined with the light source selection switch control described in the embodiment 2, enabling easy switching operation of the light receiving filter together with switching operation of the radiation source.

Embodiment 4

FIG. 15 and FIG. 16 show another light receiving filter changing means. According to the filter changing means F in the figure, plural light receiving filters 12 are externally fitted up the forward portion 4 of the main body rotatably around the center Q of the axis in a direction perpendicular to the optical axis of the imaging means 3 or the luminous means 2. A square and tubular cover (filter unit) 25 comprised of a different light receiving filter 12 (with different permeability) at four faces, up, down, right and left is externally fitted up the forward portion 4 so as to be freely rotated. When the cover is rotated at 90 degrees, the light receiving filter 12 positioned directly under the CCD 3a can be switched to the next light receiving filter 12 apart from 90 degrees.

The cover 25 is formed like a hollow tube and is comprised of a cylinder 26 at both ends which is externally fitted up the cylindrical forward portion 4 so as to be freely rotated in its circumferential direction and a filter support member 27 like roughly angular tube with four light receiving filters 12. The light receiving filter 12 in the figure is designed to transmit the light as it is from the light emitting member serving the position corresponding to each light emitting member of the luminous means 2 as a transparent hole. However, a filter for luminous means may be fitted in the transparent hole, or the radiation filter is incorporated to be constructed as a radiation filter changing means without providing the light receiving filter 12. Detent mechanism (light fitting member by concavo and convex) is preferably provided for the cover 25 or the support frame 24 so as to engage and keep the light receiving filter 12 at a correct position corresponding to the imaging means 3.

FIG. 16 shows a mechanism in which the filter is automatically switched by the filter changing means F shown in FIG. 15. The mechanism is provided with an electric motor 28 such as a step motor for driving and rotating the cover 25 around the axis center Q, a filter switch 29, and a switching control means 30 for rotating and moving the cover 25 by executing drive control of the electric motor 28 base portion on the filter switching signal by means of the filter switch 29, thereby constructing a semi-automatic filter changing means F.

Output rotation body 28a of the electric motor 28 is internally contacted with the cylinder 26 of the cover 25 from a penetrating hole (not shown) formed at the forward portion 4. When the filter switch 29 is operated one time, the electric motor 28 is controlled by the switching control means 30 so as to rotate the cover 25 at just 90 degrees around the axis center Q so that the light receiving filter 12 is switched into next light receiving filter 12. Namely, the filter is easily, accurately and rapidly switched only by one action of operating the filter switch 29.

The filter changing means F is constructed such that the motor 28 for driving and rotating the plural light receiving filters 12 around the axis center Q is provided and is comprised of the switching control means 30 for switching the light receiving filter 12 by executing drive control of the motor 28 base portion on the filter switching signal operated by the filter switch 29. Hereby when the light receiving filter is switched by the motor in synchronous with switching of the radiation light, different kinds of diagnostic images can be easily obtained. The embodiment in FIG. 15 and FIG. 16 is shown as a light receiving filter changing means, however, such a mechanism may be applied to a radiation filter changing means. If a (white light) halogen lamp or white LED with wide wavelength is used as the luminous means 2 in order to obtain a visible light image, a radiation filter isn't required. However, if the light with specific wavelength is intended to be radiated by means of LED and a semiconductor laser, it is effective to switchably provide the radiation filter for the luminous means 2.

Figure 17:
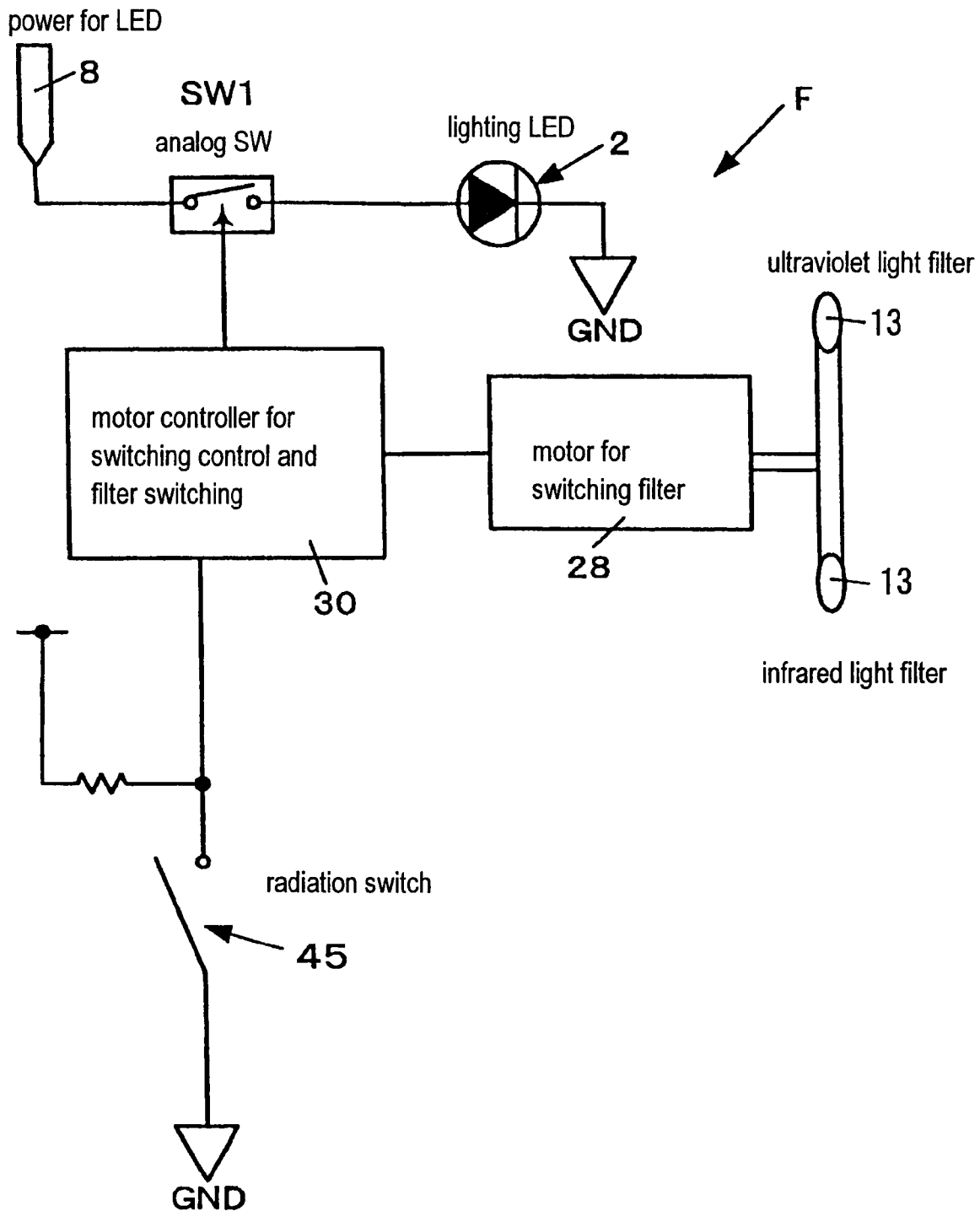
FIG. 17 is a control block diagram in which a light source and a filter are automatically set by operating a radiation switch.

FIG. 17 is a control diagram showing an embodiment in which the filter changing means F of FIG. 16 is used for switching the radiation filter. Filter switching signal by operating the filter switch 29 is controlled so as to be synchronous with the radiation signal of the luminous means 2. As shown in FIG. 17 a radiation switch 45 (functionally the same as the light source selection switches hs1-hs4 in FIG. 13) is manually turned on, an analog switch sw1 is turned on to put on the luminous means 2 like white LED and the motor 28 is driven in order that the radiation filter 13 comparable to the turned on luminous means 2 (comparable to the radiation switch 45) is selected and set to be switched into a desired radiation filter 13. In FIG. 17, one radiation switch 45 is provided and radiation of the luminous means 2 and the radiation filter 13 in response to the selectively operated radiation switch 45 are automatically selected and set. Such a switching control sequence is of course applied to switching of the light receiving filter. In this embodiment the white LED is used as the radiation source, however, a halogen lamp may be used in the same manner.

Figure 18:
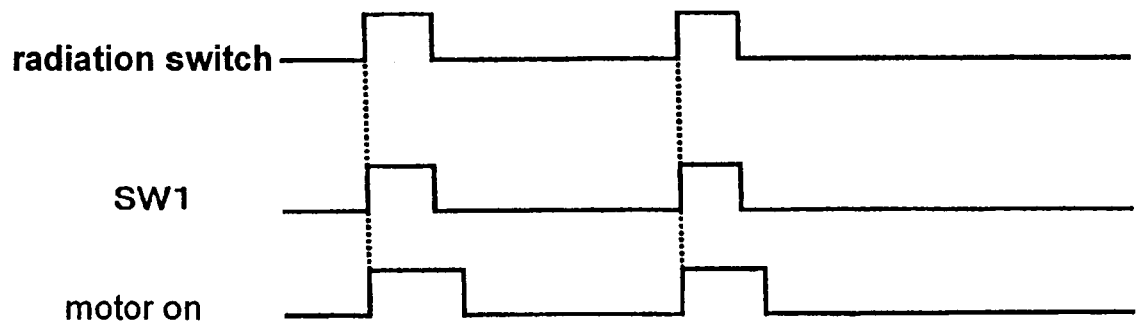
FIG. 18 is a synchronous time chart for selecting a light source and for switching a filter.

FIG. 18 shows a time chart of the radiation switch 45, the analog switch sw1, and the motor 28 by the filter changing means F of FIG. 17. It shows the analog switch sw1 is turned on in synchronous with the operation of the radiation switch 45, and accordingly the motor 28 is synchronously driven. Here the electric conduction time to the motor 28 is a little longer than ON time of the analog switch sw1 so that the switching operation of the radiation filter 13 (applicable to the light receiving filter) can be surely executed.

Embodiment 5

Figure 19A:
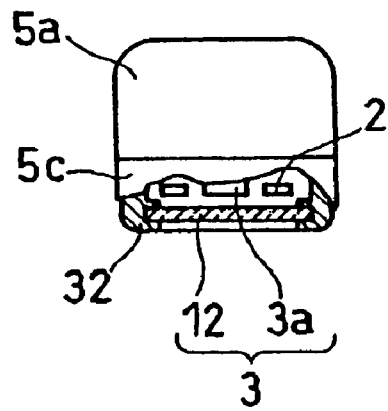
FIG. 19a is a partially cutaway front view of the forward portion.
Figure 19B:
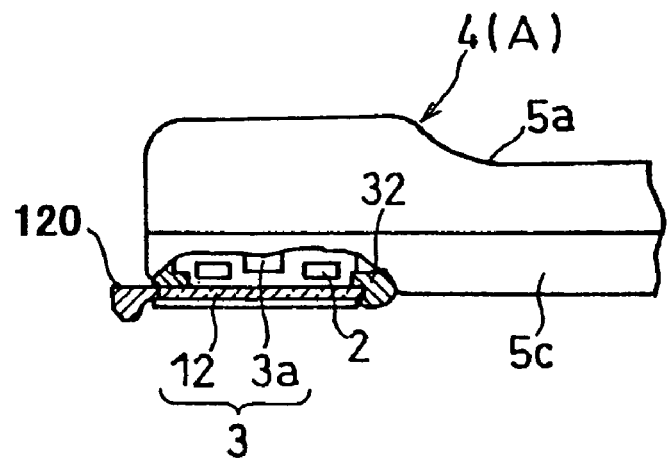
FIG. 19b is a partially cutaway side view.
Figure 19C:
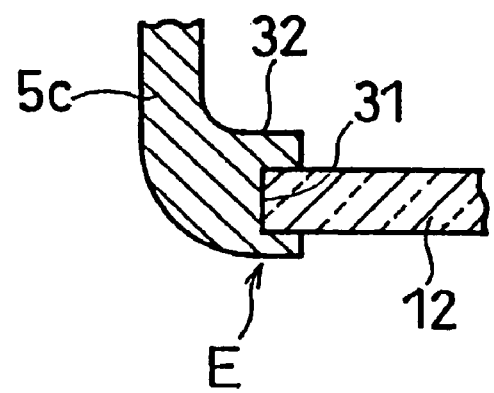
FIG. 19c is an enlarged view of a rail groove.

FIG. 19a, FIG. 19b, and FIG. 19c show one embodiment of a filter detachable means. According to the filter detachable means E in the figures the forward portion 4 is formed with a rail groove 31 for freely attaching and detaching a single light receiving filter 12 made of glass or plastic by slide operation. A pair of upheaval parts 32 are formed at the bottom of the forward case 5c (constituting a part of the forward portion 4) and the concave rail groove 31 for fitting the end of the plate-like light receiving filter 12 into each upheaval part 32 is provided. A finger grip 120 formed at the end of the light receiving filter 12 is pinched to be pushed into the rail groove 31 and to be pulled out of the groove 31, thereby the light receiving filter 12 becomes detachable from a light entrance opening of the forward portion 4.

By sliding the light receiving filter 12 along the longitudinal direction of the diagnostic imaging apparatus A, the light receiving filter 12 is attached to a predetermined position directly under the CCD 3a constituting the imaging means 3 or is removed from the forward portion 4. Accordingly the light receiving filter 12 is exchanged as a single unit or is freely exchanged with other different light receiving filter so that the light receiving filter 12 can be advantageously attached and detached with easy construction and at low cost while keeping the compactness of the forward portion 4. This filter detachable means E can be also applied to the radiation filter.

Embodiment 6

Figure 20A:
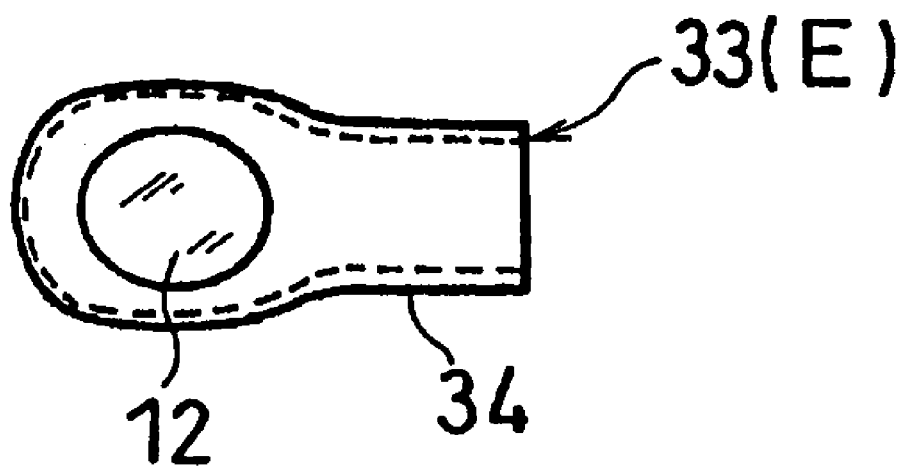
FIG. 20a is a bottom view of the cover.
Figure 20B:
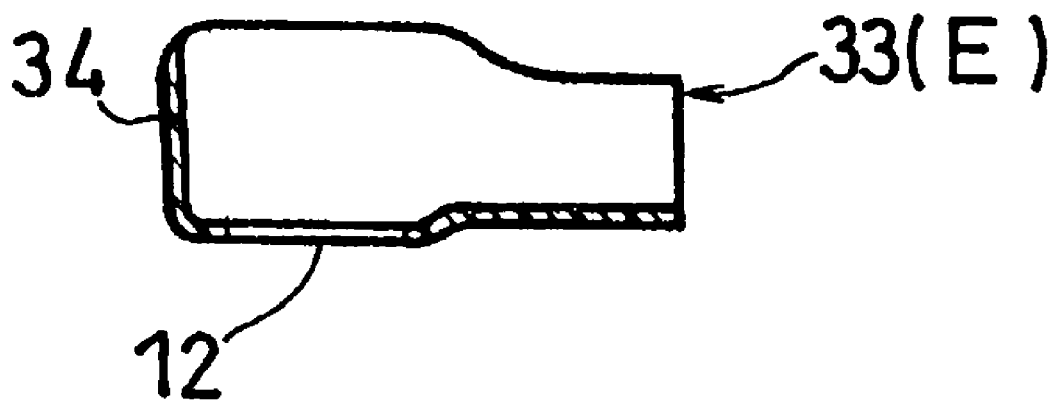
FIG. 20b is a sectional side view of the cover.

FIG. 20a and FIG. 20b show other embodiment of the filter detachable means. The filter detachable means E in the figures is comprised of a cover 33 like an open box having the light receiving filter 12 (applicable for the radiation filter). Namely, the cover 33 is comprised of a main body 34 made of synthetic resin formed so as to be fitted in the forward portion 4 shown in FIG. 27 FIG. 4 and the light receiving filter 12 to be attached to the body 34. In this case, the light receiving filter 12 may be provided directly under the CCD 3a constituting the imaging means 3 or may be removed from the forward portion 4. Therefore, the cover 33 may be called as an attachment constituting a part of the forward portion 4. Such constructed light receiving filter detachable mechanism and the selective radiation mechanism of the radiation light source as shown in the embodiment 2 are combined, thereby exerting effective manner.

Embodiment 7

Figure 21A:
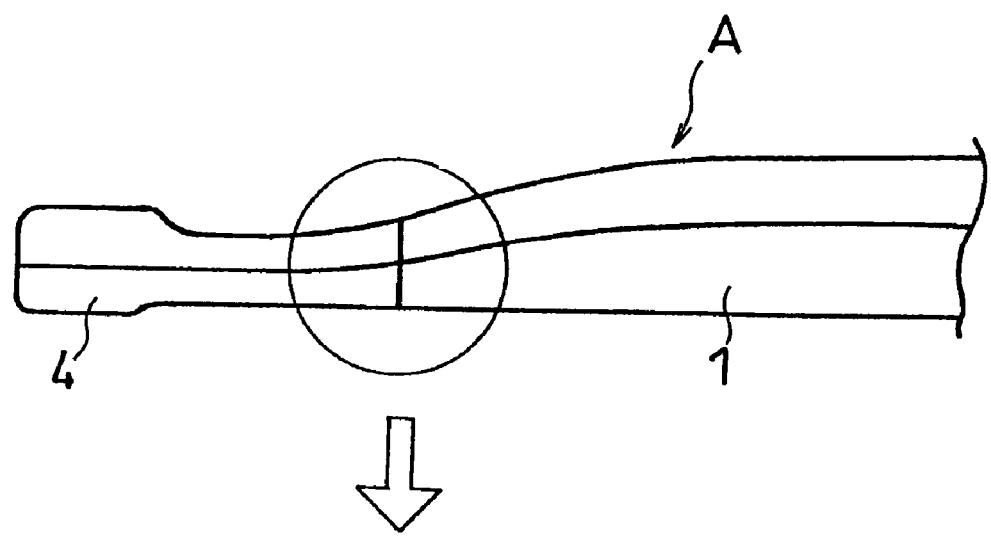
FIG. 21a is a side view of the forward portion of a diagnostic imaging apparatus.
Figure 21B:
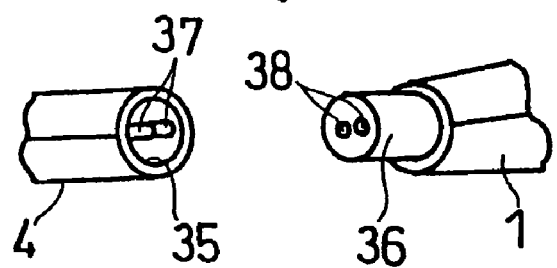
FIG. 21b is an exploded perspective view when the forward portion is separated.

FIG. 21a and FIG. 21b show the diagnostic imaging apparatus A of which the forward portion 4 is detachably constructed to the main body 1. Hollow fitting member 35 is formed at the root of the forward portion 4 and a projection member 36 internally fitted in the fitting member 35 is formed at the tip end of the main body 1. Plural male electrodes 37 are provided in the fitting member 35 and plural female electrodes 38 are correspondingly provided for the projection member 36.

Fitting the fitting member 35 and the projection member 36, the male electrode 37 and corresponding female electrode 38 are simultaneously connected and the forward portion 4 is attached to the main body 1 so that electric power can be supplied to the forward portion 4. When the fitting member 35 is removed from the projection member 36, the male electrode 37 and corresponding female electrode 38 are simultaneously disconnected so that the forward portion 4 is removed from the main body 1. According to such a construction, only the forward portion 4 can be replaced for one common main body 1 according to diagnostic purpose and diagnostic object, thereby achieving general purpose and convenience. Although it isn't shown in the figure, the forward portion 4 may be constructed so as to be separated into a head portion and a base portion so that an optical system such as a filter and a mirror, and a luminous means may be provided for the head portion and CCD may be provided for the base portion and the head portion may be exchanged in case of diagnosis.

Embodiment 8

Figure 22:
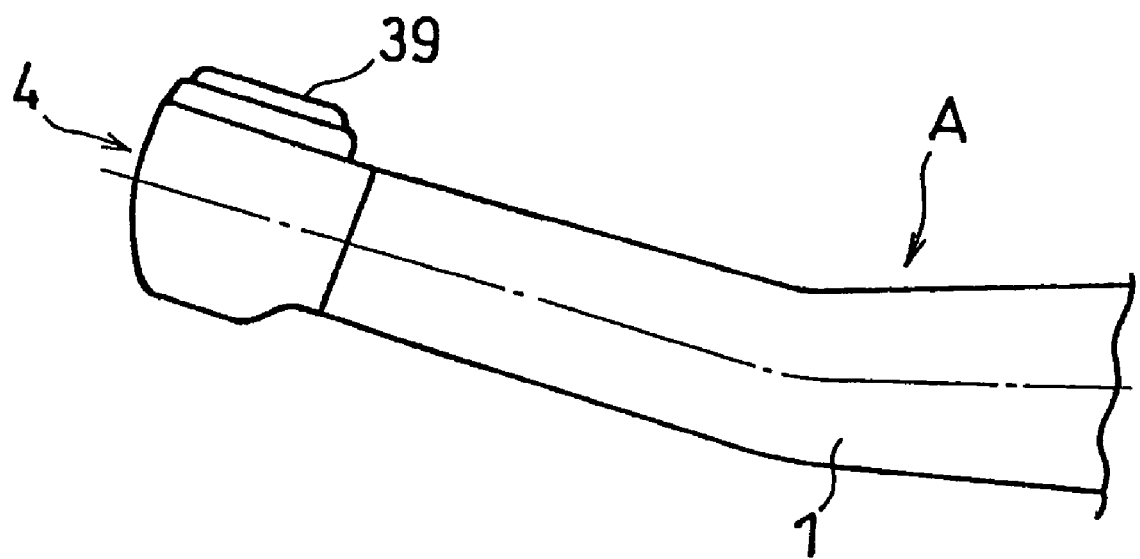
FIG. 22 is a side view showing another embodiment of a diagnostic imaging apparatus.

FIG. 22 shows one embodiment of the diagnostic imaging apparatus A and the main body 1 is formed like a dental contra-angle handpiece such that the forward portion 4 has a slight angle to the main body 1. CCD 3a as the imaging means 3 is provided in the center of a head portion 39, which is circular seen from the top, at the forward portion 4 and a lens (it is possible to be one embodiment of the light receiving filter 12) 3c is provided via a light guide (optical means) 3b at the lower end of the CCD 3a. Light emitting member 200 which is provided with LED (one embodiment of the luminous means 2) 2e so as to have a slight angle to the optical axis of the lens is provided for the main body side from the lens 3c. In this embodiment, CCD 3a, the light guide 3b and the lens 3c comprise the imaging means 3.

Figure 24A:
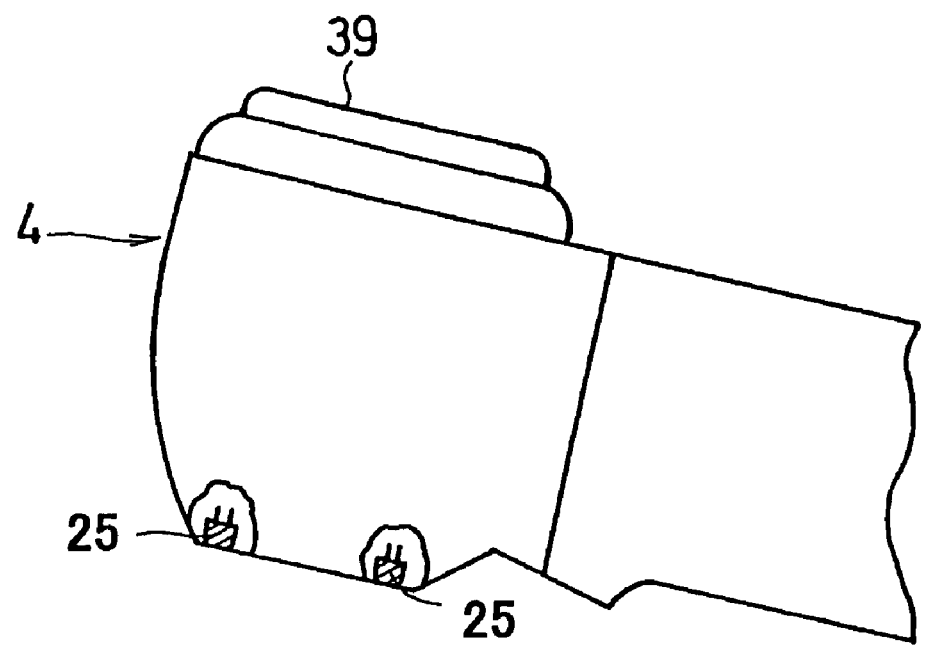
FIG. 24a is its side view.
Figure 24B:
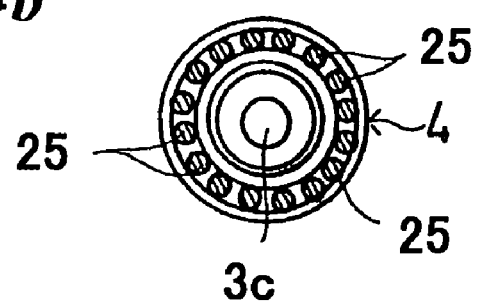
FIG. 24b is its partial bottom view.

LED (luminous means) 2e may be provided such that one long LED is provided as shown in FIG. 23b and two (or more than three) circular LEDs are arranged as shown in FIG. 23c. Otherwise, plural numbers of smaller LEDs (luminous means) 2f may be provided around the lens 3c serving as the light receiving member of the imaging means so as to surround the lens 3c as shown in FIG. 24a and FIG. 24b. In this case, it is preferable to provide several kinds of LEDs 2f such as infrared LED and blue LED and to be able to execute several turn-on conditions.

Embodiment 9

Figure 25:
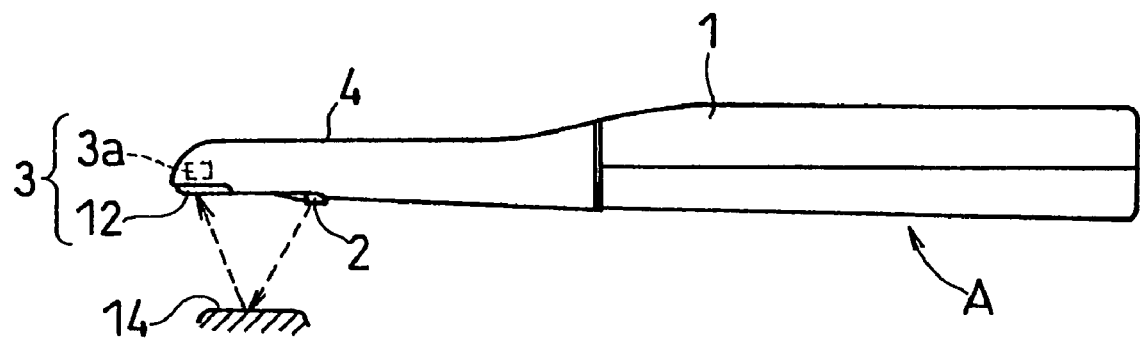
FIG. 25 is an entire side view showing other embodiment of a diagnostic imaging apparatus.

FIG. 25 shows other embodiment of the diagnostic imaging apparatus A which is designed such that the forward portion 4 isn't expanded than the root and is rather narrowed as shown in the figure. CCD 3a as the imaging means 3 is provided at the bottom end of the forward portion 4, contrary, the luminous means 2 is provided at the main body side and is provided with an angle against the optical path of the radiation light from the luminous means so as to enter the light reflected from the diagnostic object 14 to the light receiving filter 12.

Embodiment 10

Figure 26:
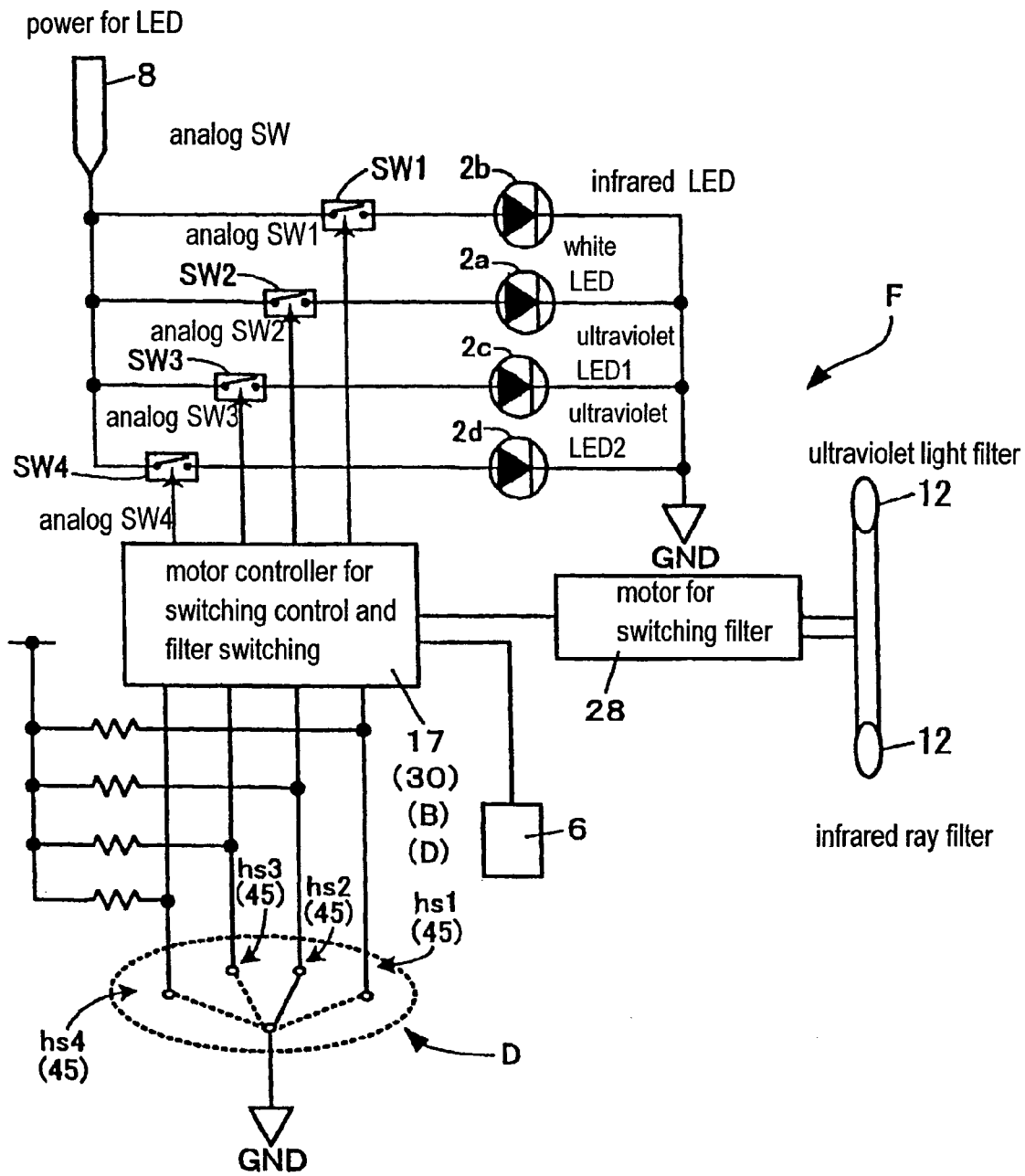
FIG. 26 is a control block diagram showing other embodiment of a switching construction of a radiation light source.

FIG. 26 shows another embodiment of the filter switching control sequence, filter switching signal is synchronous with the input signal of the luminous means selection means, and the filter changing means F is controlled so as to be switched to the light receiving filter 12 (applicable to radiation filter) corresponding to the selected luminous means. The filter changing means F is comprised of four light source selection switches hs1-hs4 (corresponding to the radiation switch 45 and the radiation light source selection means D), four analog switches sw1-sw4, a switching control means 30, a motor 28 for rotating and switching four light receiving filters 12.

For example, the second light source selection switch hs2 is manually operated, the second analog switch sw2 is turned on by electric control to turn on white LED 2a, and the motor 28 is driven to operate the switching control means so as to set a light receiving filter 12 suitable for the white LED 2a. In this embodiment, the light source selection switch sends the filter switching signal and the switching control means 30 is served as the radiation light source selection means D.

The diagnostic imaging apparatus A may be provided with an automatic photography control means C which sequentially stores the diagnostic images taken by the imaging means 3 in the memory 18 (see FIG. 2, FIG. 8 or FIG. 9) each time executing a predetermined time sequence by operating the photography switch 6 and selectively radiating the radiation light with different wavelength. For instance, in FIG. 26, the photography switch 6 connected to the switching control means 30 is provided for the main body 1, the control box H (see FIG. 2) or a foot pedal (not shown). The switching control means 30 is included in a switch controller or a filter switching motor controller 17 constructed with a microcomputer, however it may be provided independently.

When the photography switch 6 is turned on (or the main body 1 is stopped more than 2 seconds), switching control and photography sequence by the filter switching motor controller 17 (see FIG. 2, FIG. 8 or FIG. 9) are started. Specifically, the first analog switch sw1 is turned on according to ON operation of the photography switch 6, the motor 28 is driven to switch the light receiving filter 12 correspondingly, and after stopping the motor 28 (after the time t1 from ON operation of the first analog switch sw1) till OFF operation of the first analog switch sw1, the image formed by infrared LED 2b is stored in the memory 18 (as mentioned above).

Figure 27:
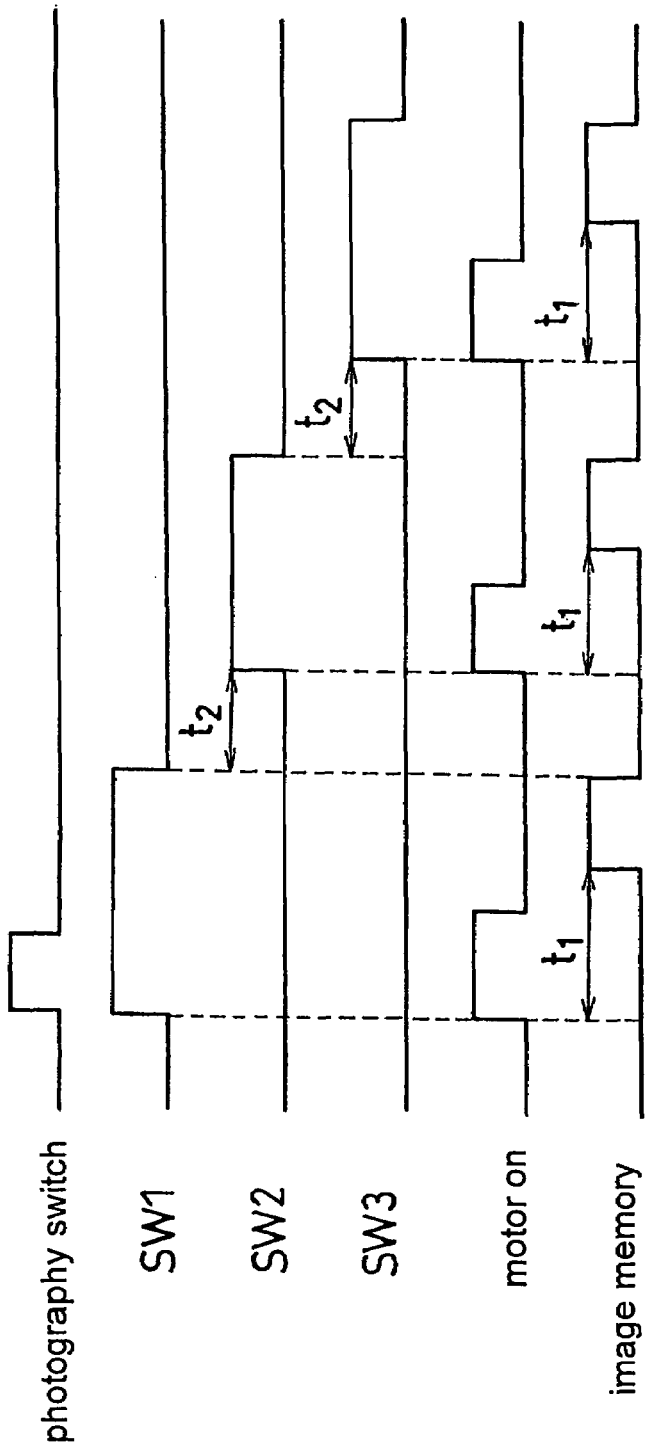
FIG. 27 is a time chart of photography sequence following photography switch operation.

After the time t2 from the first analog switch sw1 is turned off, ON operation of the analog switch sw2 is started and the image taken by white LED 2a is stored in the memory 18 in the same manner. Thereafter, the image obtained by ultraviolet LED 1 (2c), the image obtained by ultraviolet LED 2 (2d) are sequentially taken in the same manner. In FIG. 27 explanation of the fourth analog switch sw4 is omitted for easy understanding.

The diagnostic imaging apparatus A may be constructed such that the filter switching signal is synchronous with radiation of the radiation light source selected by the photography sequence from the radiation light source which is predetermined in advance according to the input signal of the photography switch 6 and the light receiving filter is switched into the one corresponding to radiation of the radiation light source corresponding to the photography sequence. For example, the apparatus A is provided with a mechanism (not shown) in which one of the four light source selection switches hs1-hs4 in FIG. 26 is automatically and sequentially turned on (a mechanism in which four switches are sequentially switched by an electric motor), and the photography switch 6 connected to the switching control means 30 (see FIG. 16) is provided for the main body 1 (see FIG. 2), the control box H (see FIG. 2) or the foot pedal (not shown).

Figure 28:
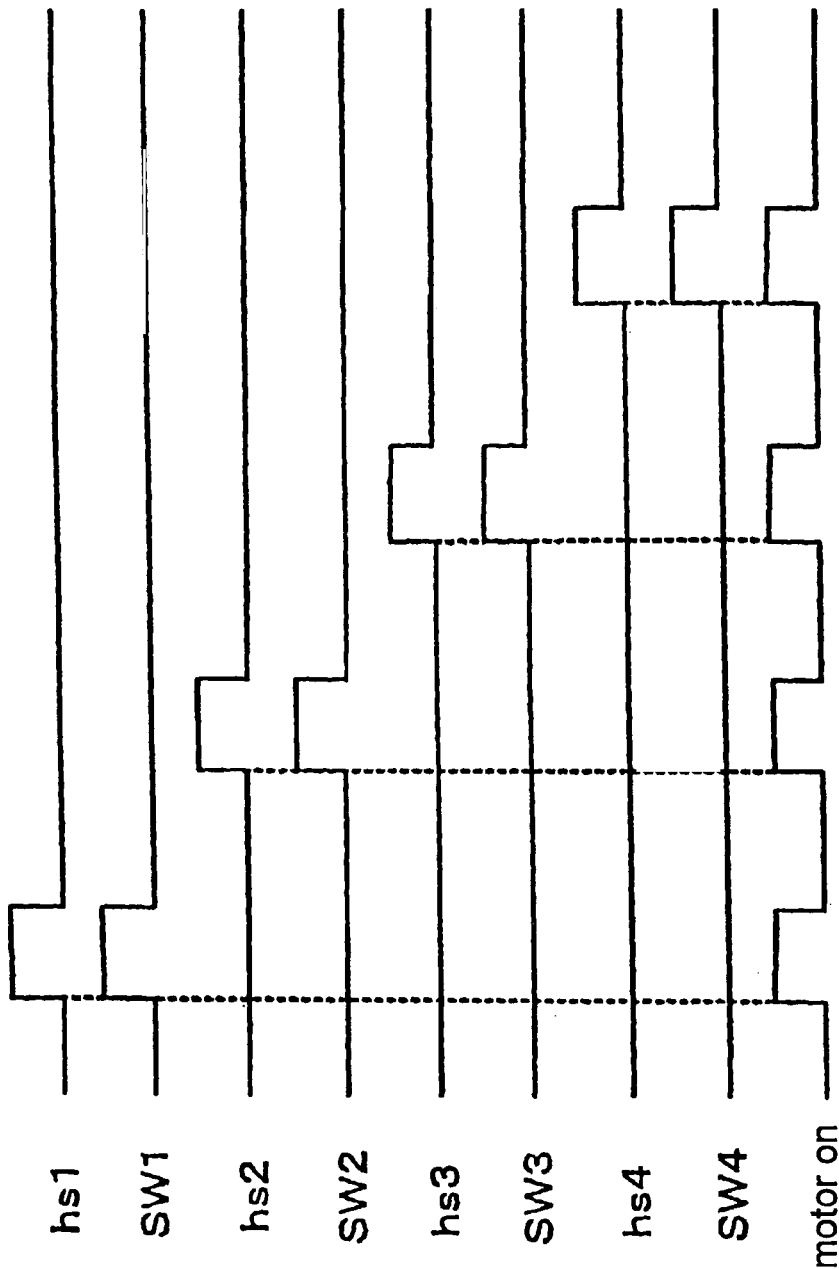
FIG. 28 is a synchronous time chart for selecting plural light sources and for switching plural filters.

Now, photography operation according to the diagnostic imaging apparatus A is explained. The microcomputer 17 is operated when the photography switch 6 is turned on, and the light source selection switches hs1-hs4 are under automatic control condition so as to be sequentially turned on at a fixed time interval as shown in FIG. 28. Namely, when the first light source selection switch hs1 is turned on at first, the light receiving filter 12 is switched into the one for infrared LED 2b and the first analog switch sw1 is conducted to become radiation photography by the infrared LED 2b, then radiation photography by white LED 2a, radiation photography by ultraviolet LED 1 (2c), and radiation photography by ultraviolet LED 2 (2d), thus achieving automatic drive mode repeating them in this order. The images taken in the memory 18 are those sequentially taken by the imaging means 3 by means of the four kinds of radiation light emitting members 2a-2d. The image obtained by executing image processing between those images is displayed on the monitor M.

The filter is thus switched automatically by the motor according to the filter switching signal, thereby reducing the labor and time for exchanging a filter and achieving rapid diagnostic operation. Further, because filter switching is controlled in synchronous with the radiation signal from the radiation light source, switching of the radiation from the luminous means 2 and switching of the light receiving filter 12 are executed at one time, not separately, thereby simplifying the operations. Still further, even when the relative angle and position of the diagnostic object and the light receiving member of the imaging means 3 are diversely changed, the light from the luminous means 2 is accurately radiated on the diagnostic object and the reflected light is surely inputted in the imaging means 3 without causing shade. Consequently, the imaging means and the luminous means are compactly provided at the forward portion of the main body and photography can be executed in any conditions, thereby improving the diagnostic reliability.

The luminous means 2 includes plural numbers of light emitting members generating light with different wavelength respectively. Therefore, the image information of the diagnostic object can be obtained by selecting and radiating one of the light emitting members (including light source of white light) with an optional wavelength (basic usage), in addition, by radiating lights with different wavelength at one time (simultaneous radiation), or by radiating the light with different wavelength sequentially in time division. Further, there exists no labor or trouble for exchanging the light emitting members and it is available that desired light emitting members 2a-2d are freely selected. Moreover, when the luminous means 2 corresponding to the diagnostic purpose is prepared, plural images such as fluorescence image and infrared light image can be obtained at the same photography position. Therefore, plural images taken at the same photography position using different light emitting members or different light receiving filters 12 can be easily displayed in parallel or in overlapped. Selection of the above-mentioned light emitting members 2a-2d is done by the switches and thereafter the light receiving filter 12 is designed to be exchanged.

Here the light emitting members 2a-2d emitting light with different wavelength indicate LED which emits light with different wavelength, in addition, LED with different function (wavelength) like infrared LED 2b or ultraviolet LED 2c, 2b. Because different kinds of lighting functions are mounted thereon, LED can radiate at the same time or can radiate in time division. Hereby, in case of moving image, not static image, different kinds of images can be automatically switched and displayed by the radiation light from the light emitting member.

If it is constructed such that radiation drive for selectively operating plural light emitting members 2a-2d is executed by way of time division control, the error is easily cancelled and the condition of the lesioned part is easily understood by obtaining the difference between the images per time, by obtaining the average and by overlapping the images, thereby producing a more accurate image. Further, time division control is executed in a very short time interval, image processing is executed so as to connect these time division images suitably, and the processed image is displayed on a monitor. Thus an image like an animation can be obtained, resulting an image data capable of showing a patient for easy explanation.

Further, not only the light receiving filter 12 and the radiation light sources 2a-2d can be switched at one time, but also the light receiving filter 12 and the luminous means 2 can be correspondingly switched into a suitable one prepared in advance. Therefore, photography time is reduced and its operability is highly improved. By reducing photography time, images without blur can be obtained during image processing. If it requires during diagnosing, a static image of the diagnostic object to be photographed is easily recorded and stored by means of the image storage means 18. Moreover, if a light source selection switch D provided for the main body 1, the control box H, or the foot pedal (not shown) is included as the radiation drive means, manual operation supporting the main body 1 of the imaging apparatus, operation at the control box H, or footfall operation of the foot pedal make the light source selection switch D operated, then the luminous means 2 can be switched, thereby achieving superior operability.

In addition, by operating the photography switch 6, diagnostic images with different characteristics are automatically obtained so that different image information with diagnostic value can be obtained in a short time which isn't affected by hand blurring. If an arithmetic processing is executed between these images, the characteristic of the lesioned part is easily taken out and image without blurring can be obtained. Each time the content of the obtained image is changed, the static image can be recorded and stored by the image storage means. Further, each time an image with different content is obtained, the static image can be overwritten. For example, when infrared LED and ultraviolet LED are provided, a mechanism for obtaining at least two static images corresponding to each exciting light is provided and the static image is overwritten every time being switched to each sequence.

When white LED and ultraviolet LED are provided, a normal reflected image by the white LED and the fluorescence image excited by the ultraviolet LED can be obtained as a static image, then the obtained image can be processed by the image processing means. Namely, a normal reflected image (visible light image) is obtained by selecting white LED for explaining to a patient, the luminous means is changed to the ultraviolet LED for confirming the lesioned part, and the corresponding light receiving filter is provided for the light receiving member of the imaging means, thus easily obtaining the diagnostic image information. Of course both images may be displayed at the same time.

In addition to that switching of radiation from the luminous means 2 and the filter 12 is executed at one time, the kind of filter 12 can be automatically and sequentially switched for photography corresponding to the kinds of the luminous means 2 prepared in advance, thereby it is convenient that the photography time is reduced and its operation becomes improved. For example, white LED is radiated to the diagnostic object, the reflected image is obtained to be stored by the imaging means via a glass which passes the light in a visible range as a filter, at the next moment, fluorescent image generated from the diagnostic object by radiating exciting light is obtained to be stored via a dedicated light receiving filter 12. If such a combination is automatically executed 20 times per second, a normal image is shown on the left side of the monitor and the fluorescence image is shown on the right side, both images are overlapped, or further only the lesioned part of the fluorescence image is cut off to be overlapped on the normal image, thereby obtaining a valuable image for diagnosis purpose.

Still further, the diagnostic imaging apparatus A may be constructed to be used as a photo polymerization radiator with blue LED as a luminous means. According to such an apparatus A, blue LED (light emitting diode) is added to the radiation light emitting member so that the apparatus can be used not only as a diagnostic imaging apparatus but also as a photo polymerization radiator for hardening a photo polymerization resin charged in a tooth, thereby realizing a convenient and excellent apparatus which has a photography function and a treatment function. Hereby, while executing diagnostic photography, an operator can keep the above-mentioned hardening treatment with the same apparatus without exchanging the apparatus.

Embodiment 11

Figure 29A:
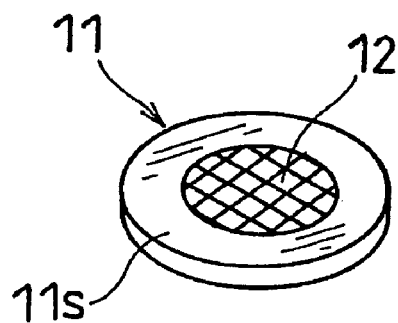
FIG. 29a and FIG. 29b are perspective views showing a typical embodiment of a light receiving filter.
Figure 29B:
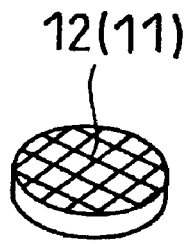
Figure 30A:
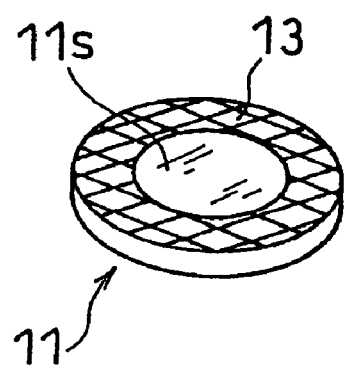
FIG. 30a and FIG. 30b are perspective views showing a typical embodiment of a light source filter.
Figure 30B:
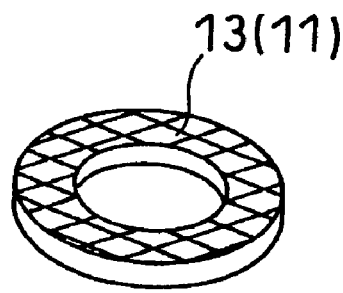
Figure 31A:
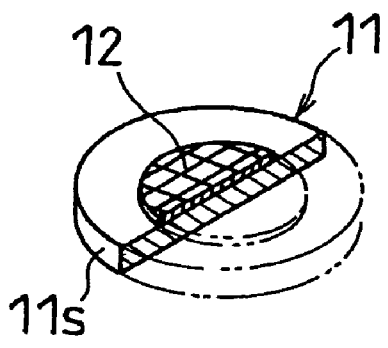
FIG. 31a is a perspective view showing a coated light receiving filter and FIG. 31b is a perspective view showing a coated light source filter.
Figure 31B:
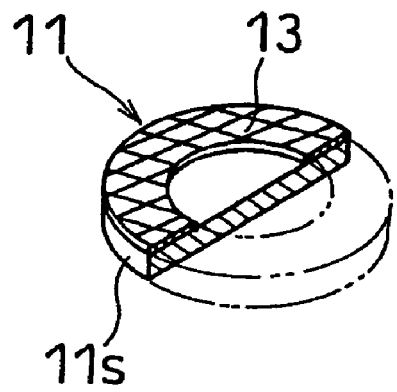

Several kinds of filters are explained referring to FIG. 29a, FIG. 29b, FIG. 30a, FIG. 30b, FIG. 31a, and FIG. 31b. FIG. 29a shows a disc like filter 11 constructed such that a ring-like part near the radiation light source (directly thereunder) is a support member 11s made of clear glass or synthetic resin and the center around the imaging means (directly thereunder) is formed as a light receiving filter 12. As shown in FIG. 29b, a filter 11 may be formed only with the light receiving filter 12. One embodiment of the radiation filter 13 is shown in FIG. 30a in which the center near the imaging means (directly thereunder) is formed as a support member 11s made of clear glass or synthetic resin and the outer ring-like member near the radiation light source provided at its circumference is formed as a radiation filter 13. As shown in FIG. 30b, a filter 11 may be formed only with a ring-like radiation filter 13. Otherwise, as shown in FIG. 31a, a light receiving filter 12 may be formed such that the filter member is coated on the surface of the center of the disc like support member 11s. Or as shown in FIG. 31b, a radiation filter 13 may be formed such that a filter member is coated on the ring-like surface of the circumference of the disc-like support member 11s. Further, the coated light receiving filter 12 and a coated radiation filter 13 as shown in FIG. 31a and FIG. 31b may be compound and formed on one disc-like support member 11s.

Embodiment 12

Figure 32:
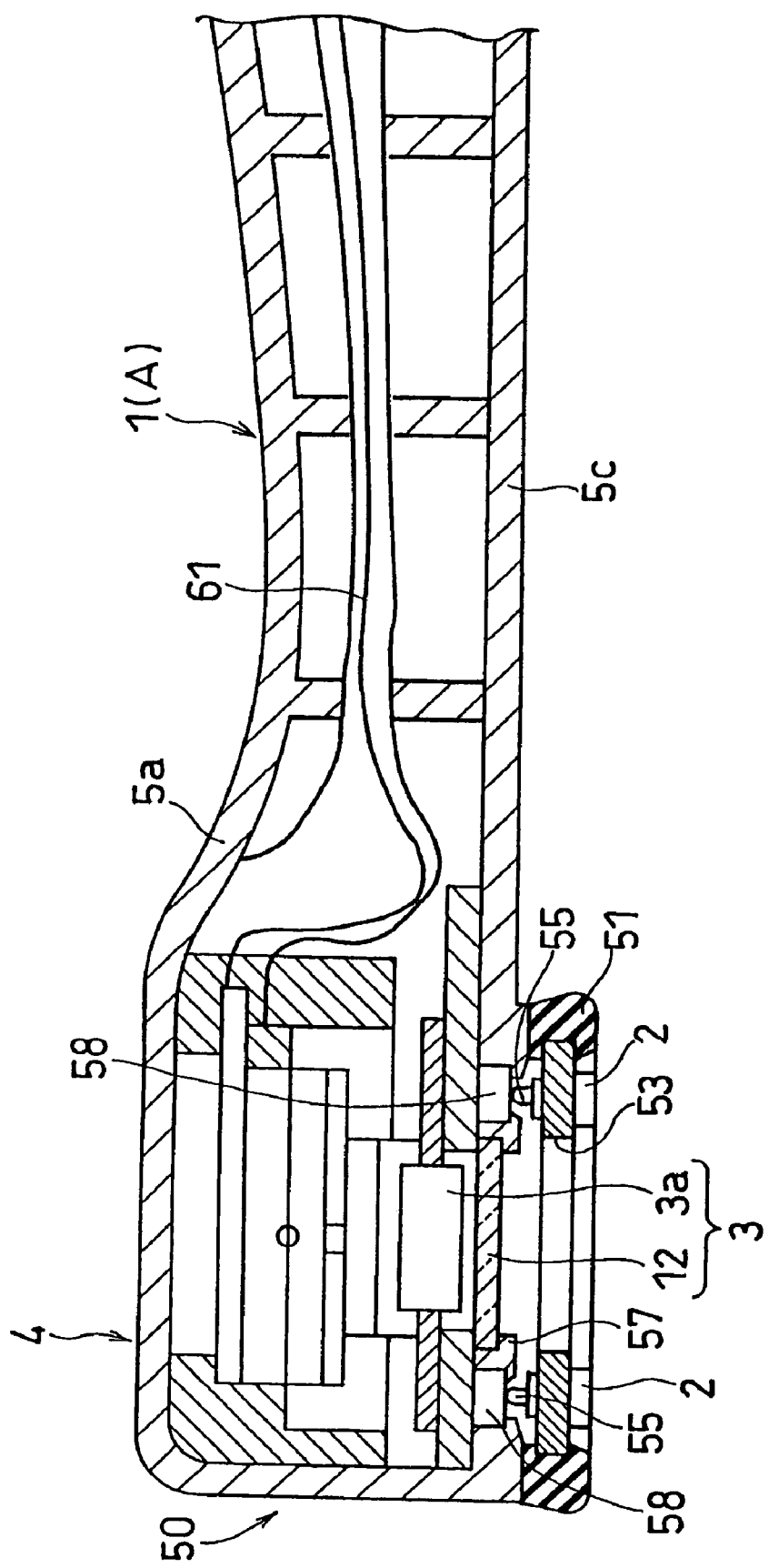
FIG. 32 is a sectional view of a photography member of which luminous means id detachable.

FIG. 32 shows one embodiment in which a luminous means is detachable. The diagnostic radiography apparatus A is constructed such that a photography member 50 for imaging a photography object is provided for the main body 1 supportable by hands and fingers, the photography member 50 is provided with the luminous means 2 for irradiating light on the object, the CCD 3a as an imaging means 3 and the light receiving filter 12 (constituting an imaging means 3) for passing only the light with specific wavelength to transmit to the CCD 3a, and the luminous means 2 is detachably provided for the photography member 50.

The forward case 5c has an annular receiving part 57 supporting the light receiving filter 12 directly under the CCD 3a and has a pair of receiving electrodes 58 around the receiving part 57 in a concaved manner. Annular supporting member 53 with a pair of convex electrodes 55 electrically contacting with these receiving electrodes 58 is detachably fitted to an annular attachment member 51 of which the rubber inner diameter fixed to the forward case 5c is elastic. Plural numbers of LEDs (luminous means) 2 conductively connected to a pair of concave electrodes are provided under the annular support member 53. The reference numeral 61 shows a lead wire for the luminous means 2 or the CCD 3a.

Accordingly, when the support member 53 is fitted to the annular attachment member 51, each convex electrode 55 contacts with the corresponding receiving electrode 58 to be electrically conducted. When the support member 53 is taken out of the annular attachment member 51, each convex electrode 55 and the corresponding receiving electrode 58 are disconnected. Therefore, if several kinds of support members 53 provided with LED 2 with different color or other luminous means 2 are prepared in advance, the luminous means 2 may be easily modified into other specification by exchanging the support member 53. Although in this embodiment the light receiving filter 12 is supported, it goes without saying that such a support mechanism can be used for the radiation filter.

Embodiment 13

Figure 33:
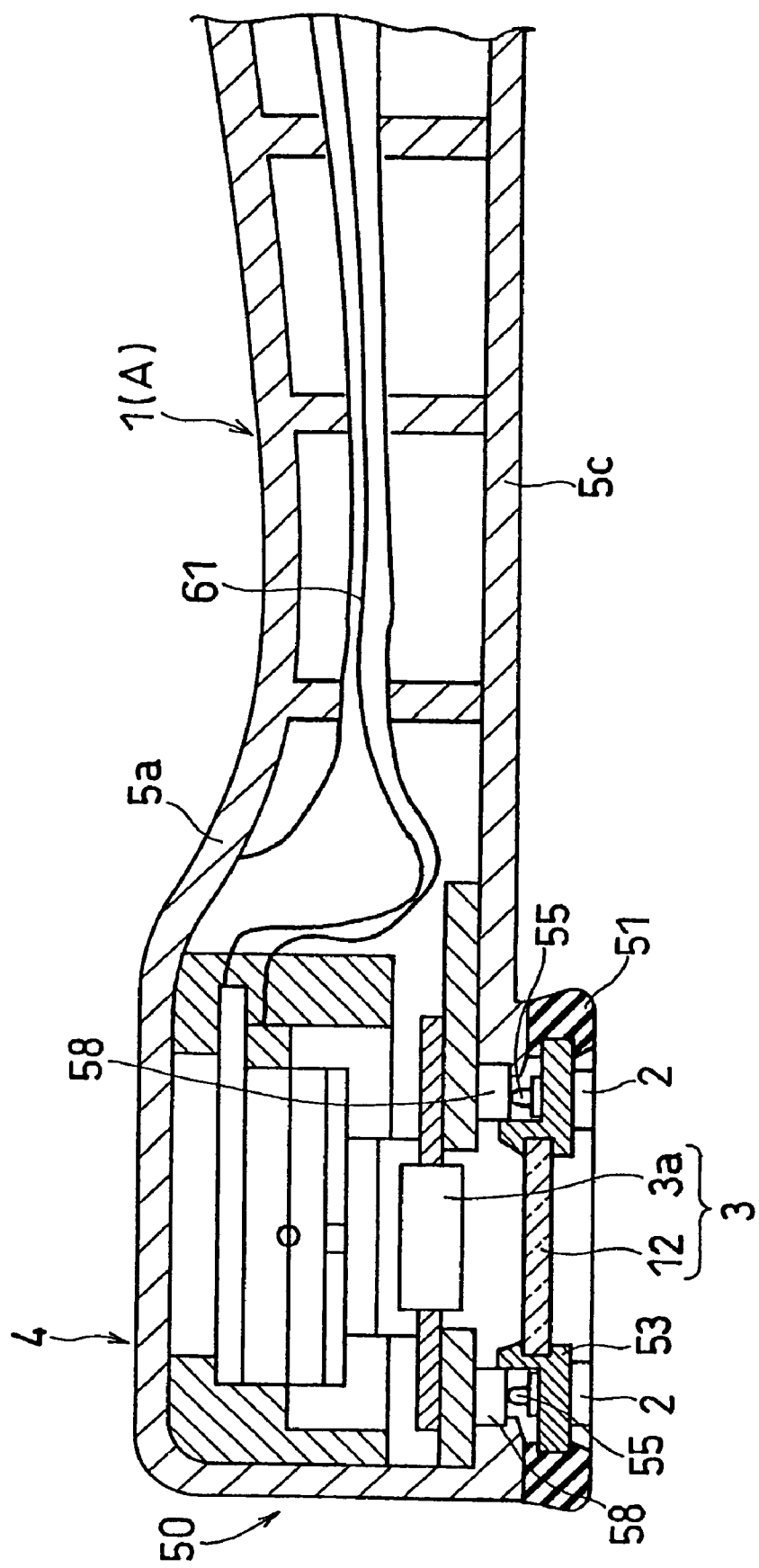
FIG. 33 is a sectional view of a photography member constructed such that a luminous means and a filter are integrated and detachable.

FIG. 33 shows an embodiment in which a luminous means and a filter are integrated to be detachable. The diagnostic imaging apparatus A in the figure is constructed such that the luminous means (LED) 2 and a light receiving filter 12 are integrated to be detachably provided for the photography member 50. This embodiment includes a construction the light receiving filter 12 is detachably provided for the photography member 50. The construction in FIG. 33 is basically the same as that shown in FIG. 32, but is different in that the shape of the support member 53 is changed so as to support both the luminous means 2 and the light receiving filter 12. Other construction is the same as that in FIG. 32, the common members have the same reference numerals and their explanations are omitted here. The support material 53 may be made of rubber and the light receiving filter 12 may be detachably provided for the support member 53. This supporting mechanism is of course applied to the radiation filter.

The diagnostic imaging apparatus A shown in FIG. 33 is designed such that the luminous means 2 and the light receiving filter 12 are attached to the photography member 50 when the supporting member 53 is attached to the annular attachment member 51 and the luminous means 2 and the light receiving filter 12 are removed from the photography member 50 when the support member 53 is removed from the annular attachment member 51. The luminous means 2 for irradiating light on the diagnostic object, the CCD 3a as the imaging means 3, and the light receiving filter 12 for passing only the light with specific wavelength to be transmitted to the CCD 3a are provided for the main body 1 supportable with fingers and the luminous means 2 is detachably provided for the main body 1 together with the light receiving filter 12 (constituting a part of the imaging means 3).

According to such a construction, the light receiving filter 12 is easily exchanged and its specification is easily modified by attaching and detaching the support member 53. In addition, LED 2 (namely luminous means 2) can be modified into any specification so that diagnosis using the light with different wavelength is possible, thereby achieving more convenient and available diagnostic imaging apparatus A.

Embodiment 14

Figure 34:
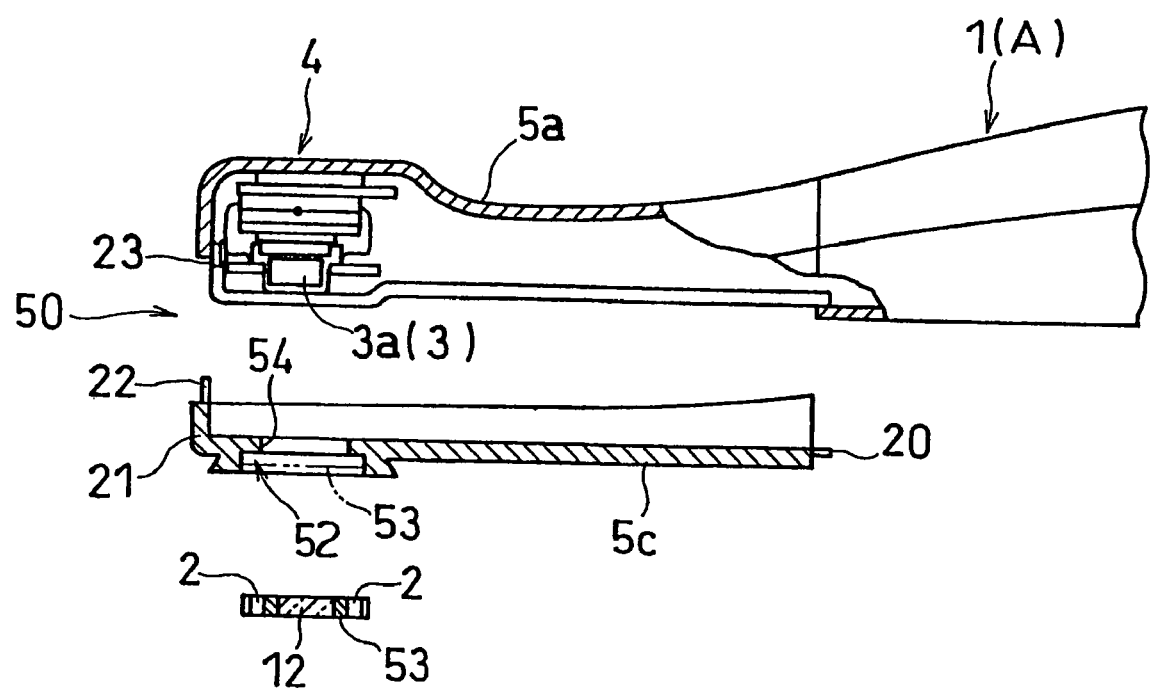
FIG. 34 is a sectional view of other photography member constructed such that a luminous means and a filter are integrated and detachable.

FIG. 34 shows a diagnostic imaging apparatus provided with a modified embodiment of the forward case shown in FIG. 5. The diagnostic imaging apparatus A in the figure is constructed such that an opening 54 which is a light introduction path to the CCD 3a (constituting an imaging means 3) and an annular stepped opening 52 formed around the opening 54 are provided for the forward case 5c (detachable attachment being a part of the forward portion 4). Further the supporting member 53 provided with the light receiving filter 12 (constituting a part of the imaging means 3) and plural LEDs (luminous means) 2 formed around the filter 12 is detachably provided for the stepped opening 52 from the forward case 5c. A pair of terminal electrodes for LED 2 are provided at the periphery of the support member 53 and the inner circumference of the stepped opening 52, not shown in the figure, so that both electrodes are connected to be conducted by attaching the support member 53 and they are disconnected by removing the supporting member 53. As other construction is the same as that shown in FIG. 5, the common members have the same reference numeral and their explanations are omitted here.

Embodiment 15

Figure 35:
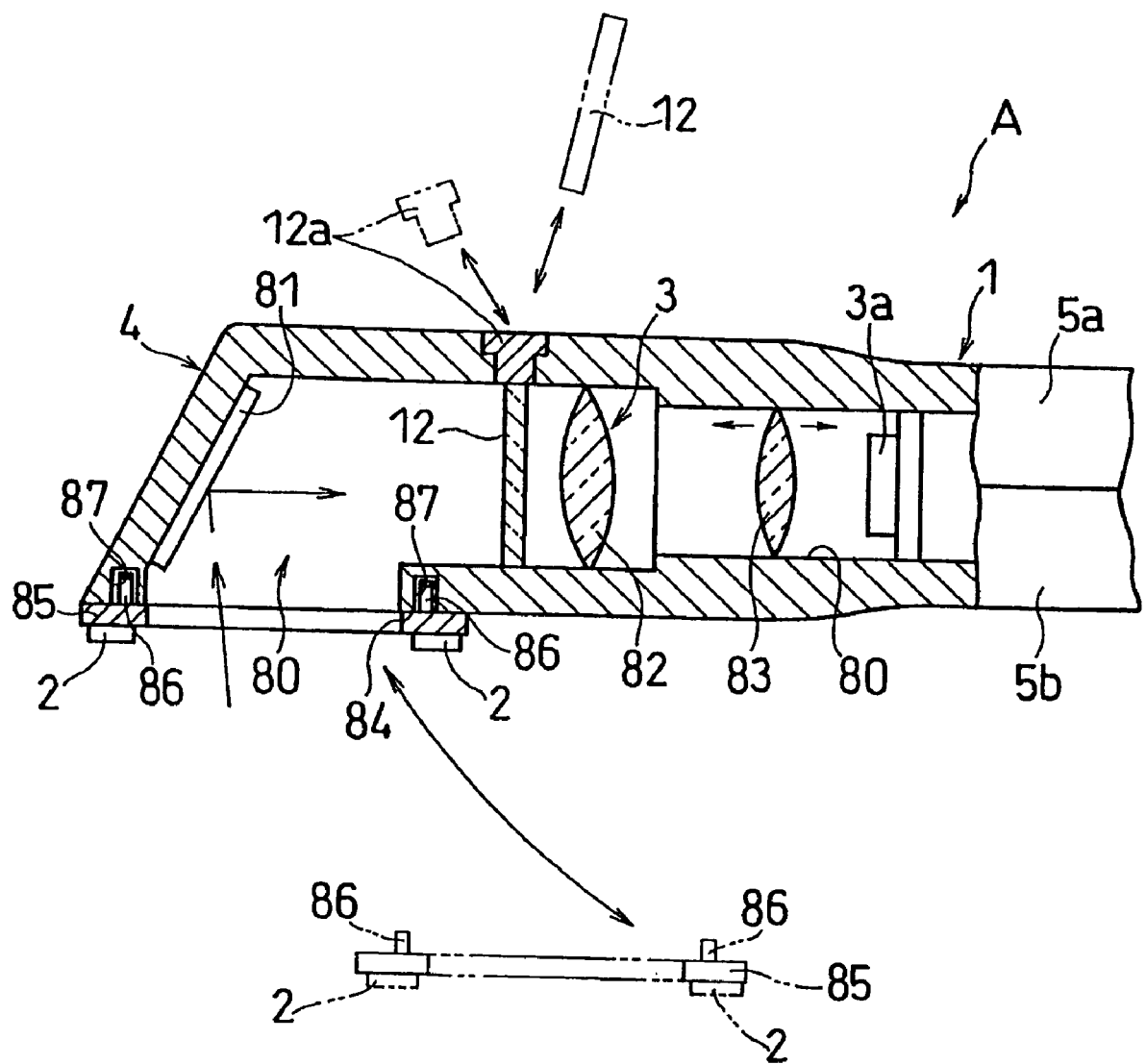
FIG. 35 is a partially cutaway vertical partial section of a diagnostic imaging apparatus using a optical path changing means.
Figure 36:
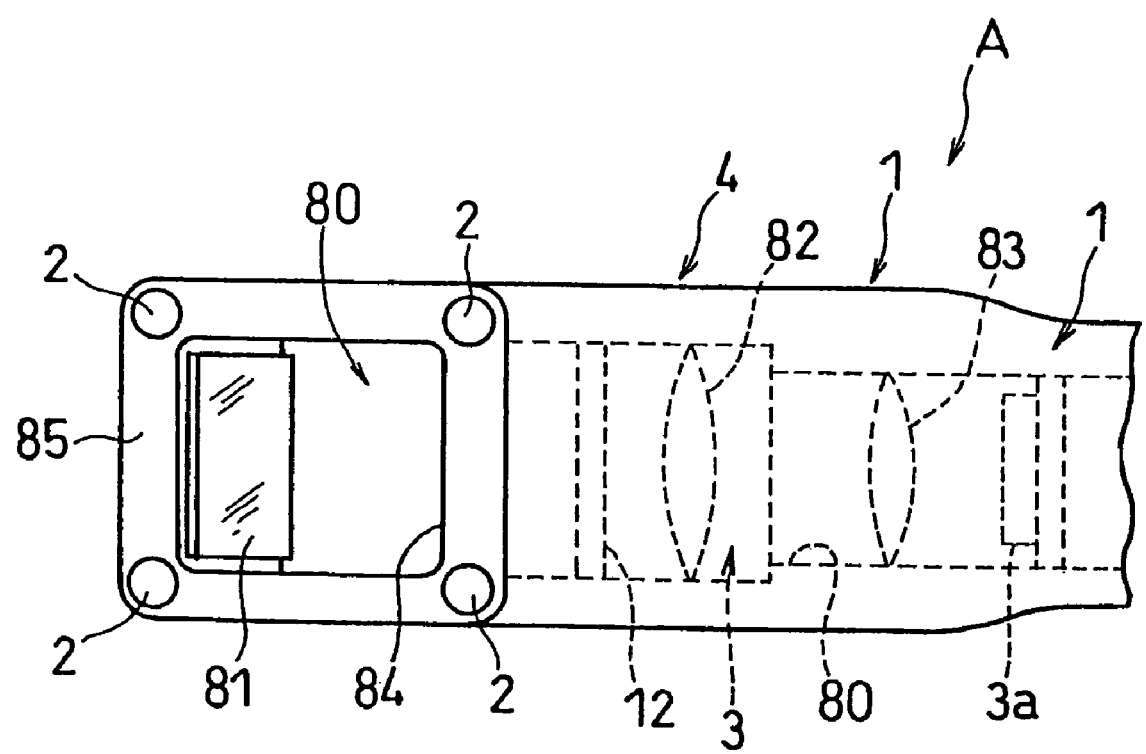
FIG. 36 is a bottom view of the diagnostic imaging apparatus of FIG. 35.

FIG. 35 is a partially cutaway partial vertical section of the embodiment provided with a optical path changing means for the imaging means and FIG. 36 is its bottom view. The diagnostic imaging apparatus A in the figure is designed such that the CCD 3a as the imaging means 3 is provided in the forward portion 4 of the main body 1 in such a manner the optical axis of the CCD 3a is along the longitudinal direction of the main body 1. Further, a mirror (or prism) 81 is provided as the optical path changing means inside of the forward portion 4 so as to have about 45 degrees against the optical axis and a cylindrical part between the mirror 81 and the CCD 3a is formed as a light introduction path 80 of an imaging light. A relay lens 82 and a relay lens 83 which is movable along the optical axis are provided for the light introduction path 80 and an optical system for forming an optical image on the CCD 3a is constructed with the mirror 81, the relay lens 82 and 83. The CCD 3a and the optical system constitute the imaging means 3.

The light receiving filter 12 is detachably provided around the front side (tip end side) of the relay lens 82 which is in midstream of the tubular forward portion 4. The reference numeral 12a is a cap for preventing the light receiving filter 12 from escaping. Therefore, if the light receiving filters with different wavelength characteristics are prepared, a suitable filter for diagnosis purpose can be easily exchanged. If a moving mechanism along the optical axis direction is further provided for the relay lens 83, a zoom mechanism is achieved. The relay lenses 82 and 83 are shown as convex lens, however, they aren't limited to a convex lens. It goes without saying that any lens capable of transmitting an optical image can be used.

An opening 84 for entering light which is opened into a direction substantially perpendicular to the optical axis is formed at the forward portion 4 in such a manner that the opening 84 and the light introduction path 80 are communicated. An annular support member 85 provided with plural numbers (4 in the figure) of LEDs (luminous means) 2 with space in a circumferential direction is detachably provided around the opening 84. Male receiving electrode 86 corresponding to each one of LEDs 2 is formed at the back of the annular support member 85. When the annular support member 85 is attached to the forward portion 4, the electrode 86 is designed to be electrically connected to a female supply electrode 87 formed at the forward portion 4. Plural LEDs 2 are constructed with a combination of plural kinds of LEDs emitting light with different wavelength as mentioned above so that diversified diagnostic image information can be obtained by activation and emission control base portion on the time sequence. Of course, any one of the plural LEDs 2 may be selectively irradiated and the light receiving filter 12 with the wavelength characteristic corresponding to the selected LED 2 may be selectively attached. The fitting and connecting relation of the female electrode 86 and the male electrode 87 constructs a detachable mechanism of the annular support member 85 and the luminous means 2 can be attached with one touch operation. If another annular support member 85 provided with different kinds of LEDs 2 is prepared, more multiphase diagnostic image information can be obtained by selectively changing the support member 85.

Accordingly, the light from the luminous means 2 is radiated on the diagnostic object member such as teeth and the reflected light or the fluorescence light is emitted from the diagnostic object member corresponding to the wavelength characteristic of the diagnostic object member base portion on the kinds of the luminous means 2. The optical image light base portion on the emission enters in the forward portion 4 from the opening 84, is reflected at about 90 degrees by the mirror 81, transmits the light receiving filter 12, is collected by the relay lenses 82, 83 while proceeding in the light introduction path 80, and is formed as an image at CCD 3a. The attaching position of the light receiving filter 12 isn't limited to the place shown in the figure and may be any position on the light introduction path 80. It goes without saying that other connection means can be employed as a substitute for the male and female electrodes 86, 87 by separately providing a wire connection means for the luminous means 2. Further, the mirror (optical path changing means) 81 as an optical means is provided for the annular support material 85 so that the LED 2 and the mirror 81 may be integrally detachable to the opening 84 via the annular support material 85.

According to the above-mentioned diagnostic imaging apparatus A, for obtaining a normal visible light image, white LED is used as a radiation light source 2 and a light receiving filter 12 isn't provided. For photographing dental calculus and dental plaque, the luminous means 2 is set to emit the light with wavelength of 375±25 nm and the light receiving filter 12 is set to pass the light with wavelength of above 430 nm. If exciting light is irradiated from the luminous means 2 and the fluorescence image is desired to be obtained on CCD 3a, the filter which cuts off the irradiated exciting light is used as a light receiving filter 12 so as to avoid the affection of the exciting light, as mentioned above. For photo polymerization, the luminous means 2 is for example set to emit light with 480±20 nm wavelength. In this case, the light receiving filter isn't required because the light isn't received.

Figure 37:
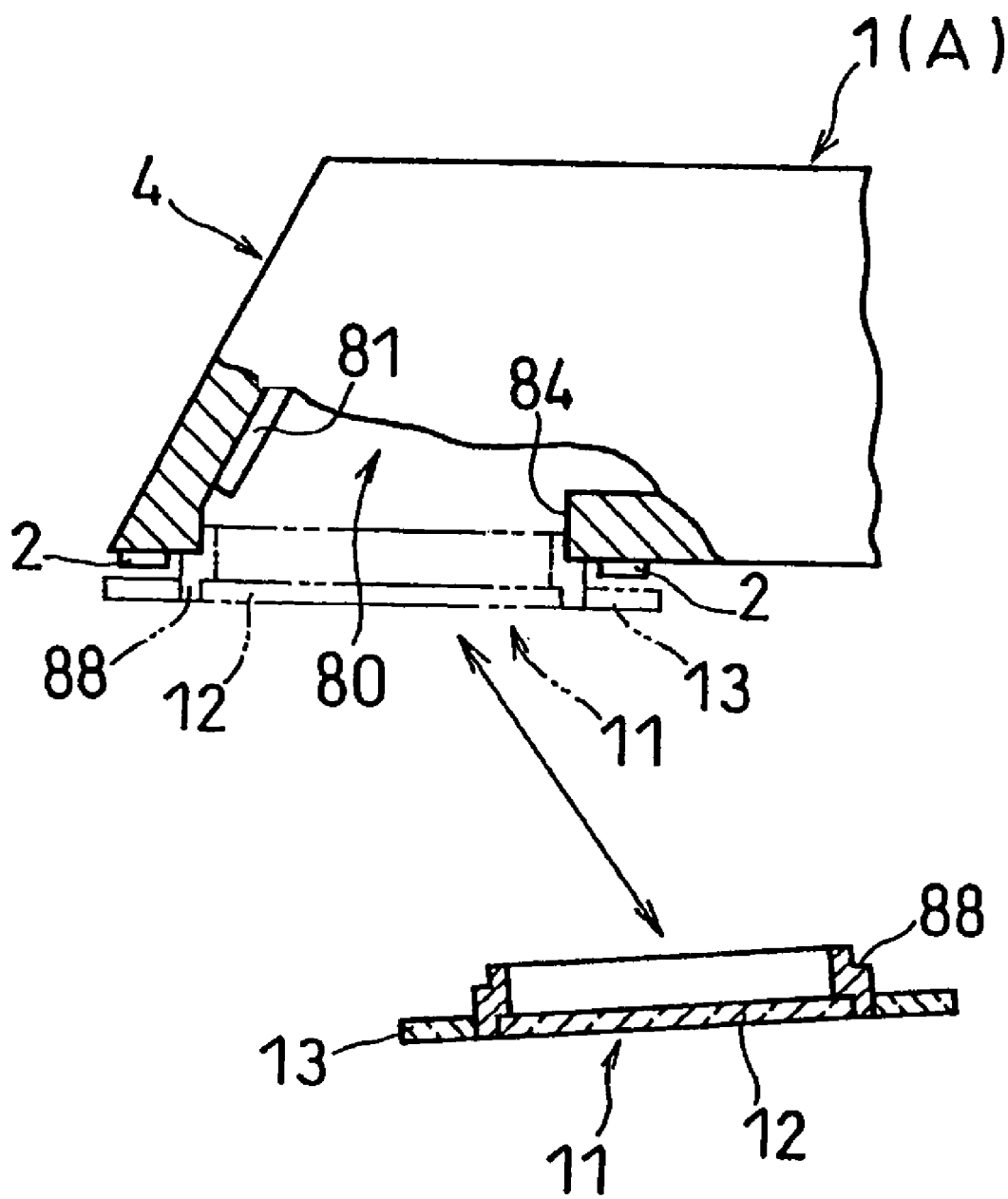
FIG. 37 shows a substantial part of a modified embodiment of the apparatus in FIG. 35.

FIG. 37 shows a modified embodiment of the diagnostic imaging apparatus A employing the above-mentioned optical path changing means. The apparatus A is constructed such that plural LEDs (luminous means) 2 are provided around the opening 84 in the forward portion 4 as mentioned above and a compound filter 11 which is made by integrating the light receiving filter 12 and the radiation filter 13 is supported by a support member 88 so as to be detachably provided to the opening 84. The radiation filter 13 is arranged so as to face the emitting surface of the luminous means 2 and the light receiving filter 12 is arranged so as to cover the opening 84 of the light introduction path 80. The functions of these filters are the same as mentioned above, so their explanations are omitted here.

When the optical image is thus designed to be formed on CCD 3a via an optical system, the CCD 3a isn't required to be provided at the end of the forward portion 4. Only provided at the tip end is the mirror 81 so that the tip end of the forward portion 4 may be designed compact, thereby increasing the aptitude as the dental imaging apparatus used by inserting in oral cavity and increasing its practical value.

Embodiment 16

Figure 38:
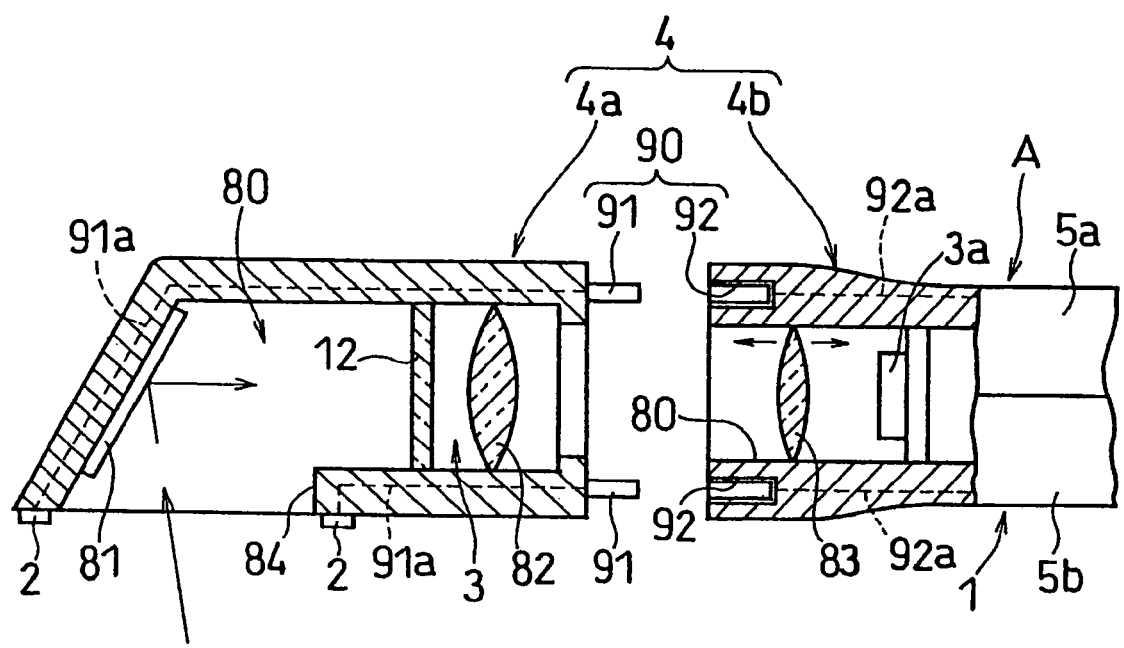
FIG. 38 is a partially cutaway vertical partial section of other embodiment of the diagnostic imaging apparatus using a optical path changing means.

According to the embodiment in FIG. 38, the imaging means has the optical path changing means as mentioned in the embodiment 15 and the forward portion 4 is able to be separated into a head portion 4a and a base portion 4b. The members common to the embodiment 15 have the same reference numerals. The mirror (or prism) 81 is attached as the optical path changing means so as to have about 45 degrees against the optical axis in the tubular head portion 4a and the CCD 3a is provided in the tubular base portion 4b of the forward portion 4. When the head portion 4a and the base portion 4b are connected by means of a connection means, detailed hereinafter, the tubular part between the mirror 81 and CCD 3a forms the light introduction path 80 of the imaging light.

The relay lens 82 is provided in the head portion 4a along the light introduction path 80 and the relay lens 83 movable along the optical axis is provided in the base portion 4b respectively so that an optical system for forming an optical image on the imaging means 3 is constructed with the mirror 81 and the relay lenses 82, 83. The opening 84 for entering light which is opened in a direction substantially perpendicular to the optical axis of the head portion 4a is formed so as to be communicated with the light introduction path 80. The light receiving filter 12 is provided around the front side (tip end side) of the relay lens 82.

Plural numbers of LEDs (luminous means) 2 are provided with space around the opening 84 along the circumferential direction. Lead wire 91a . . . embedded in the wall of the head portion 4a is connected to each LED 2 and is further connected to a male electrode 91 . . . projecting at the base portion side of the head portion 4a. On the other hand, a female electrode 92 . . . is provided in concave manner corresponding to the male electrode 91 . . . at the head portion side of the base portion 4b. The female electrode 92 . . . is connected to a power source, not shown, in the main body 1 via a lead wire 92a . . . embedded in the wall of the base portion 4b.

By fitting the male electrode 91 . . . and the female electrode 92 . . . , a connection means 90 of the head portion 4a and the base portion 4b is achieved and, in addition, the electric connection between both electrodes is formed. Therefore, the head portion 4a is easily attached and detached to the base portion 4b by manipulating the head portion 4a. And the male electrode 91 . . . and the female electrode 92 . . . are electrically connected so that power is supplied to the LED 2 from the power source by operating a switch, thereby achieving activation and emission.

In the above-mentioned construction, if plural kinds of head portions 4a combined with plural kinds of light receiving filters 12 with different wavelength characteristics and plural kinds of LEDs 2 with different emission characteristics are prepared, multiphase diagnostic photography is executed according to the condition of the diagnostic object or the diagnostic purpose by selectively attaching the head portion 4a to the base portion 4b via the connection means 90.

That is, if the head portion 4a with the white LED 2 and without a light receiving filter 12 (including glass) is used, the visible light image obtained by the reflected light from the diagnostic object is obtained. If the head portion 4a with the exciting light LED and with the light receiving filter 12 cutting off the exciting light is used, a clear fluorescence image of the diagnostic object is obtained. Further, the head portion 4a with the infrared LED and with the light receiving filter 12 transmitting only the reflecting light from the diagnostic object member by the radiated infrared light is used, a clear infrared reflected image can be obtained. In this case, the light receiving filter isn't actually required because the reflected image is obtained, however, such a light receiving filter 12 is sometimes required because the infrared reflected image is masked by sunbeam when strong sunbeam enters in the imaging means 3.

Plural LEDs 2 with different emission characteristics may be provided for one head portion 4a so as to be suitably controlled to emit light and further, plural light receiving filters 12 with different wavelength characteristics may be prepared to be exchangeable, so that multiphase diagnostic image information is obtained according to the condition of the diagnostic object member or the diagnostic purpose as mentioned above. The diagnostic imaging apparatus A of this embodiment is advantageous such that more multiphase diagnostic image information can be obtained in addition to the effect of the diagnostic imaging apparatus A in the embodiment 15.

Of course the detachable mechanism as mentioned in the above embodiments is employed or a control system is selectively employed in place of the attaching mechanism of the luminous means 2 and the light receiving filter 12 of the diagnostic imaging apparatus A in the embodiments 15 and 16. In this embodiment, the head portion 4a is designed to be detachable to the base portion 4b between the relay lens 82 and the relay lens 83, however, the present invention isn't limited to it. For example, they are separated and detachable between the relay lens 82 and the light receiving filter 12, between the mirror 81 and the light receiving filter 12, or between the relay lens 83 and the CCD 3a. In addition, it goes without saying that the detachable mechanism of the luminous means 2 and the detachable mechanism of the compound filter 11 in the embodiment 15 can be employed in this embodiment.

Embodiment 17

Figure 39:
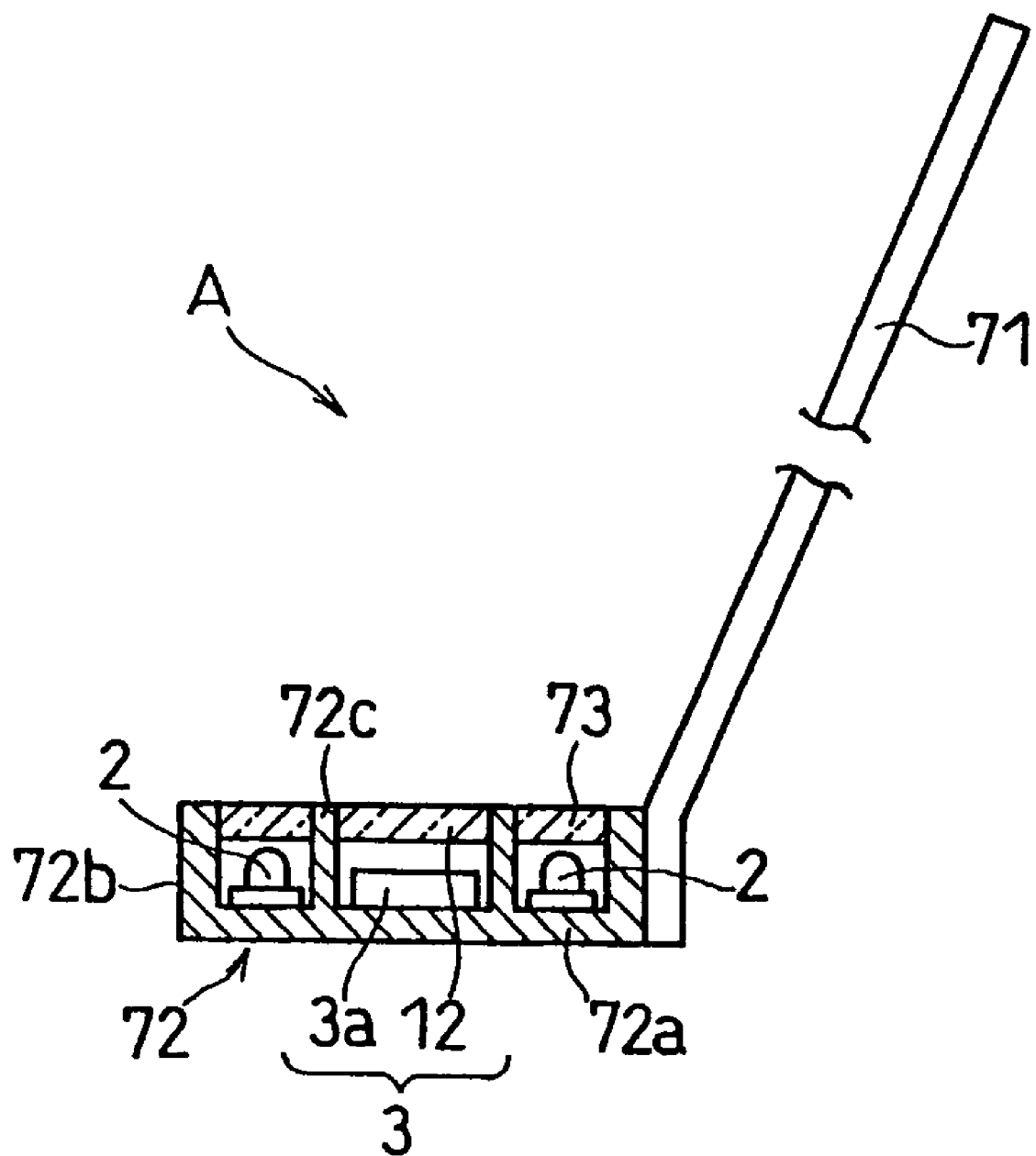
FIG. 39 is a partially cutaway side view of a dental mirror type diagnostic imaging apparatus.
Figure 40:
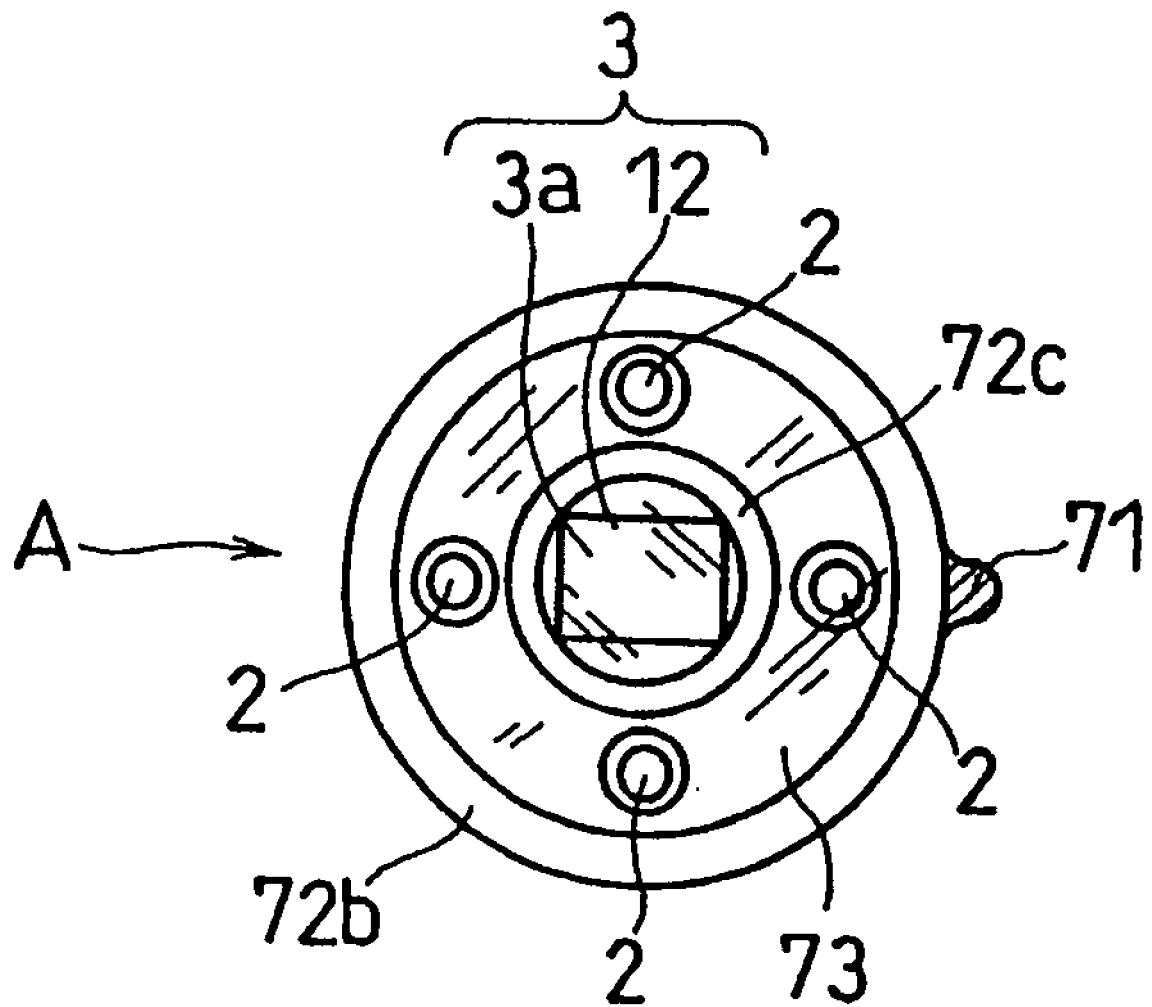
FIG. 40 is a plane view of a substantial part of the diagnostic imaging apparatus of FIG. 39.
Figure 41:
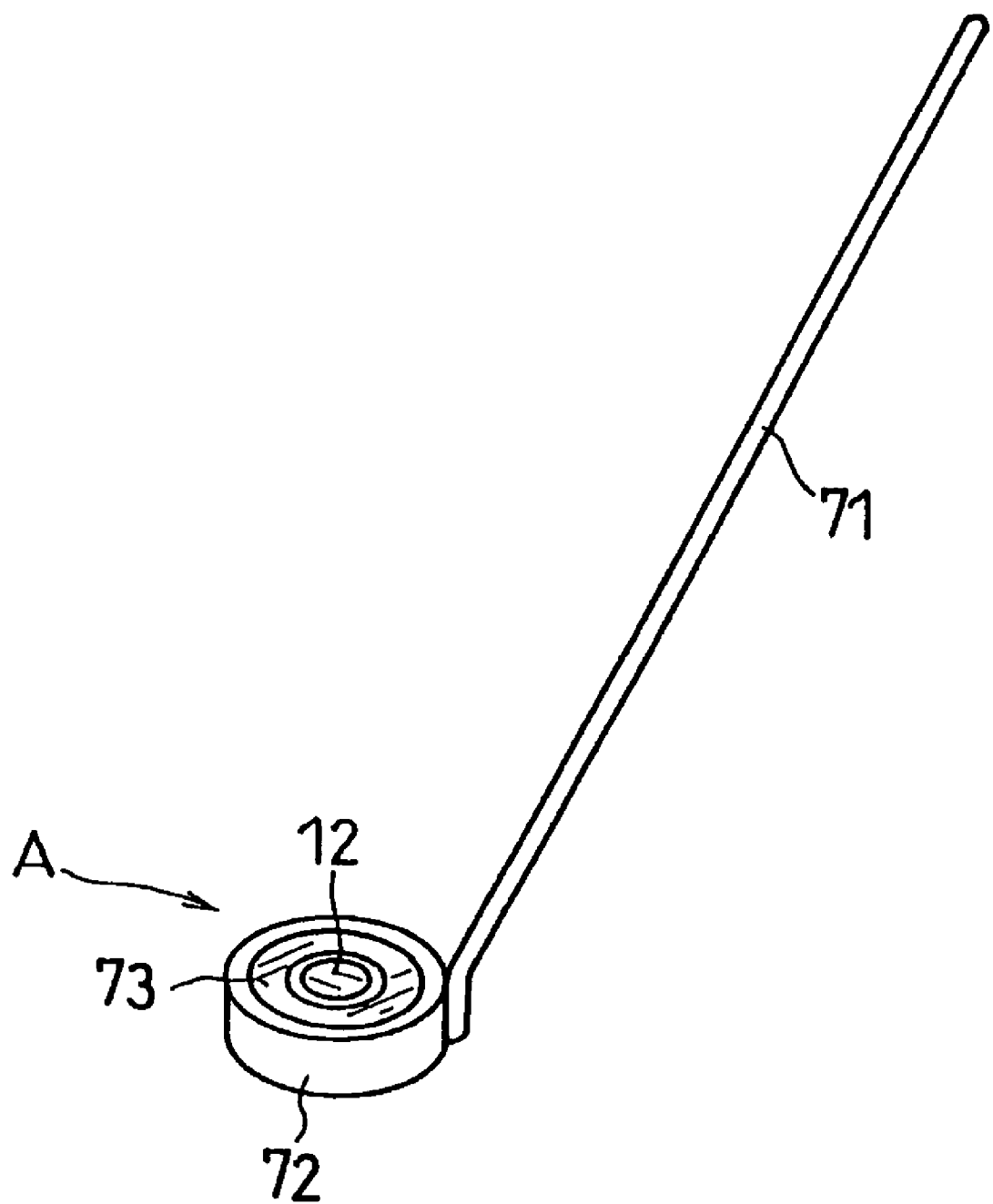
FIG. 41 is a perspective view of the diagnostic imaging apparatus of FIG. 39.
Figure 42:
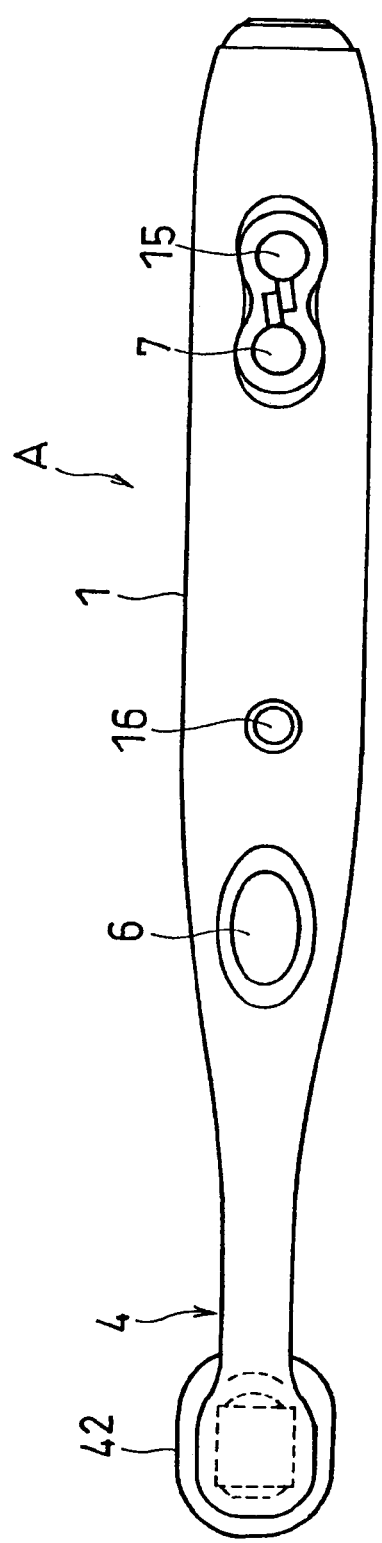
FIG. 42 is a plane view showing one embodiment of a diagnostic imaging apparatus provided with a light shielding hood according to the present invention.

FIG. 39-FIG. 41 show a dental mirror type diagnostic imaging apparatus. According to the diagnostic imaging apparatus A in the figures, the LED (luminous means) 2, the CCD (imaging means) 3a, and the light receiving filter 12 are provided for a frame (forward portion 4) 72 attached to the tip end of a support bar 71 held by hand's fingers, thereby being constructed as a compact dental mirror type. The frame 72 is comprised of a circular bottom wall 72a, a tubular periphery wall 72b and a tubular partition wall 72c in such a manner that four LEDs 2 are provided between the periphery wall 72b and the partition wall 72c and the CCD 3a is provided in the partition wall 72c.

Four LEDs 2 are provided with an equal space per 90 degrees around the axial center of the CCD 3a and are covered with an annular transparent glass 73 provided between the periphery wall 72b and the partition wall 72c. Disc-like light receiving filter 12 for the CCD 3a is provided in the partition wall 72c to be served as a cover. The diagnostic imaging apparatus A is thus designed to be very compact so that the diagnostic object member (photography object) in oral cavity can be simply and conveniently photographed with superior operationality like a dental mirror. A part of the transparent glass may be the radiation filter.

Next explained are embodiments with a light shielding hood for preventing external light at the light entrance of the forward portion. "For preventing external light" herein means the concept that all of the external light is prevented from entering and further that the external light is prevented from entering such that the diagnostic image information obtained by the diagnostic object base portion on radiation of the luminous means isn't adversely effected. The common members to the above-mentioned embodiments have the same reference numerals and their explanations are omitted here.

Embodiment 18

The diagnostic imaging apparatus A shown in FIG. 42-FIG. 47, like the embodiments mentioned above, is provided with the main body 1 like a dental hand piece supportable with hands and fingers, and the forward portion 4 incorporating the luminous means 2 (light emitting member 2*a*, 2*b*, 2*c*) for radiating at least one of the light among exciting light, infrared light, ultraviolet light and white light, and incorporating the imaging means 3 constructed with the CCD (solid-state image sensing device) 3*a*. A light entrance 41 opened into a direction perpendicular to the longitudinal direction of the main body 1 is provided for the tip of the forward portion 4 and a light shielding hood 42 is provided for the light entrance 41 so as to prevent external light invasion.

This diagnostic imaging apparatus A is suitable for diagnosing caries, deficit part, crack, lesioned part, dental calculus, and dental plaque of the teeth, and attached condition of biofilm in oral cavity. The apparatus can take a picture of the tooth surface and further can recognize the lesioned part inside of the surface of the tooth by taking a picture of inside of the surface (about 1 mm inside from the surface). Further, if it is constructed as a cordless apparatus, it transmits signals to the control box H (see FIG. 43) via cordless manner so that the obtained image is printed out to be taken out. Moreover, a zoom mechanism for executing zoom-in and zoom-out operations and an automatic focus mechanism may be provided.

The forward case 5*c* is detachably provided for the upper case 5*a* and the lower case 5*b* as mentioned above and the light receiving filter 12 for the imaging means 3 is provided for the light entrance 41. The light shielding hood 42 is provided so as to surround the light receiving filter 12.

The main body 1 is constructed such that the photography switch (relating to the image storage means for obtaining static image) 6, the light source selection switch 7, the image selection switch 15, the automatic sequence photography switch 16 are attached to the upper case 5*a*. The power source 8 such as a secondary battery for driving the luminous means (light emitting member) 2 and the imaging means 3, the wireless transmitter 9 for transmitting the information obtained by the imaging means 3 to the control box H and the microcomputer 17 are included in the main body 1. This diagnostic imaging apparatus A is also designed to be cordless, however, if it isn't a cordless type, the photography switch 6 may be provided for any place other than the main body 1 such as the control box H and the foot pedal (not shown) via the lead wire which are connected to the diagnostic imaging apparatus A, as mentioned in the above-mentioned embodiments.

Figure 44:
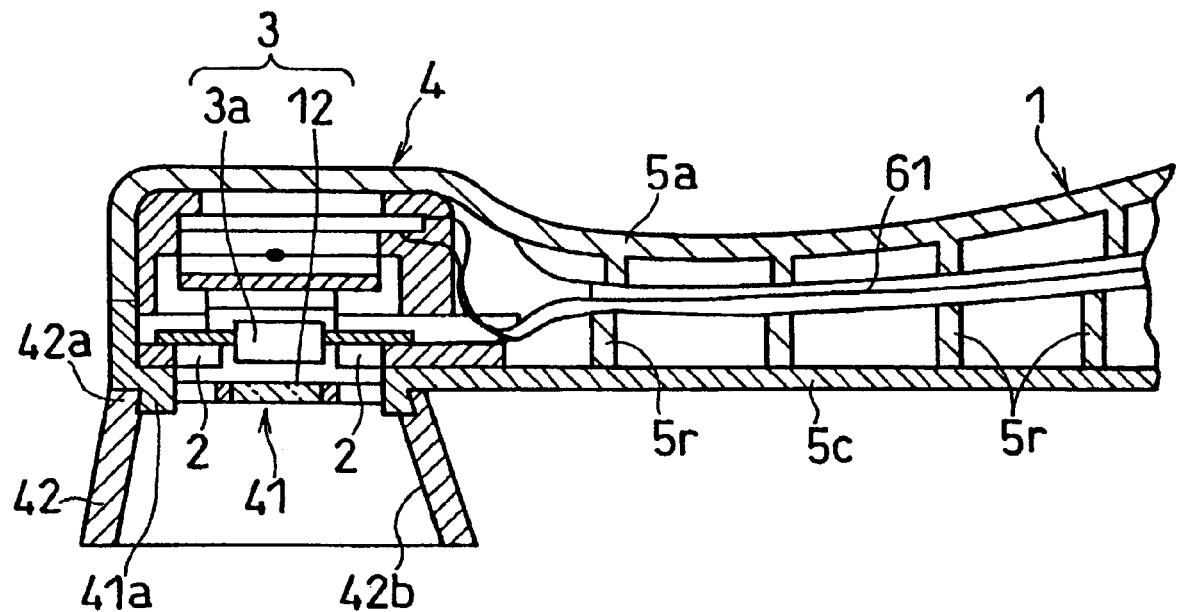
FIG. 44 is an enlarged vertical section of the forward portion of the diagnostic imaging apparatus of FIG. 42.
Figure 45:
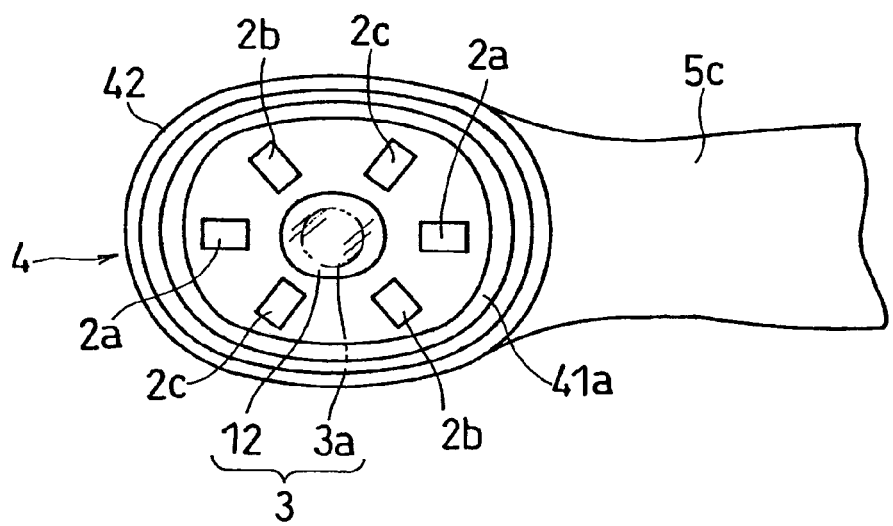
FIG. 45 is an enlarged bottom view of the forward portion of the diagnostic imaging apparatus of FIG. 42.
Figure 46:
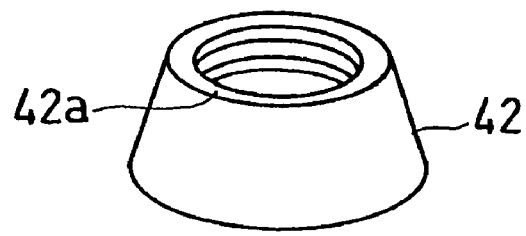
FIG. 46 is a perspective view of a light shielding hood.

The imaging means 3, the luminous means (light emitting member) 2, and the light receiving filter 12 are provided for the forward portion 4 as shown in FIG. 44 and FIG. 45. The imaging means 3 is comprised of the CCD (solid-state image sensing device) 3*a* and the light receiving filter 12 as an optical means when the radiation light from the luminous means 2 is irradiated on the diagnostic object such as teeth, the imaging means 3 receives the light reflected from the diagnostic object and/or the fluorescence generated by radiating exciting light on the diagnostic object to obtain a predetermined diagnostic image.

The luminous means 2 is comprised of six LEDs (light emitting diode) consisting of three kinds of two LEDs, namely the white LED (light emitting diode) 2*a* as a light emitting member, the infrared LED (light emitting diode emitting infrared light) 2*b*, the ultraviolet LED (light emitting diode emitting ultraviolet light) 2*c*. They are arranged around the optical axis of the CCD 3*a* with an equal angle interval so as to be rotationally symmetrical. Hereby the light from the luminous means 2 is designed to be directly irradiated on the teeth. Each pair of LED 2*a*, 2*b*, 2*c* (light emitting diode) are arranged so as to face with 180 degrees apart around the circumferential direction, however, this invention isn't limited to such an arrangement and combination of the radiation light source.

The luminous means 2 preferably radiates at least one of exciting light (preferably exciting light with a single wavelength), infrared light, ultraviolet light, and white light. It may be LED, a laser oscillator (semiconductor laser such as He—Ne laser, krypton laser and dye laser or solid laser) or a halogen lamp, as mentioned above.

Figure 43:
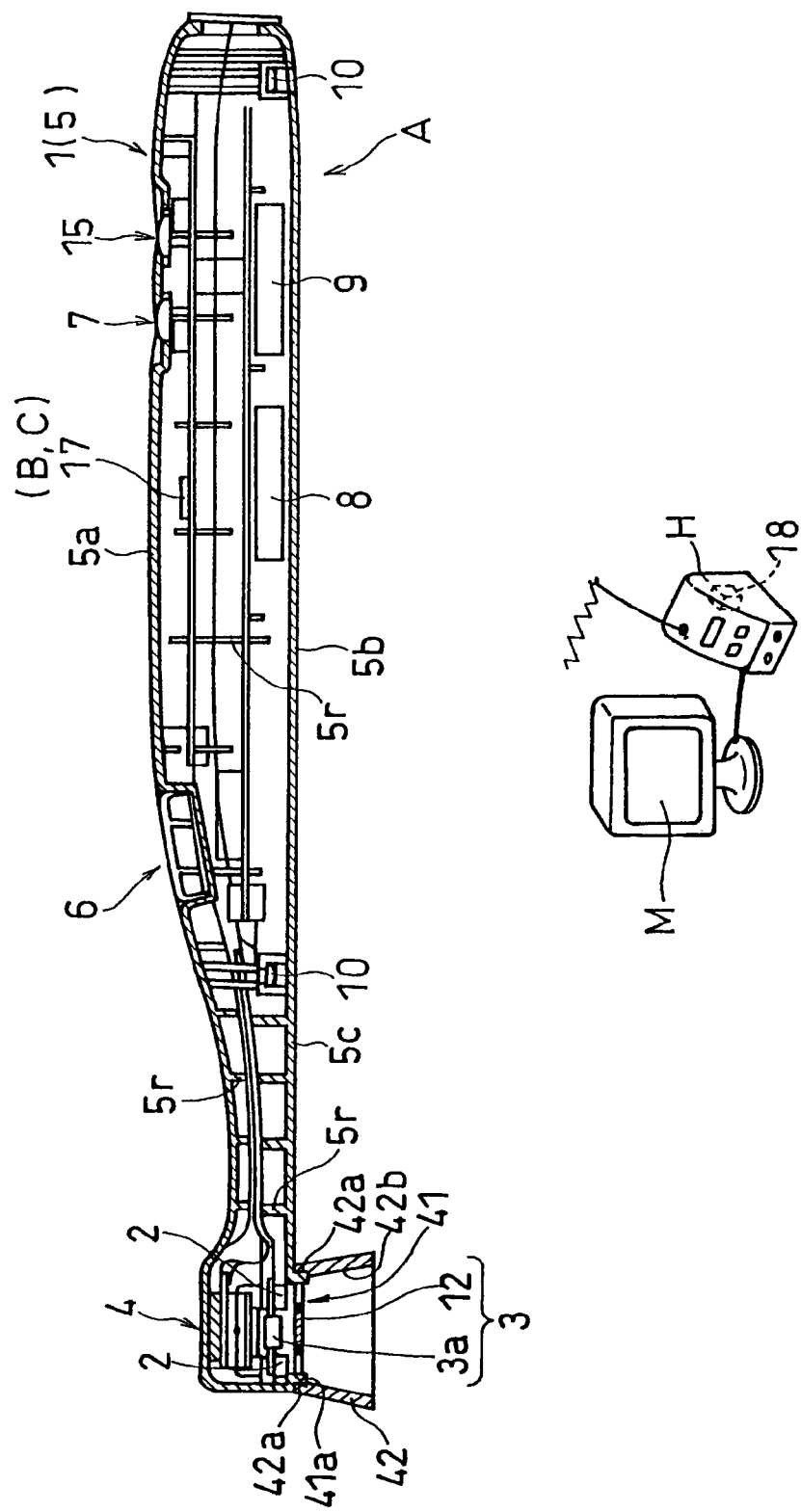
FIG. 43 is a vertical section along the longitudinal direction of the diagnostic imaging apparatus of FIG. 42.

The light receiving filter 12 is provided so as to be fitted in the light entrance 41 of the forward case 5*c* as shown in FIG. 43-FIG. 45 and is formed as a disc-like plate so as to cover the bottom side of the CCD 3*a* and the LEDs 2*a*-2*c*. The light shielding hood 42 is made of soft elastic tubular member such as rubber and is formed so as to be enlarged into its end in the embodiment of FIG. 42-FIG. 47. The base portion end 42*a* with a smaller diameter is designed so as to be externally fitted, accompanied with elastic deformation, to a stepped attachment member 41*a* with different diameter formed at an open periphery of the light entrance 41. The inner wall of the light shielding hood 42 is formed with a light reflecting surface 42*b* is mirror finished.

Figure 48:
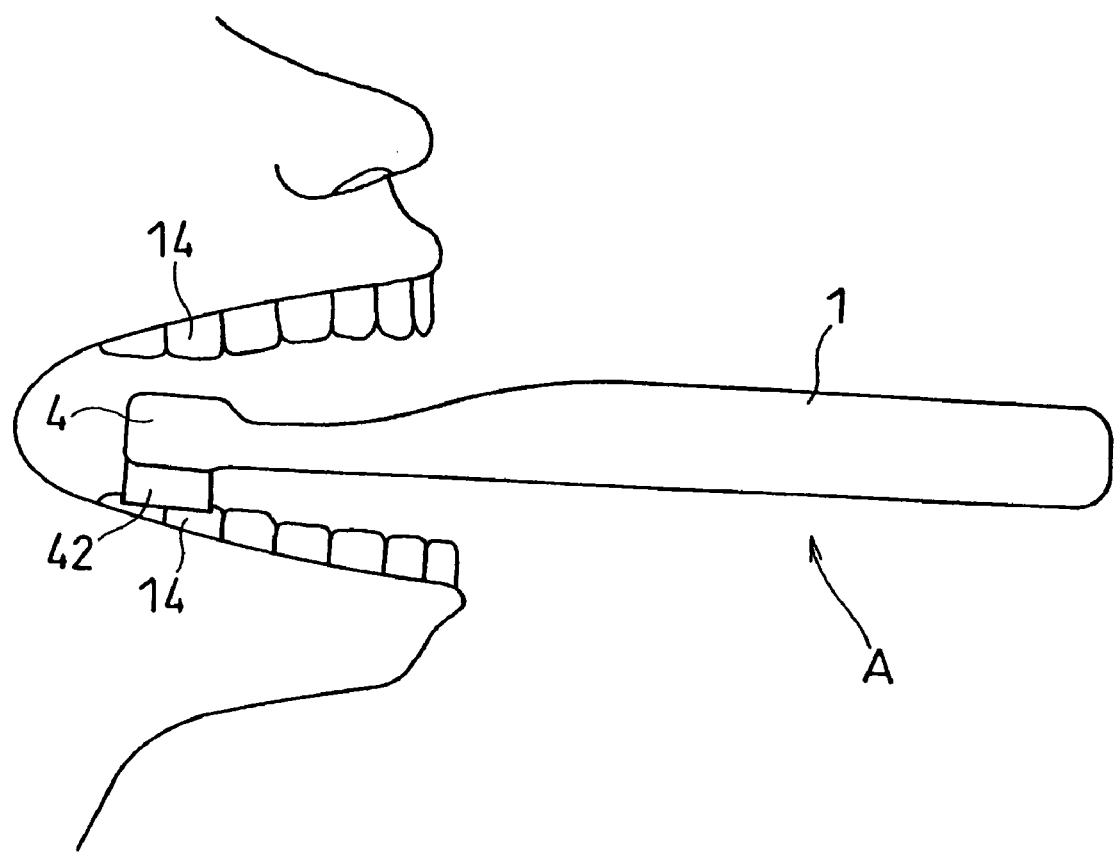
FIG. 48 shows how the oral cavity is diagnosed by means of the diagnostic imaging apparatus of FIG. 42.

FIG. 48 shows how the above-mentioned diagnostic imaging apparatus A is used. As shown in the figure, the forward portion 4 of the apparatus A is inserted into oral cavity and the tooth 14 is diagnosed in such a manner that the light shielding hood 42 is approached with, is attached to, or is fixed up the surface of the tooth 14 as a diagnostic object. While the image formed by the imaging means 3 is displayed on the monitor M connected to the control box H (for both of them, refer to FIG. 2), diagnosis can be executed. If there is an interested area, the photography switch 6 is operated during photography of the interested area, the static image of the area is stored in the memory 18 of the main body 1 or the control box H, and the image is printed out by means of a printer (not shown) connected to the control box H if necessary. According to this diagnostic imaging apparatus A, the radiation light from the luminous means 2 can be directly irradiated to the tooth 14.

As mentioned above, the imaginary line in FIG. 7 shows a lesioned part. The fluorescence generated from the lesioned part is got lost in the room light or sunbeam because it is generally a faint light. Therefore, if the disturbance light is blocked off by the light shielding hood 42, the influence of the disturbance light is excluded, thereby obtaining a clear fluorescence image by the imaging means 3. Therefore, the condition of the lesioned part is accurately observed with eyes by the obtained image.

According to the diagnostic imaging apparatus A of this embodiment, the tubular light shielding hood 42 is provided for the light entrance 41 and the apparatus A is operated such that the light shielding hood 42 is fixed up the surface of the tooth 14. The positioning is accurately done, the disturbance light such as the light in an examination room and sunbeam is blocked off by the light shielding hood 42, therefore, only the reflected light or the fluorescence from the tooth 14 by irradiating from the luminous means 2 is received in the imaging means 3, namely the CCD 3*a*. Accordingly, the obtained reflected light image and fluorescence image become clear without being affected by the disturbance light. Further, the inner wall of the light shielding hood 42 is the reflecting surface 42b by mirror finish so that entering of the disturbance light is prevented and scattering and discharging of the reflected light or fluorescence from the tooth 14 are also prevented, thereby enabling the CCD 3a to effectively receive light.

The dental calculus, dental plaque, or dental caries (bad tooth) in the inner part near the tooth surface which isn't easily seen on the visible light image but is made clear by fluorescence is sharply recognized on the visible light image of the tooth surface taken by the visible light, so that where the dental calculus, dental plaque or dental caries (bad tooth) exists can be understood at a glance. The visible light image and the fluorescence image are overlapped in FIG. 6, however they may be displayed respectively per an image for diagnosis purpose. However, dental caries (bad tooth) is clearly seen with eyes and teeth image itself isn't clear on the fluorescence image. On the other hand, the teeth outline is clear on the visible light image. Therefore, those images compensate their defects each other by overlapping them, thereby obtaining a high quality diagnostic image information with clear teeth outline and clear dental calculus, dental plaque, and dental caries (bad tooth).

Figure 49:
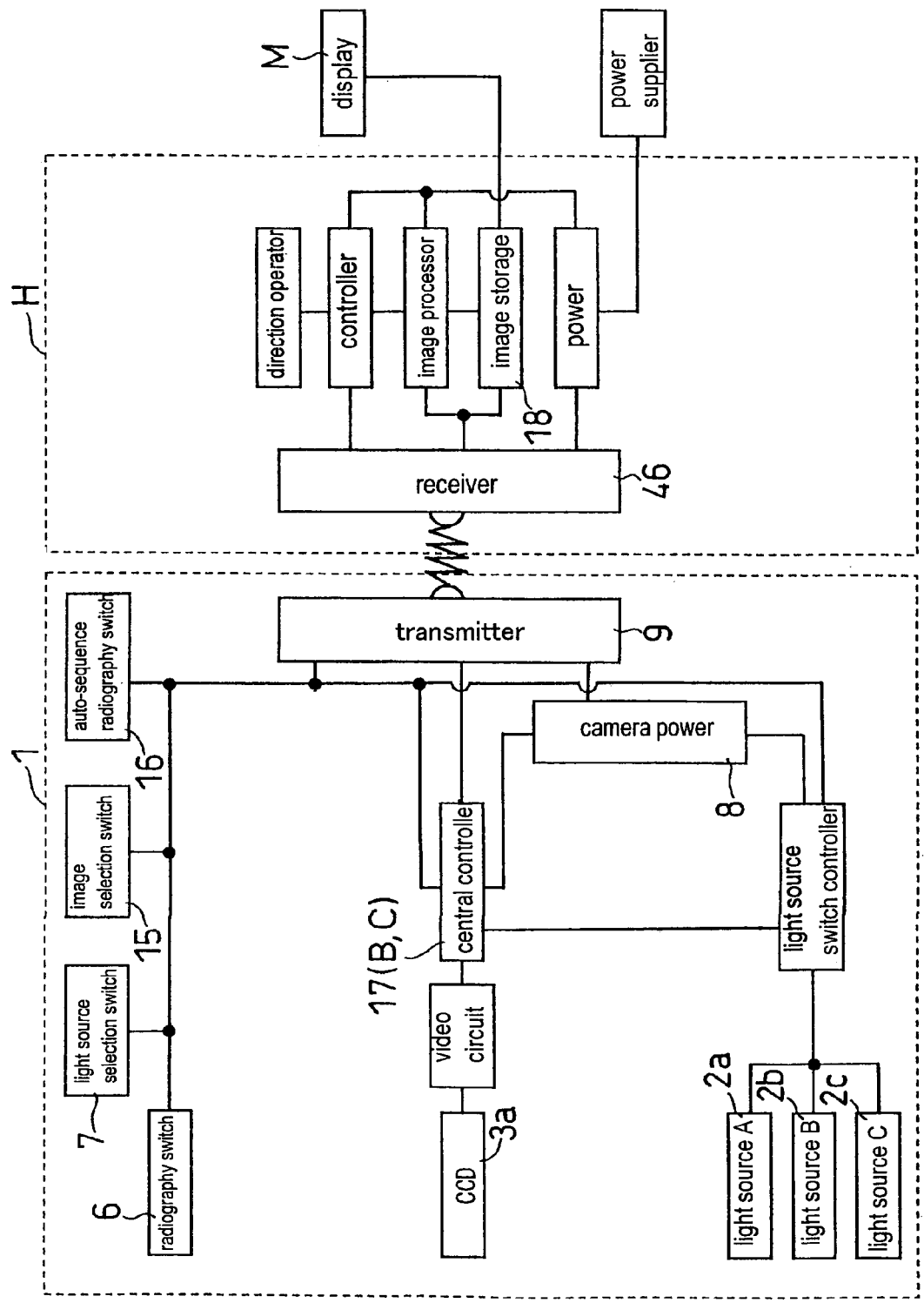
FIG. 49 is a block diagram showing the entire system using a cordless diagnostic imaging apparatus.

Here one example of the entire system construction including the diagnostic imaging apparatus A in this embodiment is explained. The system is roughly divided into the main body 1, the control box H and the display M as shown in FIG. 49. Signals are sent between the main body 1 and the control box H via wireless (cordless) manner by means of the transmitter 9 and the receiver 46. Each construction members are shown in FIG. 49 and the explanation of each member is omitted here.

The main body 1 is provided with several switches 6, 7, 15, 16, the central processing unit corresponding to the microcomputer 17, a control unit for switching light source corresponding to the radiation light source switching means D (explained later), and a video circuit for converting the signals from the CCD into video signals. The control box H is provided with the receiver 46, a direction operation unit (corresponding part to each switch 6, 7, 15, 16), a control unit, an image processing unit, an image storage unit (an image storage means) corresponding to the memory 18, and a power source. Display M such as liquid crystal display and a power supply unit (outlet connected to commercial power) are connected to the control box H.

Figure 50:
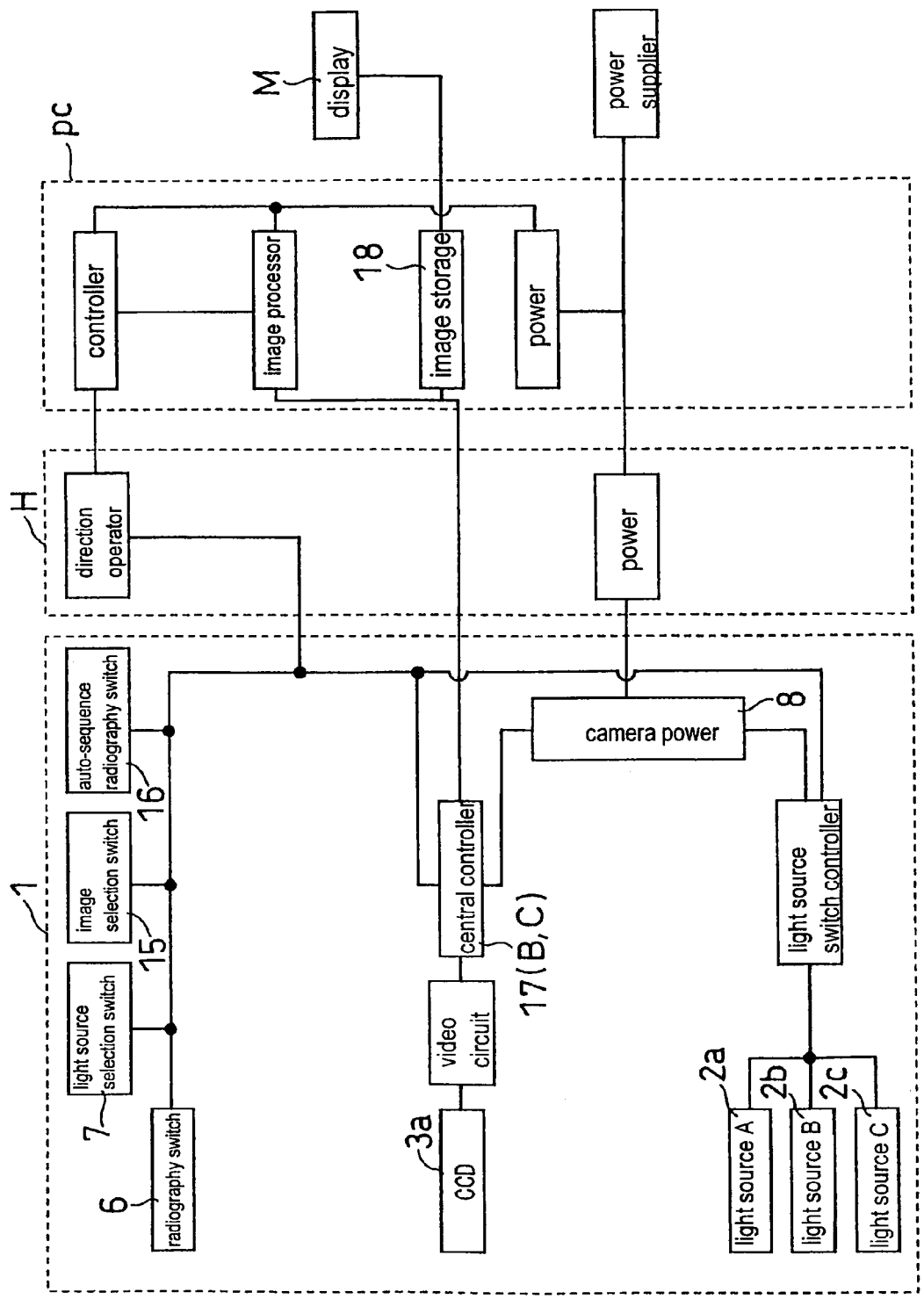
FIG. 50 is a block diagram showing the entire system using a wired diagnostic imaging apparatus and a personal computer.

FIG. 50 shows one embodiment of the entire construction of the wired system including the diagnostic imaging apparatus A including the personal computer pc. The main body 1 in the figure is the same as that shown in FIG. 49 other than that the transmitter 9 is replaced with a lead wire such as a cable. The control box H is provided with the direction operation unit (same as shown in FIG. 49) and the power source. The personal computer pc is provided with a control unit, an image processing unit, an image storage unit corresponding to the memory 18, and a power source and is connected with a display M and a power supply unit.

Thus constructed diagnostic imaging apparatus A doesn't have switching function of the light receiving filter and the radiation filter as mentioned in the above-mentioned embodiments, however it can execute several kinds of photography as mentioned above. The switches such as the photography switch 6, the light source selection switch 7, the image selection switch 15 and the automatic sequence photography switch 16, the image storage means B including the memory 18 provided for the microcomputer 17, and the automatic photography control means C have the same function as mentioned above. Therefore, in this case, when the automatic sequence photography switch 16 is turned on, the image obtained by radiating only the white LED 2a, the image obtained by radiating only the infrared LED 2b and the image obtained by radiating only the ultraviolet LED 2c (normal reflected image and fluorescence image) are continuously stored in a very short time as shown in the time chart in FIG. 10. Further, according to the same principle mentioned above, the image (part drawn with solid line) obtained by radiating light in a visible range is overlapped on the image (part drawing with imaginary line) obtained by fluorescence generated by radiating exciting light to obtain a complex image as shown in FIG. 6. In addition, the radiation light source selection means D shown in FIG. 13 may be employed to this embodiment. The light source selection switch 7 corresponds to the radiation light source selection means D, so its explanation is omitted here.

Embodiment 19

Figure 51A:
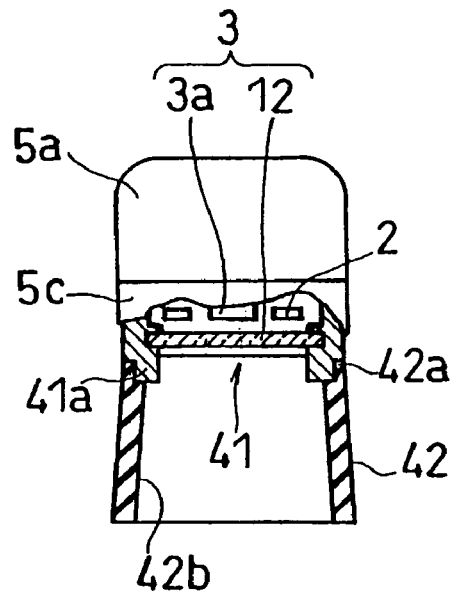
FIG. 51a is a partially cutaway front view of the forward portion.
Figure 51B:
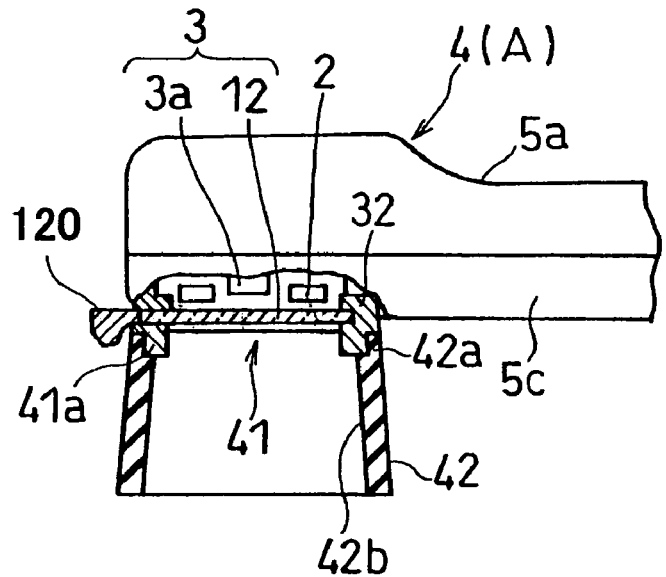
FIG. 51b is its partially cutaway side view.
Figure 51C:
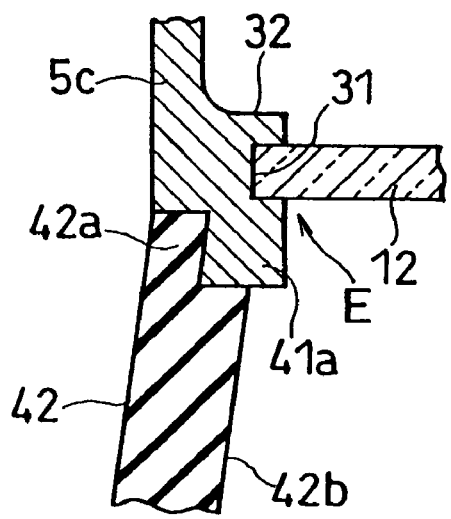
FIG. 51c is an enlarged view of a rail groove.

FIG. 51a, FIG. 51b, FIG. 51c show one embodiment of the diagnostic imaging apparatus A in which the light shielding hood 42 is further provided for the diagnostic imaging apparatus A with the filter detachable means E as shown in FIG. 19. The stepped attachment member 41a with different diameters as mentioned above is formed under the upheaval part 32 and the light shielding hood 42 made of soft elastic tubular member such as rubber is externally fitted up the attachment member 41a with the base portion 42a elastically deformed. Further, as mentioned above, the inner wall of the light shielding hood 42 is formed as a light reflecting surface 42b formed by mirror finish. Other constructions and functions are the same as those in FIG. 19.

Embodiment 20

Figure 52A:
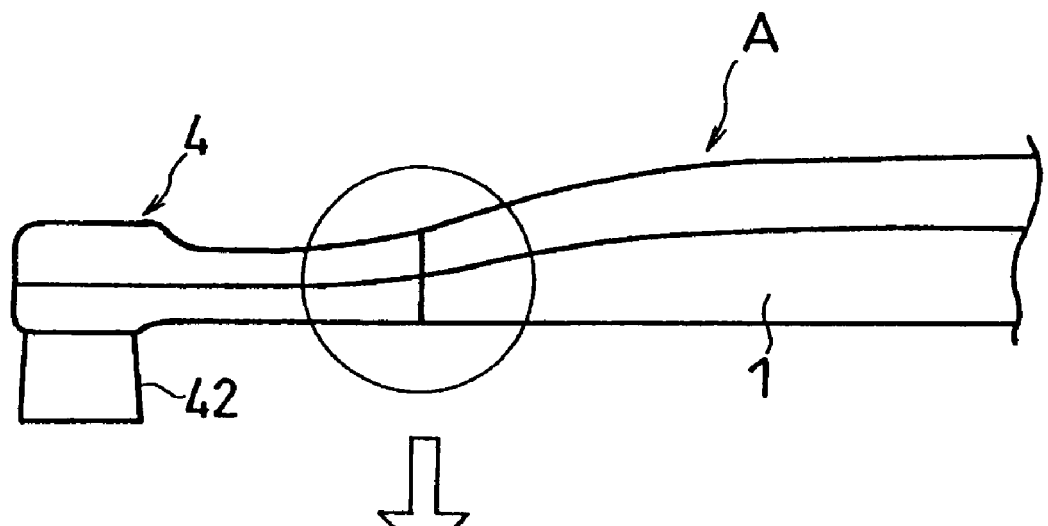
FIG. 52a is a bottom view of the forward portion of the diagnostic imaging apparatus.
Figure 52B:
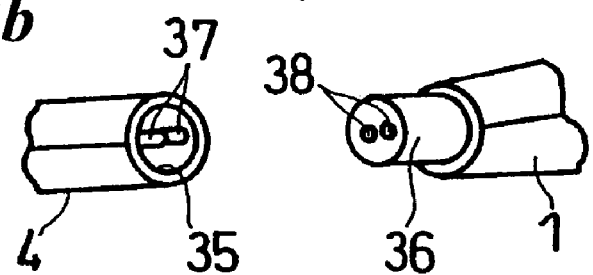
FIG. 52b is its exploded view when the forward portion is detached.

FIG. 52a and FIG. 52b are an embodiment of the diagnostic imaging apparatus A, of which the forward portion 4 is detachable to the main body 1 and which is further provided with the light shielding hood 42. Shielding function of the light shielding hood 42 is added to the detachable function of the forward portion 4. Other constructions are the same as the embodiment in FIG. 21, so their explanations are omitted here.

Embodiment 21

Figure 53:
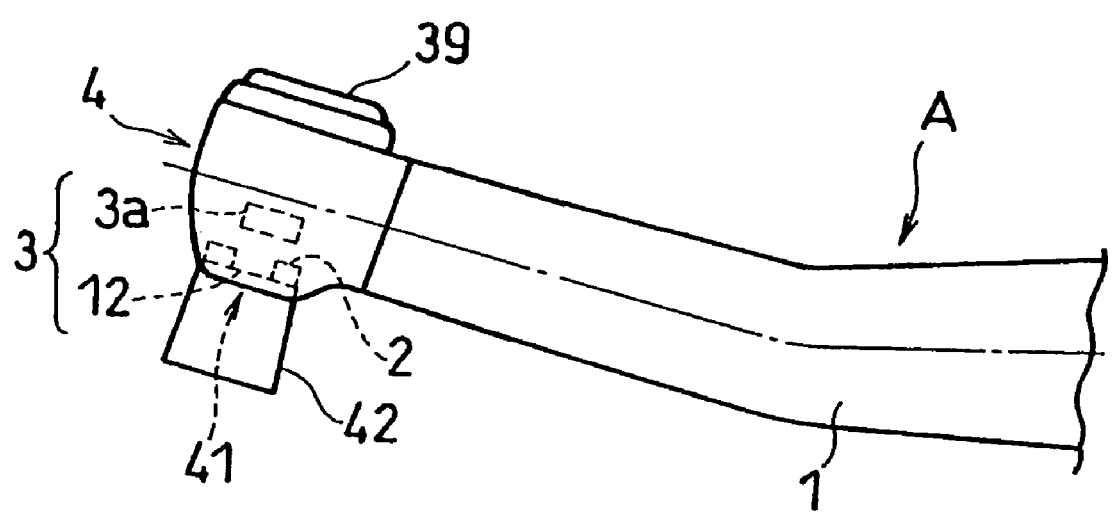
FIG. 53 is a side view showing other embodiment of a diagnostic imaging apparatus.

FIG. 53 is an embodiment of the diagnostic imaging apparatus A which is formed like a dental contra angle handpiece such that the forward portion 4 has a slight angle against the main body 1. The CCD 3a as the imaging means 3 is provided at the center of the circular head portion 39, which is seen from the top, at the forward portion 4, and the light receiving filter 12 and the above-mentioned light shielding hood 42 are provided for the light entrance 41. Plural LEDs as the luminous means 2 are provided at the back of the light receiving filter 12 so as to surround the CCD 3a when seen from the optical axis direction of the CCD 3a. In this case, it is preferable that several kinds of LEDs 2 such as infrared LED and blue LED are provided so as to execute several turn-on patterns.

Embodiment 22

Figure 47:
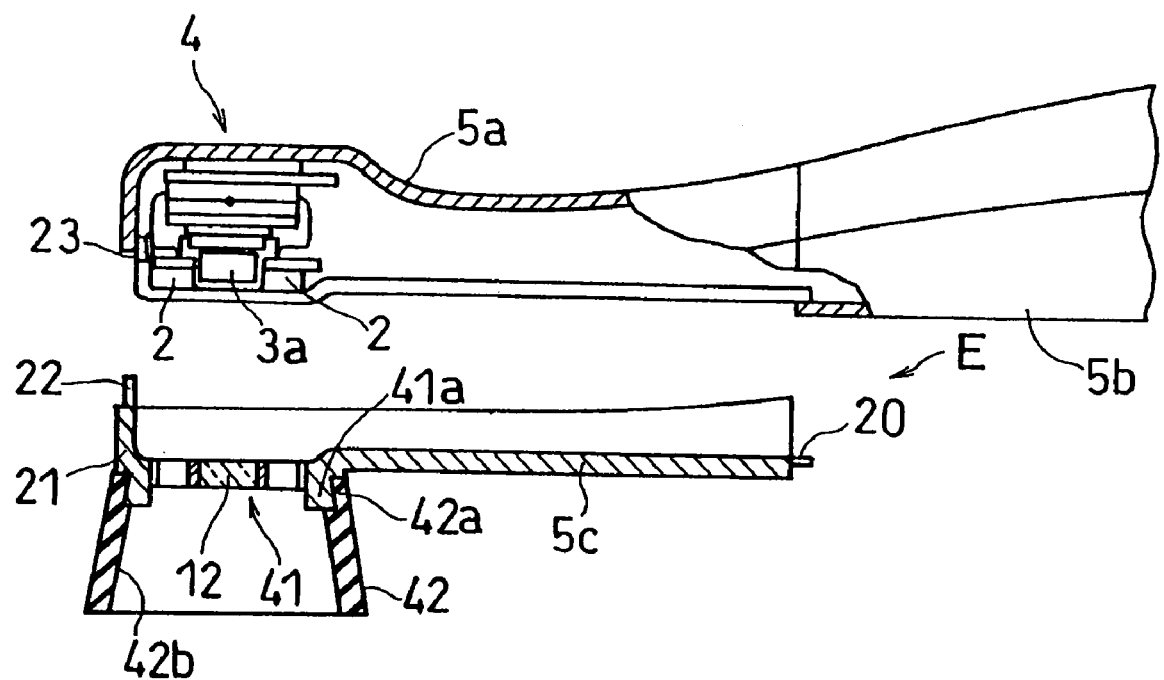
FIG. 47 is a front view of a forward portion of which vertical section is partially cut away.
Figure 54:
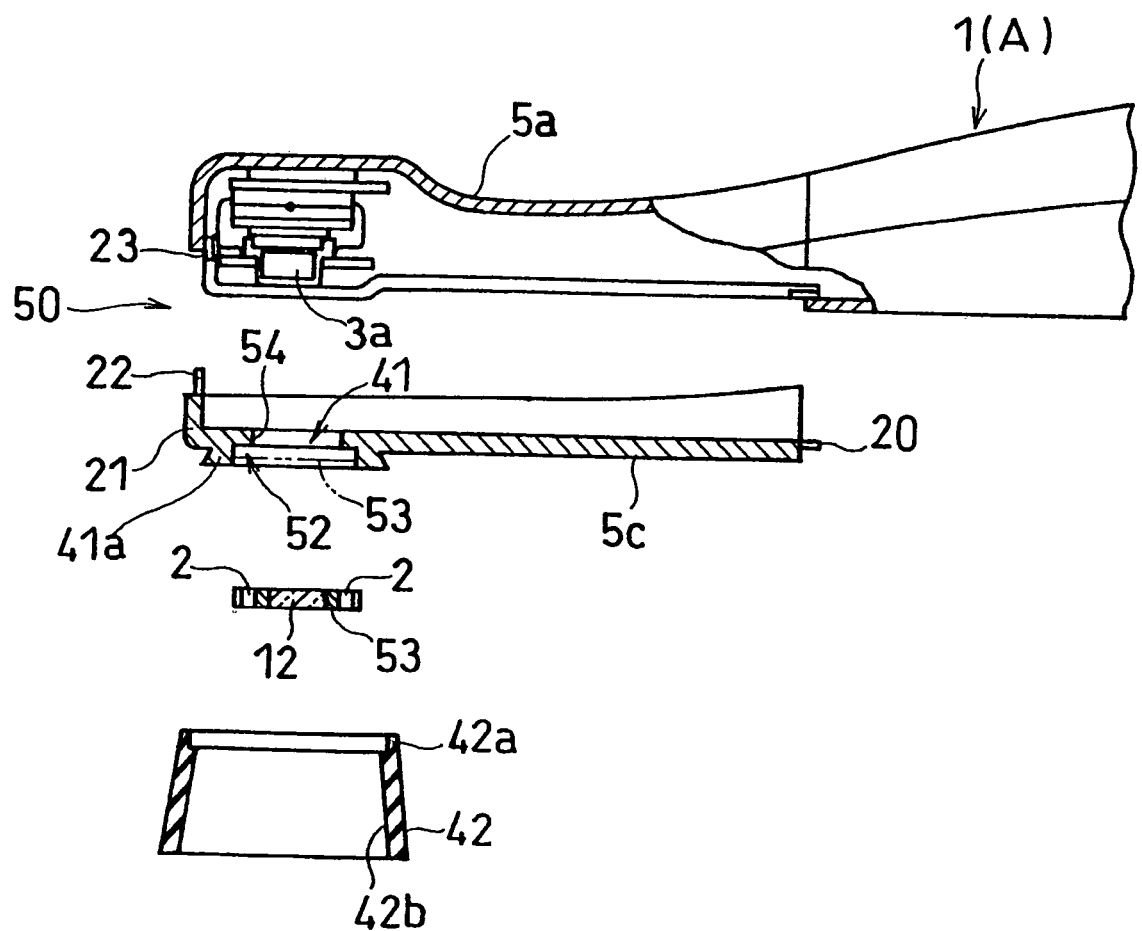
FIG. 54 is a sectional view of a photography member constructed such that a luminous means and a filter are integrated and detachable.

FIG. 54 shows a diagnostic imaging apparatus A provided with a forward case modified from that shown in FIG. 47. The diagnostic imaging apparatus A in the figure is constructed such that the opening 54 constituting the light entrance 41 which is the light introduction path to the CCD (constituting the imaging means 3) 3a and the stepped annular opening 52 formed therearound are provided for the forward case 5c (detachable attachment constituting a part of the forward portion 4). Further the support member 53 provided with the light receiving filter 12 and plural LEDs (luminous means) 2 arranged therearound is detachably provided for the stepped opening 52. Although not shown in the figure, a pair of terminal electrodes for the LED 2 are provided at the periphery of the support member 53 and the inner circumference of the stepped opening 52 so that these electrodes are connected to be conducted by attaching the support member 53 and they are disconnected by removing the member 53. Other constructions are the same as those shown in FIG. 47 and the common members have the same reference numbers, thereby omitting their explanation.

Embodiment 23

Figure 55:
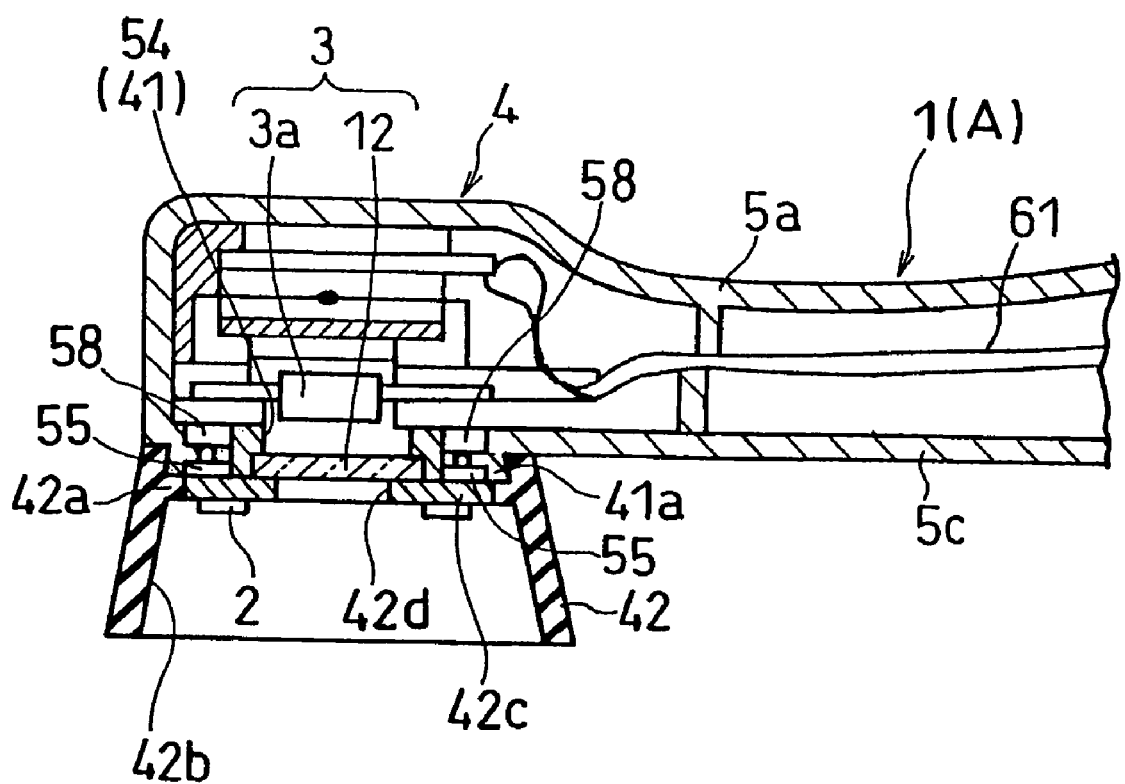
FIG. 55 is a partially cutaway partial vertical section of a diagnostic imaging apparatus constructed such that a light shielding hood and a luminous means are integrated and are provided at the forward portion detachably.
Figure 56A:
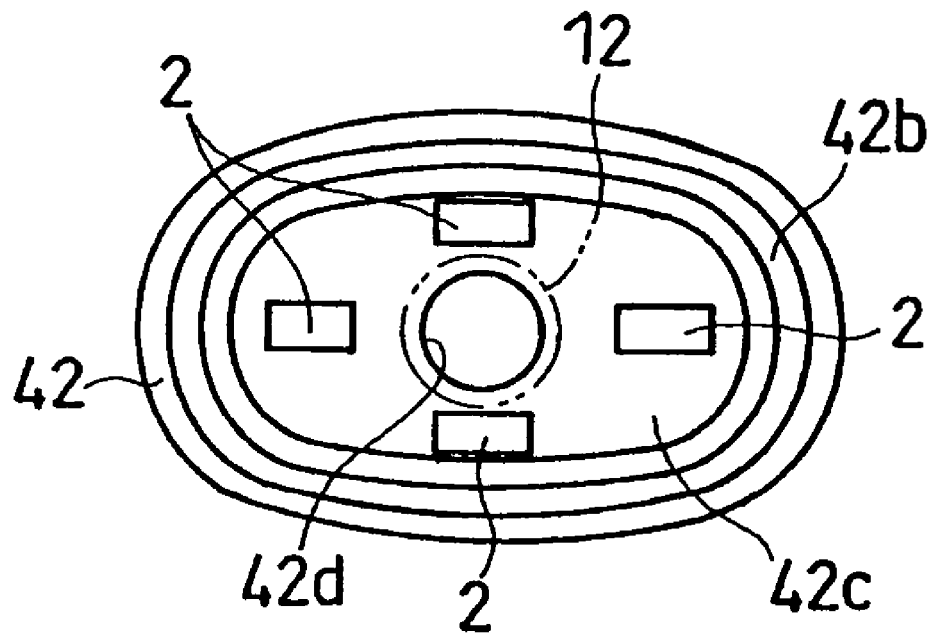
FIG. 56a is a view of the light shielding hood which is seen from the bottom according to the embodiment of FIG. 55
Figure 56B:
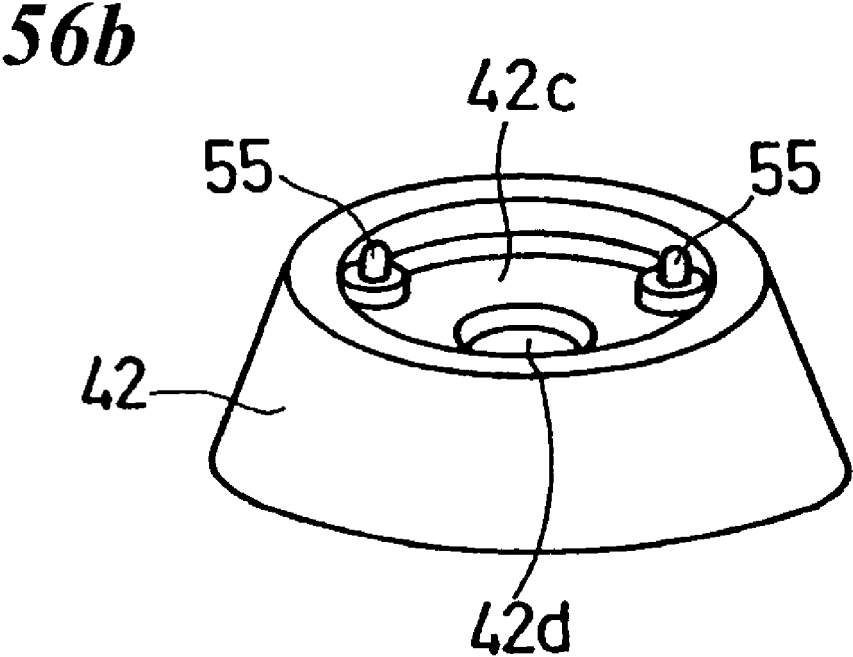
FIG. 56b is its perspective view.

FIG. 55 shows one embodiment of the diagnostic imaging apparatus A in which the light shielding hood 42 and the luminous means 2 are integrated so as to be detachable to the forward portion 4. FIG. 56a is a view when the light shielding hood 42 is seen from the bottom and FIG. 56b is its perspective view. The CCD 3a constituting the imaging means 3 is provided for the forward portion 4 and the light receiving filter 12 is attached to the opening 54 (constituting the light entrance 41) of the forward case 5c so as to oppose the CCD 3a. Four LEDs (luminous means) 2 are provided with an equal space in the circumferential direction via an annular support member 42c provided with a light introduction hole 42d at the center thereof in the base portion 42a which is a smaller diameter side of the above-mentioned light shielding hood 42. Convex electrode 55 is provided per each LED 2 at the back of the annular support member 42c. On the other hand, in the forward portion 4, the receiving electrode 58 is provided at the position corresponding to the convex electrode 55. Thus, when the light shielding hood 42 is externally fitted up the attachment 41a with the base portion 42a elastically deformed, both electrodes 55, 58 are electrically conducted. The reference numeral 61 indicates a lead wire for supplying power to the LED 2 or CCD 3a.

The diagnostic imaging apparatus A of this embodiment is used so as to fix up the light shielding hood 42 to the diagnostic object such a tooth, mentioned hereinbefore. The reflected light or fluorescence from the diagnostic object by the radiation light from LED 2 passes through the light receiving filter 12 from the light introduction hole 42d and is received in CCD 3a, resulting output of the diagnostic image information such as a visible light image and a fluorescence image. According to this embodiment, when several kinds of LEDs 2 with different radiation characteristics are attached to plural light shielding hoods 42, diagnostic image information corresponding to the condition of the diagnostic object and the diagnostic purpose can be obtained by selectively providing several kinds of light shielding hoods 42.

If the forward case 5c is constructed as a detachable attachment member to the main body 1, plural forward cases 5c are prepared per plural light receiving filters 12 with different wavelength characteristics and a suitable forward case 5c is selectively attached corresponding to the diagnostic purpose as mentioned above. However, when the forward case 5c is fixed, the light receiving filter 12 may be constructed to be detachable to the opening 54.

Embodiment 24

Figure 57:
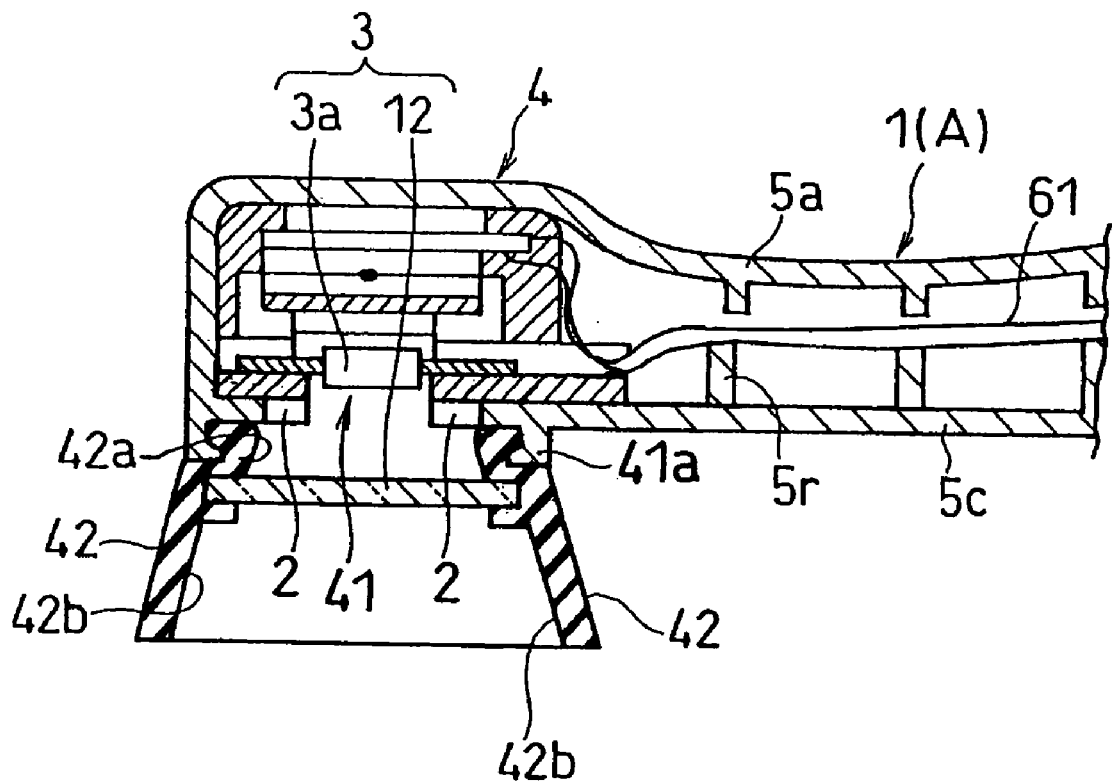
FIG. 57 is a partially cutaway vertical sectional view of a diagnostic imaging apparatus constructed such that a light shielding hood and a light receiving filter are integrated and are provided at a forward portion detachably.

FIG. 57 shows the diagnostic imaging apparatus A constructed such that the light shielding hood 42 and the light receiving filter 12 are integrated so as to be detachable to the forward portion 4. In the forward portion 4 CCD 3a constituting the imaging means 3 is provided so as to oppose the center of the light entrance 41 and plural. LEDs (luminous means) 2 are provided so as to surround its circumference. On the other hand in the base portion 42a which is the smaller side of the light shielding hood 42 as mentioned above, the light receiving filter 12 (the part where radiation light passes is made of glass or is a space) is provided. The light shielding hood 42 is detachably and internally fitted in the attachment 41a with the base portion 42a elastically deformed.

According to this embodiment, the light shielding hood 42 and the light receiving filter 12 are integrated so as to be detachable to the forward portion 4. Therefore, as mentioned above, if plural kinds of light shielding hoods 42 are prepared corresponding to the plural light receiving filters 12 with different wavelength characteristics, various diagnostic image information can be obtained by selectively attaching the light shielding hood 42 depending on the diagnostic purpose. As other constructions are the same as the embodiments mentioned above, the common members have the same reference numbers and their explanations are omitted here.

Embodiment 25

Figure 58:
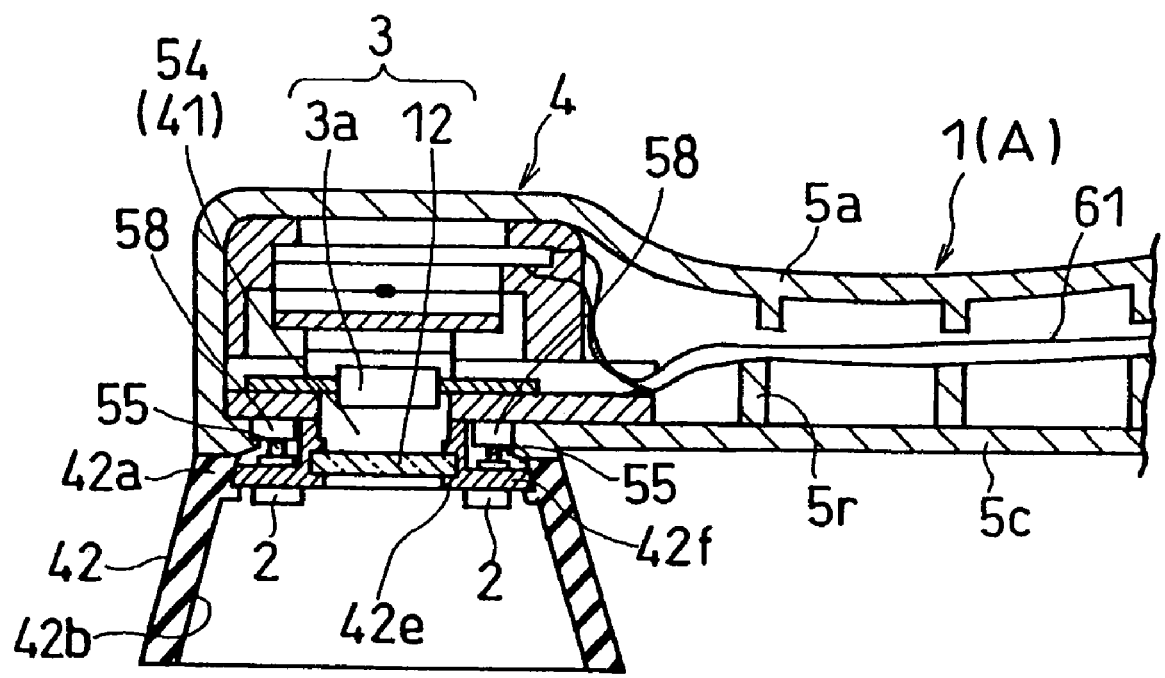
FIG. 58 is a partially cutaway vertical sectional view of a diagnostic imaging apparatus constructed such that a luminous means and a light receiving filter are integrated and are provided at a forward portion detachably, and further the light shielding hood is detachably provided to the integrated one.

FIG. 58 shows one embodiment of the diagnostic imaging apparatus A constructed such that the light receiving filter 12 and the LED (luminous means) 2 are integrated to be detachable to the light entrance (opening 54) 41 of the forward portion 4 via a tubular attachment member 42e and the light shielding hood 42 is detachably provided for the attachment member 42e. In the forward portion 4, the CCD 3a as the imaging means 3 is provided so as to oppose the center of the light entrance 41. The tubular attachment member 42e is provided with an outward brim 42f at its tip end and its inner tube is attached to the light entrance 41 along the optical axis of the CCD 3a via a suitable detachable means (for example screw means).

The light receiving filter 12 is fitted in the inner circumference of the tip of the attachment member 42e and plural LEDs 2 are provided with substantially equal space around its circumferential direction on the face of the outward brim 42f. Convex electrode 55 is provided for each LED 2 at the back face of the outward brim 42f and the receiving electrode 58 is provided at the position corresponding to the convex electrode 55 in the forward portion 4. When the attachment member 42e is attached to the light entrance 41, both electrodes 55 and 58 are electrically connected. Further the above-mentioned light shielding hood 42 is detachably and externally fitted up the periphery of the outside brim 42f with its base portion 42a elastically deformed.

According to this embodiment, if plural combinations of the LED 2 with different emission characteristic and the light receiving filter 12 with different wavelength characteristics are prepared, diversified diagnostic image information can be obtained corresponding to the diagnostic object and the diagnostic purpose by selectively attaching the combination. Further the light shielding hood 42 is detachable by itself so that only the light shielding hood 42 is removed to be subjected

Embodiment 26

Figure 59:
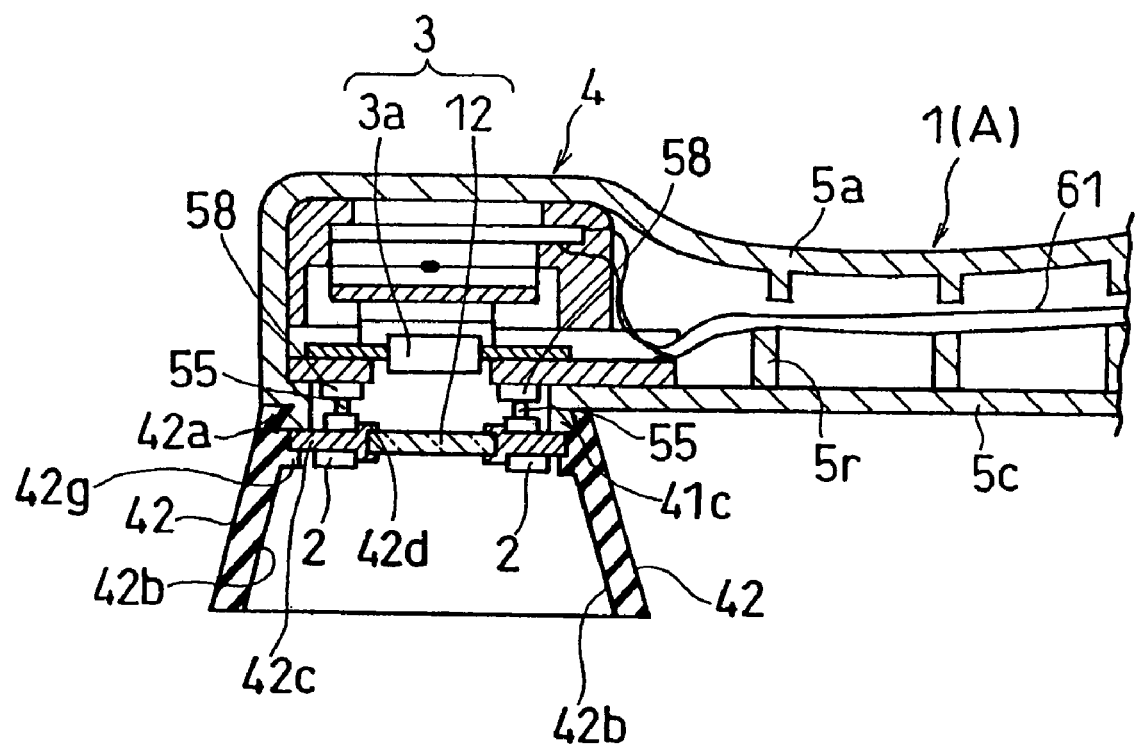
FIG. 59 is a partially cutaway vertical section of a diagnostic imaging apparatus constructed such that a luminous means, a light receiving filter and a light shielding hood are integrated and are provided at a forward portion detachably.

FIG. 59 shows an embodiment of the diagnostic imaging apparatus A constructed such that the light receiving filter 12, the LED (luminous means) 2 and the light shielding hood 42 are integrated so as to be detachable to the light entrance (opening 5) 41 of the forward portion 4. In the forward portion 4 the CCD 3a constituting the imaging means 3 is provided, and in the base portion 42a of the smaller side of the above-mentioned light shielding hood 42 the annular support member 42c provided with the light introduction hole 42d is supported via a stepped part 42g formed in the base portion 42a. Plural LEDs (luminous means) 2 are provided for the annular support member 42c with substantially the same space in the circumferential direction. The light receiving filter 12 is provided for the light introduction hole 42d so as to oppose the CCD 3a. Further, the convex electrode 55 is formed per each LED 2 at the back of the annular support member 42c and the receiving electrode 58 is provided at the position opposing the convex electrode 55 in the forward portion 4, so that both electrodes 55 and 58 are electrically connected when the light shielding hood 42 is externally fitted up the attachment 41a with the base portion 42a elastically deformed.

This embodiment can be used as mentioned above, while supporting the annular support member 42c to the stepped part 42g, when the light shielding hood 42 is externally fitted up the attachment member 41a with the base portion 42a elastically deformed. The light shielding hood 42 is removed from the attachment member 41a together with the annular support member 42c and the annular support member 42c is further removable from the stepped part 42g of the light shielding hood 42. Therefore, if plural annular supporting members 42c combined with the several light receiving filters 12 with different wavelength characteristics and several kinds of LEDs 2 with different light emission characteristics are prepared, various diagnostic image information can be obtained depending on the diagnostic object and the diagnostic purpose by selectively attaching the annular support member 42c. Further, it is advantageous the shielding material 42 is sterilized individually. Other constructions are the same as those in the above-mentioned embodiments, so that the common members have the same reference numerals and their explanations are omitted.

Embodiment 27

Figure 60:
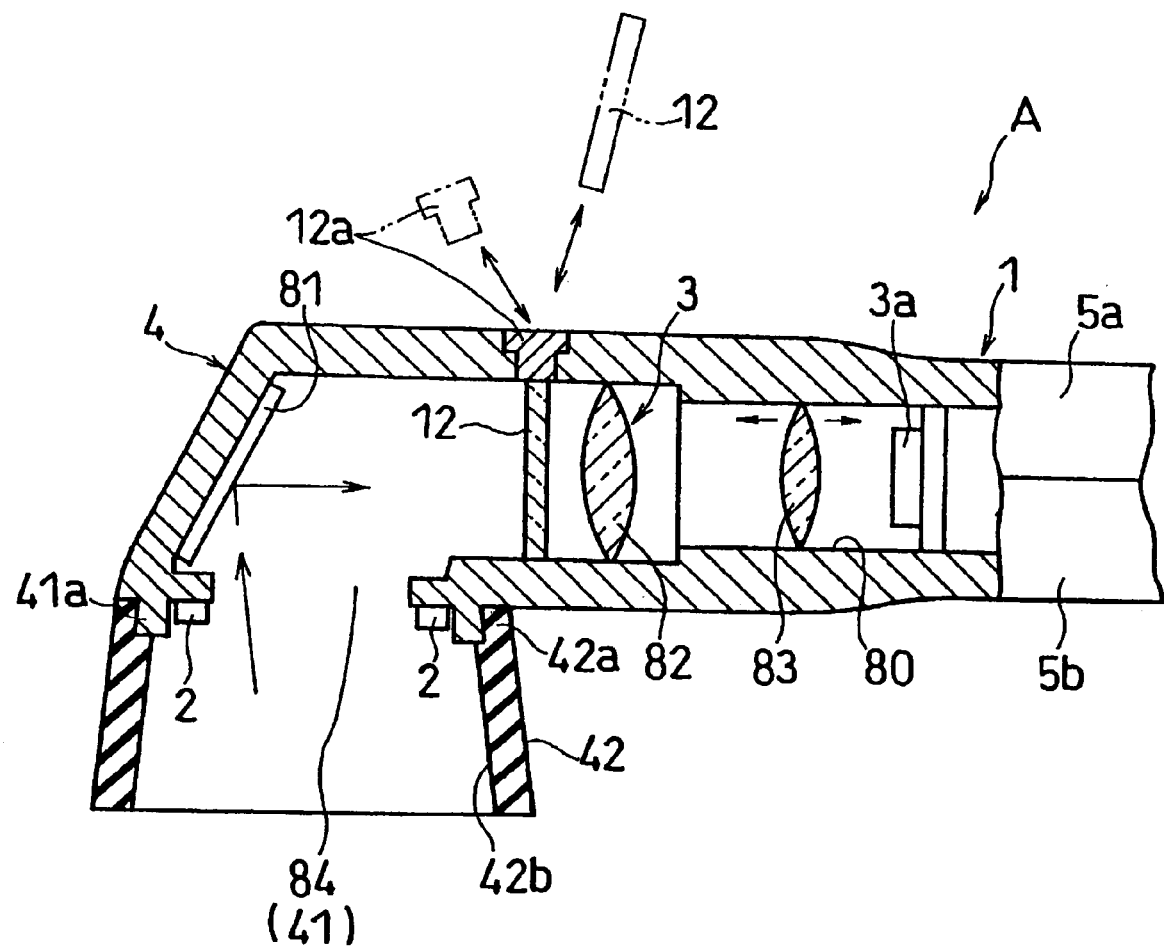
FIG. 60 is a partially cutaway vertical section of other embodiment of a diagnostic imaging apparatus using a optical path changing means.
Figure 61:
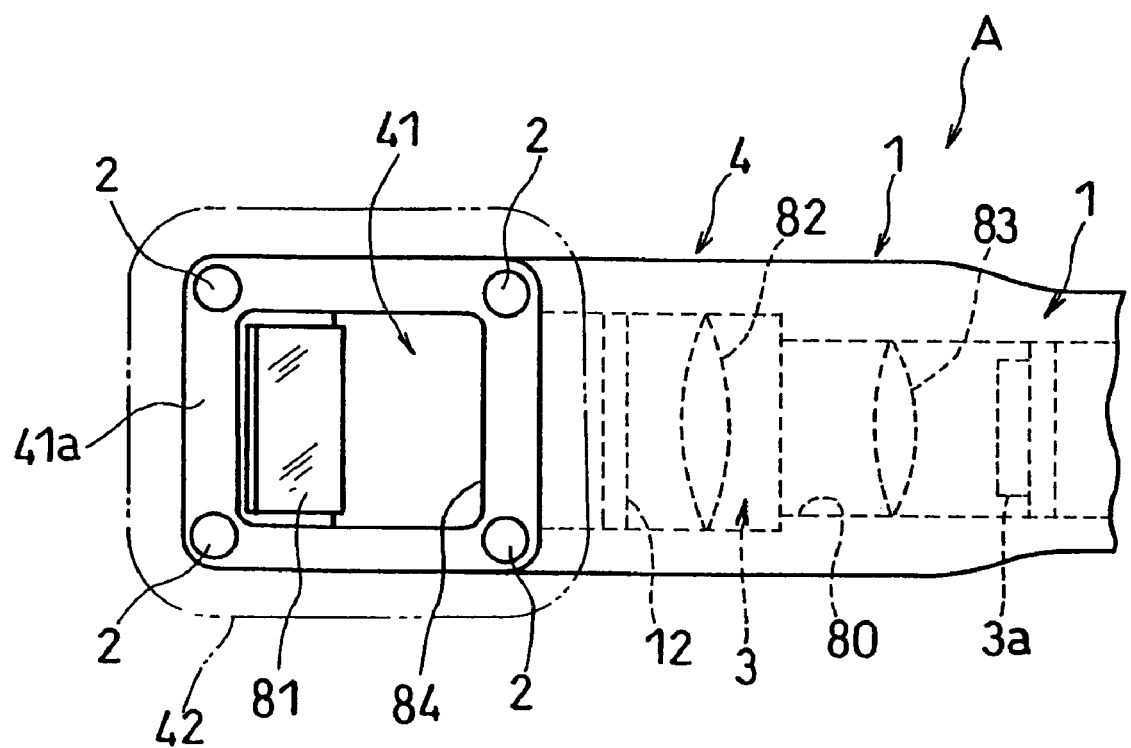
FIG. 61 is a bottom view of the diagnostic imaging apparatus of FIG. 60.

FIG. 60 is a partially cutaway partial vertical section showing the embodiment in which the imaging means has the optical path changing means and FIG. 61 is its bottom view. The diagnostic imaging apparatus A in the figure is constructed such that the CCD 3a constituting the imaging means 3 is provided in the forward portion 4 of the main body 1 in a manner that its optical axis is along the longitudinal direction of the main body 1. In the tip end of the forward portion 4, the mirror (or prism) 81 as a optical path changing means is attached so as to have about 45 degrees against the optical axis and the inner tubular part between the mirror 81 and the CCD 3a forms the light introduction path 80 of the imaging light. The relay lens 82 and the relay lens 83 which is movable along the optical axis are provided for the light introduction path 80. An optical system for forming an optical image on the CCD 3a is comprised of the mirror 81 and the relay lenses 82 and 83. The imaging means 3 is comprised of the CCD 3a and the optical system.

The light receiving filter 12 is detachably provided at a position which is midway of the tubular forward portion 4 and is around in front of (tip end side of) the relay lens 82. The reference numeral 12a indicates a cap for preventing the light receiving filter 12 from escaping. Therefore, if several kinds of light receiving filters with different wavelength characteristics are prepared, the filter may be easily exchanged depending on the diagnostic purpose. If a moving mechanism along the optical axis is further provided for the relay lens 83, a zoom mechanism is achieved. The construction is the same as the embodiment shown in FIG. 35.

Opening for entering light (light entrance 41) 84 is provided for the forward portion 4 so as to open in a direction substantially perpendicular to the optical axis and is communicated with the light introduction path 80. Plural (four in the figure) LEDs (luminous means) 2 are provided around the opening 84, and each one of the LEDs 2 is connected to a lead wire (not shown) embedded in the tubular wall of the forward portion 4 and is further connected to the power source and the switch mechanism (not shown) through the tubular wall of the main body 1. Plural LEDs 2 are constructed by combining plural kinds of LEDs for emitting light with different wavelength as mentioned above, thereby enabling to obtain diversified diagnostic image information by activation and emission control base portion on a suitable time sequence. Further, when the LED 2 is designed to be detachable and is selectively exchanged, more diversified diagnostic image information can be obtained.

Stepped attachment member with different diameters 41a as mentioned above is formed at the light entrance 41 and the tubular light shielding hood 42 made of elastic material such as rubber is externally fitted up the attachment 41a with the base portion 42a elastically deformed. The construction of the light shielding hood 42 is the same as that mentioned above so that the common members have the same reference numerals and their explanations are omitted here.

According to the diagnostic imaging apparatus A in this embodiment, the tip end opening of the light shielding hood 42 is fixed up the diagnostic object member such as teeth, the light from the luminous means 2 is irradiated on the diagnostic object member, and the reflected light or fluorescence is irradiated from the diagnostic object member depending on the wavelength characteristics of the diagnostic object member base portion on the kinds of the luminous means 2. The optical image light base portion on this radiation enters in the forward portion 4 from the opening 84, is reflected at 90 degrees by the mirror 81, passes through the light receiving filter 12, is collected by the relay lenses 82, 83 while proceeding in the light introduction path 80, and forms an image on the CCD 3a. The attaching position of the light receiving filter 12 isn't limited to the figure and the filter 12 may be provided at any position on the light introduction path 80.

Usage of the diagnostic imaging apparatus A in this embodiment is basically the same as that of the diagnostic imaging apparatus A in FIG. 35 other than the light shielding hood 42 is operated in such a manner that the tip end opening thereof is fixed up the diagnostic object member such as teeth, so that detailed explanation such as function is omitted here.

Embodiment 28

Figure 62:
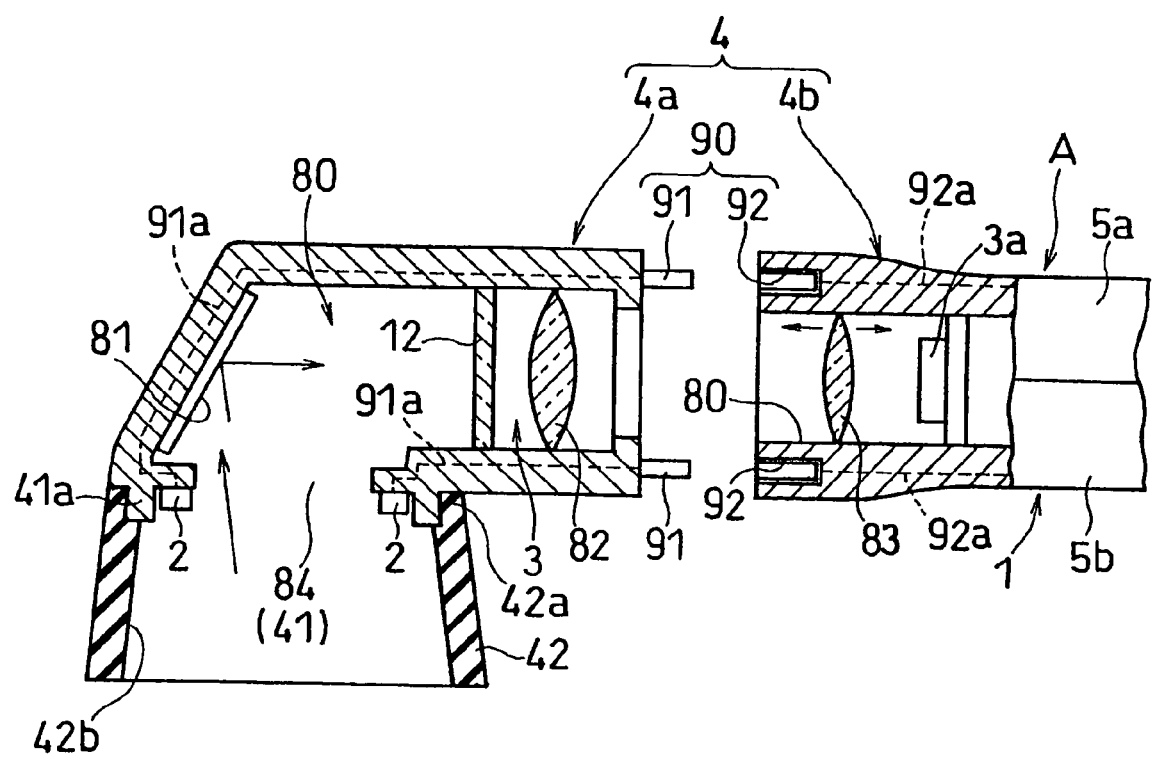
FIG. 62 is a partially cutaway vertical sectional view of still other embodiment of a diagnostic imaging apparatus using a optical path changing means.

FIG. 62 shows an embodiment in which the imaging means is provided with the optical path changing means and the forward portion 4 is able to be separated into the head portion 4a and the base portion 4b. The common members with the embodiment 27 have the same reference numbers. The mirror (or prism) 81 as a optical path changing means is provided so as to have about 45 degrees against the optical axis in the tubular head portion 4a and the CCD 3a is provided in the tubular base portion 4b of the forward portion 4. When the head portion 4a and the base portion 4b are connected by means of a connection means 90 mentioned hereinafter, the inner tubular part between the mirror 81 and the CCD 3a is served as the light introduction path 80 of the imaging light.

The relay lens 82 is provided in the head portion 4a along the light introduction path 80 and the relay lens 83 movable along the optical axis is provided in the base portion 4b. Optical system for forming an optical image on the CCD 3a is constructed with the mirror 81 and the relay lenses 82, 83. With the CCD 3a and the optical system the imaging means 3 is constructed. Opening for entering light (light entrance 41) 84 is formed so as to open in a direction substantially perpendicular to the optical axis of the head portion 4a and is communicated with the light introduction path 80. The light receiving filter 12 is provided around in front of (tip end side of) the relay lens 82.

Plural LEDs (luminous means) 2 are provided with a space along the circumferential direction around the opening 84. Lead wire 91a . . . embedded in the wall of the head portion 4a is connected to each LED 2 and is further connected to the male electrode 91 . . . projecting at the base portion 4b side end of the head portion 4a. On the other hand, the female electrode 92 . . . is provided in a concave manner corresponding to the male electrode 91 . . . at the head portion 4a side end of the base portion 4b. These female electrodes 92 . . . are connected to the power source (not shown) in the main body 1 via the lead wire 92a. . . embedded in the wall of the base portion 4b.

The fitted male electrode 91 . . . and female electrode 92 . . . comprise the connection means 90 of the head portion 4a and the base portion 4b and further achieve an electrical connection of both electrodes. Therefore, manual operation of the head portion 4a enables easy attachment and detachment to the base portion 4b. Hereby, the male electrode 91 . . . and the female electrode 92 . . . are electrically connected so that power is supplied to the LED 2 from the power source by the above-mentioned switching operation, thus executing activation and emission.

The stepped attachment member with different diameters 41a is formed at the light entrance 41 as mentioned above. Like the embodiment 27, the tubular light shielding hood 42 made of elastic material such as rubber is externally fitted up the attachment 41a with the base portion 42a elastically deformed. The separatable construction of the forward portion 4 into the head portion 4a and the base portion 4b is the same as that in FIG. 38. Therefore, those explanations are omitted here. In the embodiments 27 and 28, the mirror 81 and the LED 2 may be integrated to be detachable to the light entrance via a suitable support member.

Embodiment 29

Figure 63:
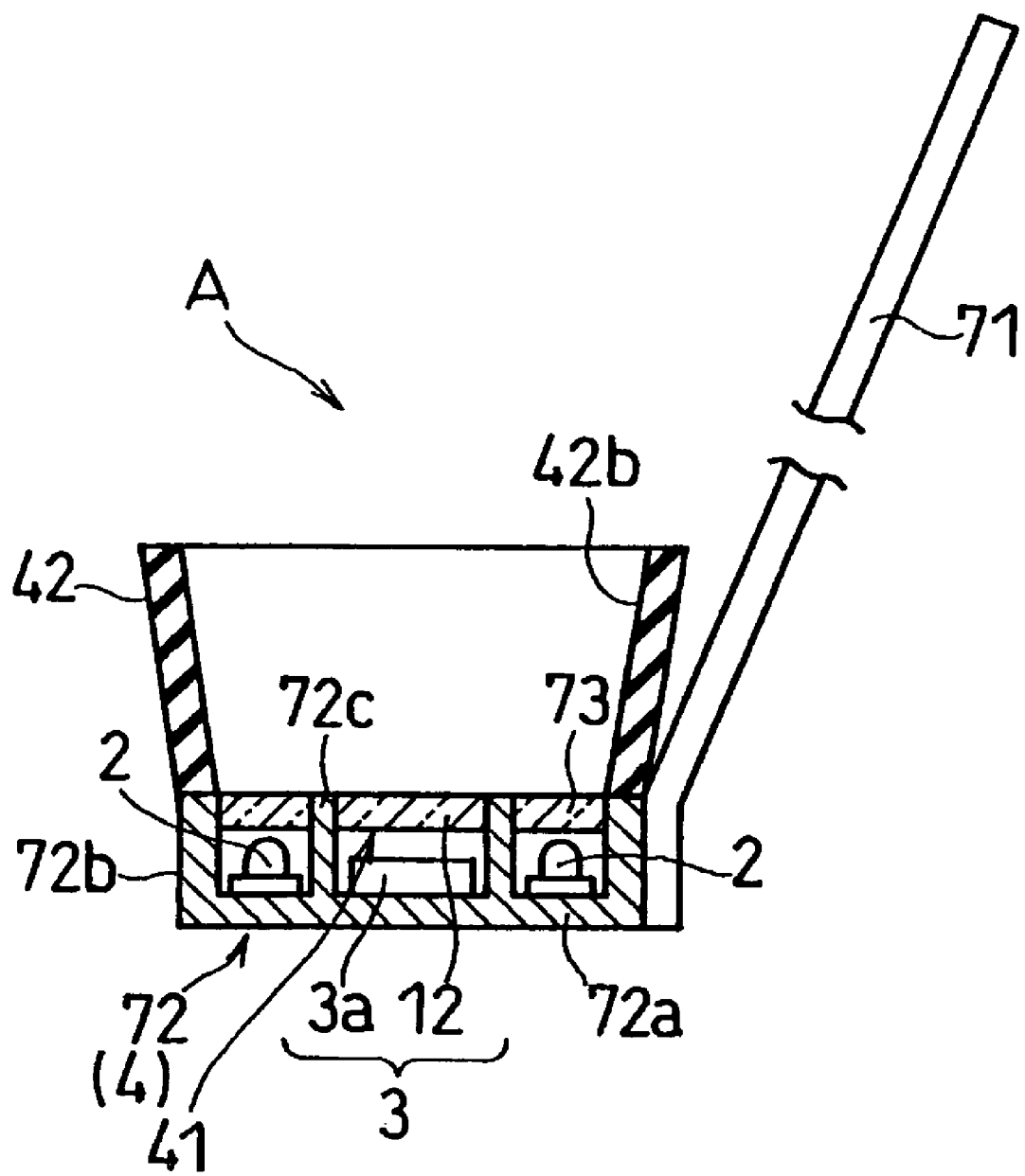
FIG. 63 is a partially cutaway side view of a dental mirror type diagnostic imaging apparatus.
Figure 64:
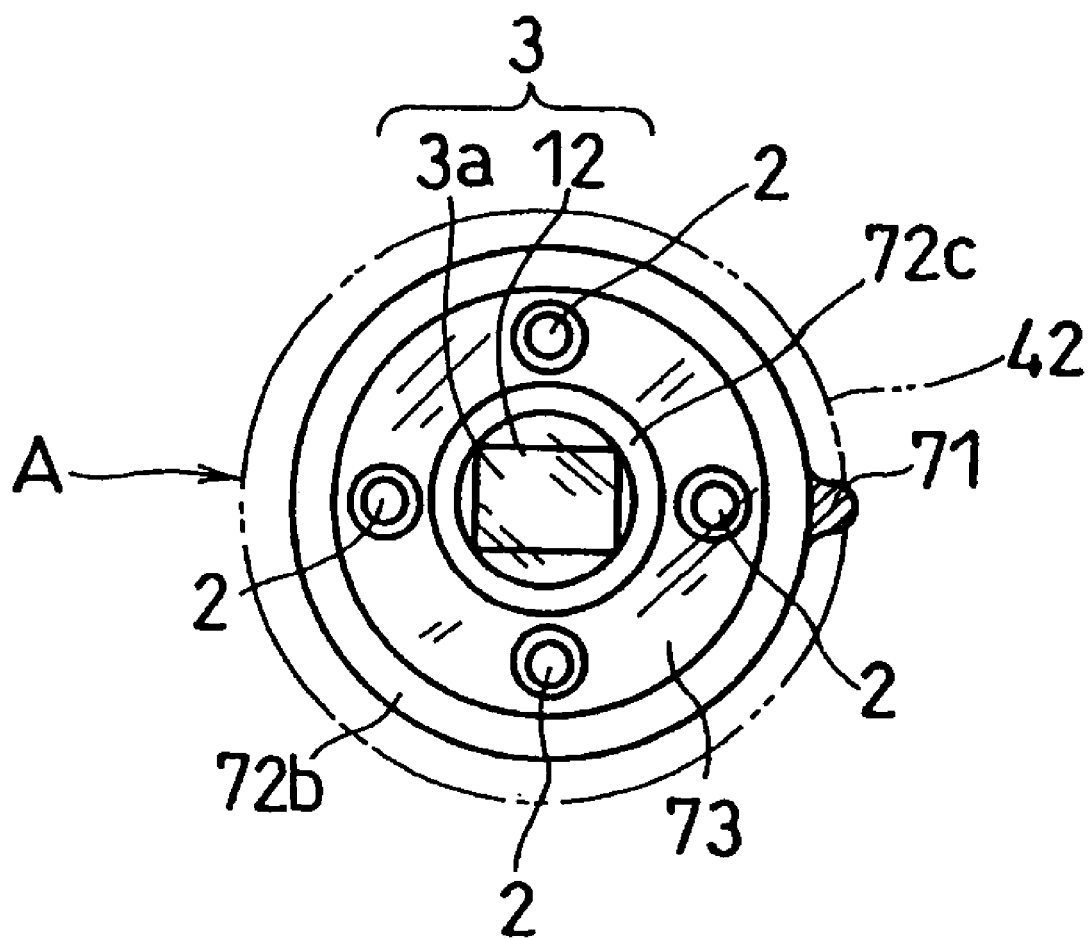
FIG. 64 is a plane view of a substantial part of the diagnostic imaging apparatus of FIG. 63.
Figure 65:
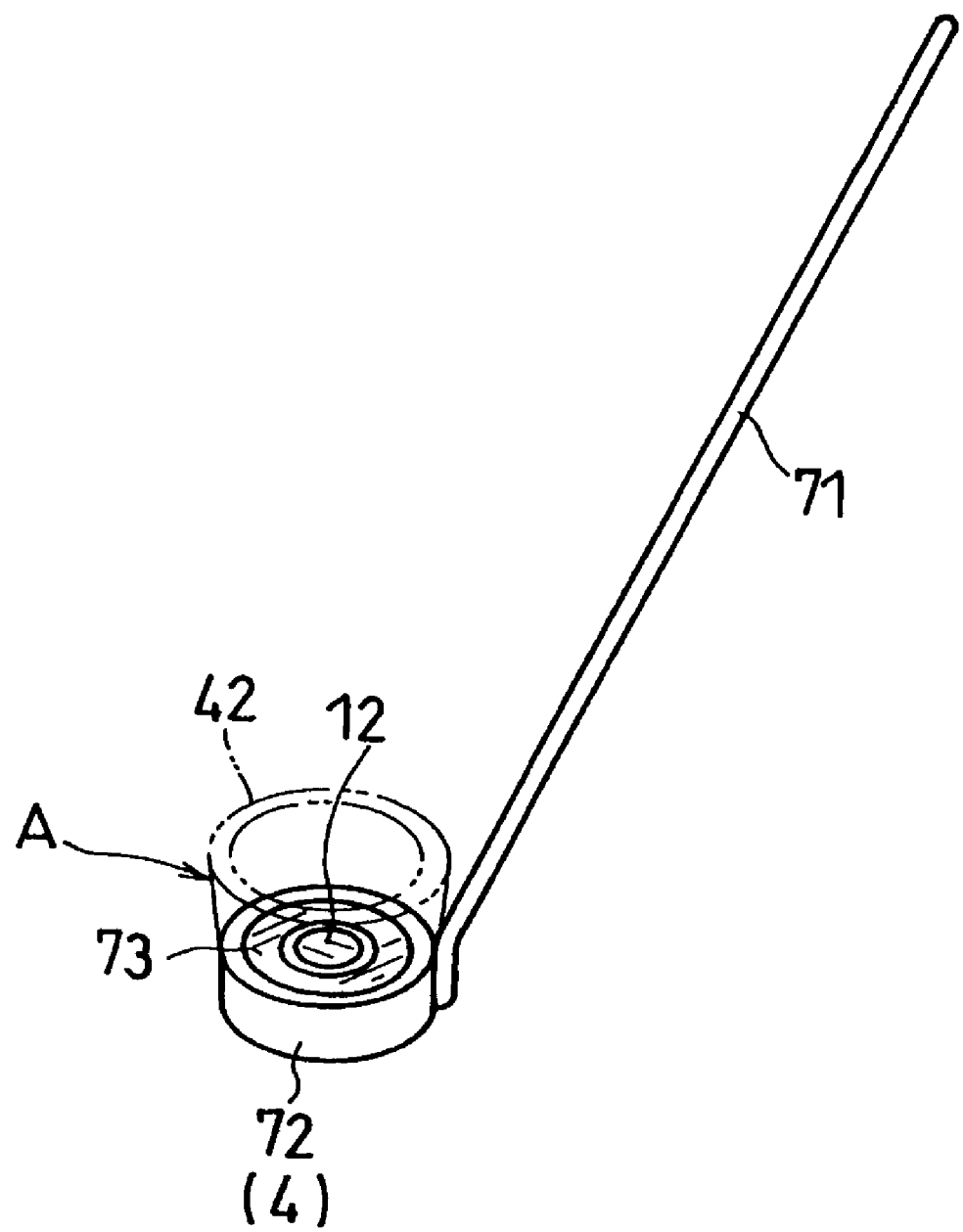
FIG. 65 is a perspective view of the diagnostic imaging apparatus of FIG. 63.

FIG. 63-FIG. 65 show an embodiment in which the light shielding hood 42 is attached to the dental mirror type diagnostic imaging apparatus A shown in FIG. 39-FIG. 41. The opening of the frame 72 is the light entrance 41 and the tubular light shielding hood 42 made of elastic material such as rubber is detachably attached to the light entrance 41. Thus the diagnostic imaging apparatus A is so compact that it can be operated in the same manner as using the dental mirror by fixing the light shielding hood 42 up the teeth. Therefore, it can easily, operably and conveniently execute photography of the diagnostic object member (photography object) in oral cavity without being affected by disturbance light.

The appearance of the diagnostic imaging apparatus A mentioned above may be a construction such that the light axes of the imaging means 3 and the luminous means 2 are perpendicular to the longitudinal direction of the main body 1 (see FIG. 1-FIG. 5, FIG. 42-FIG. 47). The appearance may be a crooked construction in which the imaging means 3 and the luminous means 2 are provided, or a liner construction such the imaging means and the radiation light source are provided at the forward portion 4 along the longitudinal direction of the main body (see JP-Y-6-30163). Further, the apparatus A may be constructed in a manner that the control box H shown in FIG. 2 or FIG. 43 is formed very compact with a display function and a control function like a mobile phone and is connected to the main body 1.

According to the above-mentioned diagnostic imaging apparatus A, the reflected light generated from the photography object by using infrared light with strong permeability and the fluorescence excited by radiating exciting light are received and those lights can be outputted as the diagnostic image information by the imaging means 3 in addition to the image obtained by the white light source. Thus, detection of dental caries or incipient dental caries, observation of dental caries condition, confirmation of dental caries progress, observation of tooth deterioration and gum deterioration can be accurately executed. In addition existence of damage or crack of the tooth, existence of dental calculus and dental plaque, attached condition of dental calculus and dental plaque, and attached condition of restoration are diagnosed. In the present invention the diagnostic imaging apparatus A with such a superior function can be provided in a compact body, at low cost and with good facility and convenience. Namely, the reflected light from the diagnostic object and/or the fluorescence generated by exiting light accompanied with radiation from the luminous means are received in the imaging means 3 to form a predetermined diagnostic image information. If the light shielding hood 42 is attached, the adverse affect by the disturbance light is excluded. Therefore, the damage on the tooth surface, caries in the tooth, the depth of crack and the condition of gum are recognized rapidly, easily and clearly, thereby achieving a useful apparatus capable of executing accurate diagnosis as a compact camera type imaging apparatus. Further, a standard photography using the light with different wavelength as radiation light is executed so that image processing such as overlapping or sweeping of the images using the radiation light with different wavelength can be done. Therefore, the fluorescence image of the lesioned part is easily overlapped on the visible light image. Hereby, recognition of the lesioned part under room light or sunbeam which has been difficult with eyes can be achieved. Further, if such a simple diagnosis is executed at home, one can think out the way of teeth brushing by himself or such a diagnosis can come in useful for health control of himself or his family.

The invention claimed is:
1. A diagnostic imaging apparatus comprising:
 a main body freely held between one's fingers;
 a forward portion of said main body comprising a head portion;
 a luminous means for irradiating at least one of lights selected from exciting light, infrared light and ultraviolet light;
 a means for imaging provided at said forward portion of said main body, comprising a solid a solid-state image sensing device and means for forming an optical image of a diagnostic object on said solid-state image sensing device;

wherein said imaging means receives a reflection light from said diagnostic object and/or a fluorescence of said diagnostic object to output a predetermined diagnostic image information when light is irradiated from said luminous means to said diagnostic object;

a means for image storing provided in said main body;

a control means for recording and storing the predetermined diagnostic image information formed by said means for imaging, as a static image; and automatic photography control means for executing a predetermined time sequence by manual operation of a photography switch, provided with said image storing means, to sequentially store and keep in a memory the predetermined diagnostic image information formed by said imaging means each time irradiation light with a different wavelength is selectively irradiated.

2. The diagnostic imaging apparatus as set forth in claim 1, wherein a luminous means for irradiating white light is further provided.

3. The diagnostic imaging apparatus as set forth in claim 1, wherein said forward portion comprises a detachable attachment constituting a part of said forward portion; and wherein said optical means and/or said luminous means is provided in said attachment.

4. The diagnostic imaging apparatus as set forth in claim 1 or 3, wherein said optical means is a light receiving filter.

5. The diagnostic imaging apparatus as set forth in claim 1, wherein a light receiving filter for transmitting only a light with specific wavelength range is provided adjacent to a light receiving part of said imaging means.

6. The diagnostic imaging apparatus as set forth in claim 1, wherein said luminous means comprises any one of LED, a laser oscillator, and a halogen lamp.

7. The diagnostic imaging apparatus as set forth in claim 6, wherein said LED and said laser oscillator are so constructed as to switch the wavelength of the emitting light.

8. The diagnostic imaging apparatus as set forth in claim 1 or 3, wherein said head portion of said forward portion is provided with said luminous means and/or a light receiving filter for transmitting only the light with specific wavelength range.

9. The diagnostic imaging apparatus as set forth in claim 1, wherein said optical means and/or said luminous means is provided at said forward portion.

10. The diagnostic imaging apparatus as set forth in claim 1, wherein said luminous means is so constructed to be detachable to said forward portion.

11. The diagnostic imaging apparatus as set forth in claim 1, wherein said optical means and the luminous means are integrated so as to be detachable to said forward portion.

12. The diagnostic imaging apparatus as set forth in claim 1, wherein said forward portion is so constructed as to be detachable to said main body.

13. The diagnostic imaging apparatus as set forth in claim 1, wherein said luminous means comprises a light emitting member and a radiation filter for transmitting only the light with specific wavelength range among the light emitted from said light emitting member, said radiation filter being provided adjacent to said light emitting member.

14. The diagnostic imaging apparatus as set forth in claim 1, wherein said optical means includes a optical path changing means for changing the optical path from said diagnostic object when the light is irradiated from said luminous means to said diagnostic object.

15. The diagnostic imaging apparatus as set forth in claim 14, wherein said forward portion is capable of being separated into a head portion including said optical path changing means and a base portion including said solid-state image sensing device.

16. The diagnostic imaging apparatus as set forth in claim 15, wherein said head portion of said forward portion is provided with a luminous means and/or a light receiving filter which passes only the light with specific wavelength range.

17. The diagnostic imaging apparatus as set forth in claim 1 or 15, wherein said head potion is provided with said luminous means; wherein separation function at said forward portion is achieved by a coupling means by which said head portion and said base portion are detachable each other; and wherein an electric connection member for supplying electric power to said luminous means is interposed for said coupling means.

18. The diagnostic imaging apparatus as set forth in claim 5, wherein a filter detachable means detachable to said light receiving filter is provided in said forward portion of said main body.

19. The diagnostic imaging apparatus as set forth in claim 5, wherein a filter unit having plural kinds of light receiving filters is further provided in the forward portion of said main body via filter changing means, said filter changing means selectively and switchably positioning said light receiving filter at predetermined position.

20. The diagnostic imaging apparatus as set forth in claim 19, wherein said filter unit comprises said plural kinds of light receiving filters rotationally disposed around an axis which is parallel to/or normal to an optical axis direction of said imaging means or said luminous means.

21. The diagnostic imaging apparatus as set forth in claim 20, wherein said switching means comprises a motor by which said filter unit is driven to be rotated around said axis and a switching control means for driving said motor and selectively and switchably positioning said light receiving filter at predetermined position on a filter switching signal.

22. The diagnostic imaging apparatus as set forth in claim 20, wherein said filter switching signal is synchronously control with an irradiation signal of said luminous means.

23. The diagnostic imaging apparatus as set forth in claim 1 or 3, wherein plural luminous means are provided around a light receiving member of said imaging means in a manner that said light receiving member is disposed at its center.

24. The diagnostic imaging apparatus as set forth in claim 1, wherein said luminous means, said optical means or a light shielding hood is detachably attached to said light entrance by itself or at least two of them are detachably attached to said light entrance by combining and integrating themselves.

25. The diagnostic imaging apparatus as set forth in claim 24, wherein said light shielding hood is made of a soft elastic tubular member such as rubber or the like.

26. The diagnostic imaging apparatus as set forth in claim 24, wherein said light shielding hood is made of a non-light-permeable material.

27. The diagnostic imaging apparatus as set forth in claim 25 or 26, wherein the inner wall of said light shielding hood has a light-reflecting surface.

28. The diagnostic imaging apparatus as set forth in claim 27, wherein said light-reflecting surface is mirror finished.

29. The diagnostic imaging apparatus as set forth in claim 1, wherein a power source and a radio transmitter are provided in said main body so as to transmit the diagnostic image information formed by said imaging means to an external receiving apparatus via cordless manner.

30. The diagnostic imaging apparatus as set forth in claim 1, wherein said luminous means includes a light emitting member for emitting the light with wavelength suitable for hardening photo-polymerization resin.

31. The diagnostic imaging apparatus as set forth in claim 5, wherein the wavelength of the light irradiated from said luminous means is 400±30 nm and said light receiving filter provided adjacent to said light receiving member of said imaging means is so constructed as to transmit only the light with wavelength over than 430 nm.

* * * * *